US012715927B2

(12) United States Patent
Gromada et al.

(10) Patent No.: US 12,715,927 B2
(45) **Date of Patent: *Aug. 25, 2026**

(54) MONOSPECIFIC ANTIBODIES THAT ANTAGONIZE LEPTIN RECEPTOR

(71) Applicant: Regeneron Pharmaceuticals, Inc., Tarrytown, NY (US)

(72) Inventors: Jesper Gromada, Concord, MA (US); Panayiotis Stevis, West Orange, NJ (US); Judith Altarejos, Armonk, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 785 days.

This patent is subject to a terminal disclaimer.

(21) Appl. No.: 18/056,411

(22) Filed: Nov. 17, 2022

(65) Prior Publication Data

US 2023/0235068 A1 Jul. 27, 2023

Related U.S. Application Data

(60) Continuation of application No. 16/736,760, filed on Jan. 7, 2020, now Pat. No. 11,535,675, which is a division of application No. 15/807,426, filed on Nov. 8, 2017, now Pat. No. 10,550,192.

(60) Provisional application No. 62/419,062, filed on Nov. 8, 2016.

(51) Int. Cl.

| | |
|---|---|
| ***C07K 16/28*** | (2006.01) |
| ***A61K 39/395*** | (2006.01) |
| *A61K 39/00* | (2006.01) |
| *A61P 3/00* | (2006.01) |
| *C07K 14/72* | (2006.01) |

(52) U.S. Cl.

CPC ...... *C07K 16/2869* (2013.01); *A61K 39/3955* (2013.01); *A61K 2039/505* (2013.01); *A61P 3/00* (2018.01); *C07K 14/72* (2013.01); *C07K 2317/21* (2013.01); *C07K 2317/34* (2013.01); *C07K 2317/56* (2013.01); *C07K 2317/565* (2013.01); *C07K 2317/70* (2013.01); *C07K 2317/76* (2013.01); *C07K 2317/92* (2013.01)

(58) Field of Classification Search

CPC . C07K 16/2869; C07K 14/72; A61K 39/3955

See application file for complete search history.

(56) References Cited

U.S. PATENT DOCUMENTS

| | | | |
|---|---|---|---|
| 4,596,556 | A | 6/1986 | Morrow et al. |
| 4,790,824 | A | 12/1988 | Morrow et al. |
| 4,941,880 | A | 7/1990 | Burns |
| 4,946,778 | A | 8/1990 | Ladner et al. |
| 5,064,413 | A | 11/1991 | McKinnon et al. |
| 5,312,335 | A | 5/1994 | McKinnon et al. |
| 5,383,851 | A | 1/1995 | McKinnon et al. |
| 5,399,163 | A | 3/1995 | Peterson et al. |
| 5,717,073 | A | 2/1998 | Wijdenes et al. |
| 5,932,448 | A | 8/1999 | Tso et al. |
| 5,965,521 | A | 10/1999 | Stephens et al. |
| 6,005,080 | A | 12/1999 | Snodgrass et al. |
| 6,096,002 | A | 8/2000 | Landau |
| 6,096,506 | A | 8/2000 | Lee et al. |
| 6,129,914 | A | 10/2000 | Weiner et al. |
| 6,329,511 | B1 | 12/2001 | Vasquez et al. |
| 6,380,363 | B1 | 4/2002 | Tartaglia et al. |
| 6,620,135 | B1 | 9/2003 | Weston et al. |
| 6,977,240 | B1 | 12/2005 | Tartaglia et al. |

(Continued)

FOREIGN PATENT DOCUMENTS

| | | | |
|---|---|---|---|
| AU | 2004201496 | C1 | 8/2018 |
| CN | 107760761 | | 3/2018 |

(Continued)

OTHER PUBLICATIONS

Sandhu et al, 1992. Critical Reviews in Biotechnology. 12(5/6): 437-462.*

(Continued)

*Primary Examiner* — Zachary C Howard

(74) *Attorney, Agent, or Firm* — FisherBroyles, LLP; Christy G. Rothwell; Gabriele Amodeo

(57) ABSTRACT

The present invention provides antibodies and antigen-binding fragments of antibodies that bind to leptin receptor (LEPR), and methods of using the same. According to certain embodiments, the invention includes antibodies and antigen-binding fragments of antibodies that bind LEPR and antagonize LEPR signaling. In certain embodiments, the invention includes antibodies and antigen-binding fragments of antibodies that bind LEPR in the presence or absence of leptin. In other embodiments, the invention includes antibodies and antigen-binding fragments of antibodies that exhibit partial agonism of LEPR signaling. The antibodies and antigen-binding fragments of the present invention are useful for the treatment of various conditions, including but not limited to congestive heart failure cachexia, pulmonary cachexia and cancer cachexia, autoimmune disorders such as inflammatory bowel disease, lupus erythematosus, multiple sclerosis, psoriasis, cardiovascular diseases, elevated blood pressure, neurodegenerative disorders, depression, cancer such as hepatocellular carcinoma, melanoma, breast cancer, and other diseases and disorders associated with or caused by elevated leptin signaling.

20 Claims, 3 Drawing Sheets

Specification includes a Sequence Listing.

(56) References Cited

U.S. PATENT DOCUMENTS 7,067,472 B1 6/2006 Feng et al.
7,067,477 B2 6/2006 MacLeod
7,183,254 B2 2/2007 DePaoli et al.
7,261,893 B2 8/2007 Veldman et al.
7,294,754 B2 11/2007 Poueymirou et al.
7,307,142 B2 12/2007 Gertler et al.
7,320,789 B2 1/2008 Aghahanian et al.
7,521,048 B2 4/2009 Gliniak et al.
7,524,937 B2 4/2009 Carter et al.
7,575,878 B2 8/2009 Tavernier et al.
7,576,259 B2 8/2009 Poueymirou et al.
7,632,499 B2 12/2009 Davies et al.
7,635,760 B2 12/2009 Han et al.
7,659,442 B2 2/2010 Poueymirou et al.
7,807,159 B2 10/2010 Chin et al.
7,863,240 B2 1/2011 Ilan et al.
7,888,486 B2 2/2011 Walsh et al.
8,017,634 B2 9/2011 Sinclair et al.
8,318,666 B2 11/2012 DePaoli et al.
8,697,396 B2 4/2014 Dall'Acqua et al.
8,840,894 B2 9/2014 Stitt et al.
8,846,724 B2 9/2014 Sinclair et al.
8,871,209 B2 10/2014 Stitt et al.
8,969,291 B2 3/2015 Ilan et al.
9,221,902 B2 12/2015 Smider et al.
9,260,515 B2 2/2016 Stitt et al.
9,332,742 B2 5/2016 Mcwhirter et al.
9,334,331 B2 5/2016 Igawa et al.
9,421,257 B2 8/2016 Ilan et al.
9,718,881 B2 8/2017 Gromada et al.
9,890,212 B2 2/2018 Stitt et al.
10,023,644 B2 7/2018 Gromada et al.
10,253,102 B2 4/2019 Gromada et al.
10,400,036 B2 9/2019 Stitt et al.
10,421,807 B2 9/2019 Gonzales et al.
10,526,403 B2 1/2020 Gromada et al.
10,550,192 B2 2/2020 Gromada et al.
10,618,968 B2 4/2020 Gromada et al.
10,934,249 B2 3/2021 Pordy et al.
11,248,044 B2 2/2022 Donahue et al.
11,535,675 B2 12/2022 Gromada et al.
11,608,381 B2 3/2023 Gromada et al.
11,834,500 B2 12/2023 Gromada et al.
12,275,792 B2 4/2025 Gromada et al.
12,371,503 B2 7/2025 Gromada et al.
2004/0202652 A1 10/2004 Karsenty et al.
2004/0253242 A1 12/2004 Bowdish et al.
2006/0068429 A1 3/2006 Bailleul et al.
2007/0178095 A1 8/2007 Smith et al.
2008/0078000 A1 3/2008 Poueymirou et al.
2009/0148436 A1 6/2009 Lavallie et al.
2009/0234106 A1 9/2009 Han et al.
2010/0166764 A1 7/2010 Sayers et al.
2010/0260772 A1 10/2010 Karsenty
2011/0092417 A1 4/2011 Artymiuk et al.
2011/0293630 A1 12/2011 Stitt et al.
2012/0204278 A1 8/2012 Bradley et al.
2012/0258073 A1 10/2012 Gerdes et al.
2013/0122007 A1 5/2013 Stitt et al.
2014/0134162 A1 5/2014 Stavenhagen et al.
2014/0171623 A1 6/2014 Dall'Acqua et al.
2014/0243504 A1 8/2014 Davis et al.
2018/0037648 A1 2/2018 Ilan et al.
2018/0127508 A1 5/2018 Gromada et al.
2019/0002569 A1 1/2019 Belaid-Choucair et al.
2019/0185562 A1 6/2019 Gromada et al.
2019/0309079 A1 10/2019 Gromada
2020/0031946 A1 1/2020 Gromada et al.
2020/0123264 A1 4/2020 Gromada et al.
2022/0098313 A1 3/2022 Oral et al.
2022/0112293 A1 4/2022 Gromada et al.
2022/0280641 A1 9/2022 Gromada et al.
2023/0235068 A1 7/2023 Gromada et al.
2024/0158497 A1 5/2024 Gromada et al.
2024/0247071 A2 7/2024 Altarejos et al.
2025/0051465 A1 2/2025 Gromada et al.
2025/0320301 A1 10/2025 Gromada et al.

FOREIGN PATENT DOCUMENTS

EP 981365 B1 12/2004
EP 885299 B1 10/2005
EP 0730606 B1 11/2005
EP 0879286 B1 4/2008
EP 1619250 B1 11/2009
EP 1444516 B1 7/2010
EP 1019432 B1 1/2012
EP 2219031 B1 4/2013
EP 2780368 9/2014
EP 2649184 B1 7/2015
EP 3298889 A1 3/2018
EP 2989894 B1 8/2020
EP 3362477 B1 1/2022
JP 1991219894 9/1991
WO WO 1996/005309 2/1996
WO WO 1996/08510 3/1996
WO WO 1997/019952 6/1997
WO WO 1997/025425 7/1997
WO WO 1997/26272 7/1997
WO WO 1997/26335 7/1997
WO WO 1997/26370 7/1997
WO WO 1997/26523 7/1997
WO WO 1997/27286 7/1997
WO WO 1997/41263 11/1997
WO WO 199822128 A1 5/1998
WO WO 1998/48831 11/1998
WO WO 2002/36789 5/2002
WO WO 2002/66630 8/2002
WO WO 2005/049655 6/2005
WO WO 2006/053883 5/2006
WO WO 2010070094 6/2010
WO WO 2011/004192 1/2011
WO WO 2011/097603 8/2011
WO WO 2011130499 A1 10/2011
WO WO 2012/141798 10/2012
WO WO 2012/148873 11/2012
WO WO 2013/022782 2/2013
WO WO 2013/184761 12/2013
WO WO 2014/043361 A1 3/2014
WO WO 2015/124588 8/2015
WO WO 2016039796 A2 3/2016
WO WO 2016168613 A1 10/2016
WO WO 2017/066204 A1 4/2017
WO WO 2018089532 5/2018
WO WO 2019195796 10/2019
WO WO 2020131910 A1 6/2020
WO WO 2022060827 A3 4/2022

OTHER PUBLICATIONS

"A Study to Examine the Safety, Tolerability and Biological Effects of REGN4461 in Healthy Volunteers [ClinicalTrials.gov posting, identifier NCT03530514]. Accessed May 21, 2018."

"Expanded Access to REGN4461 for Patients With 1) Generalized Lipodystrophy, 2) Partial Lipodystrophy or 3) Monogenic Obesity Due to LEP or LEPR Loss of Function [ClinicalTrials.gov posting, identifier NCT04710056]. Accessed Jan. 13, 2021."

"Study of REGN4461, a Leptin Receptor Agonist Antibody, in Patients with Generalized Lipodystrophy [ClinicalTrials.gov posting, identifier NCT04159415]. Accessed Nov. 12, 2019."

Accession No. NP_001003679.1 to: Protein [Internet]. Bethesda (MD): National Library of Medicine (US), National Center for Biotechnology Information; [2019]—Accession No. NP_001003679.1, "Leptin Receptor Isoform 3 Precursor [*Homo sapiens*]", cited on Mar. 12, 2019, [online], [retrieved on Mar. 20, 2019]. Retrieved from: https://www.ncbi.nlm.nih.gov/protein/51093379/, 6 pages.

Accession No. NP_002175.2 to: Protein [Internet]. Bethesda (MD): National Library of Medicine (US), National Center for Biotechnology Information; [2019]—Accession No. NP_002175.2, "Interleukin-6 Receptor Subunit Beta Isoform 1 Precursor [*Homo

(56) References Cited

OTHER PUBLICATIONS

*sapiens*]", cited on Mar. 12, 2019, [online], [retrieved on Mar. 20, 2019]. Retrieved from: https://www.ncbi.nlm.nih.gov/protein/NP_002175.2, 6 pages.
Ajluni et al. (2017) "Spectrum of Disease Associated with Partial Lipodystrophy: Lessons from a Trial Cohort", Clin Endocrinol (Oxf), 86(5): 698-707.
Akinci et al. (2017) "Clinical Presentations, Metabolic Abnormalities and End-Organ Complications in Patients with Familial Partial Lipodystrophy", Metabolism—Clin and Exp., 72: 109-119.
Akinci et al. (2018) "Phenotypic and Genetic Characteristics of Lipodystrophy: Pathophysiology, Metabolic Abnormalities, and Comorbidities", Curr Diab Rep., 18(12):143, 1-12.
Akinci et al. (2018) "Renal Complications of Lipodystrophy: A Closer Look at the Natural History of Kidney Disease", Clin Endocrinol (Oxf), 89(1):65-75.
Akinci et al. (2020) "Adipose Tissue, Appetite, and Obesity, Mechanisms and Treatment of Obesity in Humans, The Treatment of Partial Lipodystrophy in the Setting of Neutralizing Antibody Against Metreleptin with Leptin Receptor Agonist REGN4461", Journal of the Endocrine Society, vol. 4, Abstract Supplement, A544 (OR33-02).
Akinci et al. (2020) "The Complicated Clinical Course in a Case of Atypical Lipodystrophy After Development of Neutralizing Antibody to Metreleptin: Treatment with Setmelanotide", Endocrinol Diabetes Metab Case Rep., 1-9.
Altschul (1991) "Amino Acid Substitution Matrices from an Information Theoretic Perspective", J. Mol. Biol., 219: 555-565.
Altschul (1993) "A Protein Alignment Scoring System Sensitive at all Evolutionary Distances", J. Mol. Evol., 36:290-300.
Altschul et al. (2005) "Protein Database Searches Using Compositionally Adjusted Substitution Matrices", FEBS J., 272(20): 5101-5109.
Anonymus (2019) "Study of REGN4461, a Leptin Receptor Agonist Antibody, in Patient with Generalized Lipodystrophy", Full Text View, ClinicalTrials.gov, Nov. 12, 2019, 10 pages.
Anthony (2008) "Nutrition Screening Tools for Hospitalized Patients", Nutr. Clin. Pract. 23: 373-382.
Aslam et al. (2013) "Acquired Generalized Lipodystrophy Associated with Peripheral Tcell Lymphoma with Cutaneous Infiltration", International J. Dermatol., 54: 827-829.
Baca et al. (1997) "Antibody Humanization Using Monovalent Phage Display," J Biol Chem., 272(16): 10678-10684.
Bahrenberg et al. (2002) "Identification of the Critical Sequence Elements in the Cytoplasmic Domain of Leptin Receptor Isoforms Required for Janus Kinase/Signal Transducer and Activator of Transcription Activation by Receptor Heterodimers", Molecular Endocrinology, 16(4): 859-872.
Barbas (1995) "Synthetic Human Antibodies", Nat Med., 1(8): 837-839.
Barr et al. (1999) "Subcellular Localization and Internalization of the Four Human Leptin Receptor Isoforms", J Biol Chem., 274(30): 21416-21424.
Barsh & Schwartz (2002) "Genetic Approaches to Studying Energy Balance: Perception and Integration", Nat Rev Genet., 3(8): 589-600.
Bates & Myers (2003) "The Role of Leptin Receptor Signaling in Feeding and Neuroendocrine Function", TRENDS in Endocrinology and Metabolism, 14(10): 447-452.
Bates et al. (2003) "STAT3 Signaling is Required for Leptin Regulation of Energy Balance but not Reproduction", Nature 421: 856-859.
Bendig (1995) "Humanization of Rodent Monoclonal Antibodies by CDR Grafting", Method3: A Companion to Methods in Enzymology, 8: 83-93.
Bingham et al. (2008) "Predictors of Acquired Lipodystrophy in Juvenile-Onset Dermatomyositis and a Gradient of Severity", Medicine (Baltimore), 87(2): 70-86.
Bjornholm et al. (2007) "Mice Lacking Inhibitory Leptin Receptor Signals are Lean with Normal Endocrine Function", J. Clin. Invest., 117: 1354-1360.
Boersma and Pluckthun (2011) "DARPins and Other Repeat Protein Scaffolds: Advances in Engineering and Applications", Curr. Opin. Biotechnol., 22: 849-857.
Bolan et al. (2002) "Intensive, Long-Term Plasma Exchange Therapy for Severe Hypertriglyceridemia in Acquired Generalized Lipoatrophy", J Clin Endocrinol Metab., 87(1): 380-384.
Brennan et al. (1985) "Preparation of Bispecific Antibodies by Chemical Recombination of Monoclonal Immunoglobulin G1 Fragments," Science, 229: 81-83.
Brown et al. (2016) "Lymphoma in Acquired Generalized Lipodystrophy", Leuk Lymphoma, 57(1): 45-50.
Brown et al. (2018) "Long-Term Effectiveness and Safety of Metreleptin in the Treatment of Patients with Generalized Lipodystrophy", Endocrine, 60(3): 479-489.
Bülbül et al. (2001) "Acute Pancreatitis in a Patient with Partial Lipodystrophy and Membranoproliferative Glomerulonephritis", Nephrol Dial Transplant., 16(9): 1930-1931.
Carpenter et al. (1998) "Enhancing Leptin Response by Preventing SH2-containing Phosphate 2 Interaction with Ob Receptor", Proc. Natl. Acad. Sci. USA, 95: 6061-6066.
Carpenter et al. (2000) "Non-Fc Receptor-Binding Humanized Anti-CD3 Antibodies Induce Apoptosis of Activated Human T Cells," J Immunol. 165(11): 6205-16213.
Carter (2001) "Bispecific Human IgG by Design", J Immunol Meth., 248: 7-15.
Casset et al. (2003) "A Peptide Mimetic of an Anti-CD4 Monoclonal Antibody by Rational Design", Biochemical and Biophysical Research Communications, 307: 198-205.
Ceddia (2005) "Direct Metabolic Regulation in Skeletal Muscle and Fat Tissue by Leptin: Implications for Glucose and Fatty Acids Homeostasis", Int J Obes., 29(10): 1175-1183.
Chen et al. (1996) "Evidence That the Diabetes Gene Encodes the Leptin Receptor: Identification of a Mutation in the Leptin Receptor Gene in db/db Mice", Cell, 84(3): 491-495.
Cheung (2014) "A Pegylated Leptin Antagonist Ameliorates CKD-Associated Cachexia in Mice", J Am Soc Nephrol., 25(1): 119-128.
Chothia et al. (1987) "Canonical Structures for the Hypervariable Regions of Immunoglobulins", J. Mol. Biol., 196: 901-917.
Chothia et al. (1989) "Conformations of Immunoglobulin Hypervariable Regions", Nature, 342: 877-883.
Conrath et al. (2001) "Camel Single-Domain Antibodies as Modular Building Units in Bispecific and Bivalent Antibody Constructs", J Biol Chem., 276(10): 7346-7350.
Coppari & Bjørbæk (2012) "The Potential of Leptin for Treating Diabetes and Its Mechanism of Action", Nat Rev Drug Discov., 11(9): 692-708.
Cron et al. (2016) "The Role of gp130 Receptor Cytokines in The Regulation of Metabolic Homeostasis", Journal of Experimental Biology, 219(2): 259-265.
De Bruin et al. (1999) "Selection of High-Affinity Phage Antibodies from Phage Display Libraries", Nat Biotech. 17: 397-399.
Dechiara et al. (2009) "VelociMouse: Fully ES Cell-Derived F0-Generation Mice Obtained from the Injection of ES Cells into Eight-Cell-Stage Embryos", Meth Mol Biol., 530: 311-24.
Dechiara et al. (2010) "Producing Fully ES Cell-Derived Mice from Eight-Cell Stage Embryo Injections", Meth Enzymol., 476: 285-94.
Dembo et al. (1994) "Limit Distribution of Maximal Non-Aligned Two-Sequence Segmental Score", Ann. Prob., 22(4): 2022-2039.
Desmyter et al. (2001) "Antigen Specificity and High Affinity Binding Provided by One Single Loop of a Camel Single-Domain Antibody", J Biol Chem., 276(28): 26285-26290.
Detsky et al. (1987) "What is Subjective Global Assessment of Nutritional Status?" J Parent Enteral Nutr., 11(1): 8-13.
Dewall et al. (2008) "Collective and Individual Functions of Leptin Receptor Modulated Neurons Controlling Metabolism and Ingestion", Endocrinology, 149(4): 1773-1785.
Eldin et al. (2020) "Healthcare Delivery and Education, Expanding Clinical Considerations for Patient Testing and Care—Pain is a Major Driver of Quality of Life and Psychoemotional Health in Lipodystrophy Syndromes", Journal of the Endocrine Society, MON-121, vol. 4, Abstract Supplementation, A571.

(56) References Cited

OTHER PUBLICATIONS

Everts et al. (2002) "Selective Intracellular Delivery of Dexamethasone into Activated Endothelial Cells Using an E-Selection-Directed Immunoconjugate", J Immunol., 168: 883-889.
Fearon et al. (2011) "Definition and Classification of Cancer Cachexia: An International Consensus", Lancet Oncol., 12: 489-495.
Febbraio (2007) "gp130 Receptor Ligands as Potential Therapeutic Targets for Obesity", Journal of Clinical Investigation, 117(4): 841-849.
Ferguson et al. (1999) "Validation of a Malnutrition Screening Tool for Patients Receiving Radiotherapy", Australas Radio., 43: 325-327.
Foote and Winter (1992) "Antibody Framework Residues Affecting the Conformation of the Hypervariable Loops", J Mol Biol., 224: 487-499.
Foss-Freitas, et al. (2020) "Diagnostic Strategies and Clinical Management of Lipodystrophy", Expert Rev Endocrinol Metab, 15(2): 95-114.
Foster, et al. (2003) "Body Weight Regulation by Selective MC4 Receptor Agonists and Antagonists", Ann N.Y. Acad Sci., 994: 103-110.
Franceschini, et al. (1995) "Pre-B Acute Lymphoblastic Leukemia in a Patient with Partial Lipodystrophy and Acanthosis Nigricans", Panminerva Med., 37(4): 248-251.
Garg (2000) "Gender Differences in the Prevalence of Metabolic Complications in Familial Partial Lipodystrophy (Dunnigan Variety)", J Clin Endocrinol Metab., 85(5): 1776-1782.
Ge et al. (2018) "Leptin in Depression: A Potential Therapeutic Agent", Cell Death & Disease, 9(11): 1096, 10 pages.
Gibellini et al. (1998) "Extracellular HIV-1 Tat Protein Induces the Rapid Ser133 Phosphorylation and Activation of CREB Transcription Factor in Both Jurkat Lymphoblastoid T Cells and Primary Peripheral Blood Mononuclear Cells", J Immunol., 160: 3891-3898.
Gish et al. (1993) "Identification of Protein Coding Regions by Database Similarity Search", Nature Genet., 3: 266-272.
Greenfield et al. (2009) "Modulation of Blood Pressure by Central Melanocortinergic Pathways", N Engl J Med., 360: 44-52.
Gromada et al. (2017) "New Isolated Antibody That Binds Human Leptin Receptor (LEPR) and Activates LEPR Signaling Used to Treat Disease Associated with or Caused by Leptin Deficiency or Leptin Resistance e.g. Lipodystrophy, Metabolic Syndrome, and Diabetes", XP55865322, Database Accession No. 2017-288676 Abstract and & US2017/101477 A1, Database WPI [Online Apr. 13, 2017], 3 pages.
Hall et al. (1978) "Generalised Lipodystrophy, Scleroderma, and Hodgkin's Disease", Arch Intern Med., 138(8): 1303-1304.
Hancock et al. (1994) "SIMPLE34: An Improved and Enhanced Implementation for VAX and Sun Computers of the SIMPLE Algorithm for Analysis of Clustered Repetitive Motifs in Nucleotide Sequences", Comput. Appl. Biosci., 10(1): 67-70.
Handelsman et al. (2013) "The Clinical Approach to the Detection of Lipodystrophy—An AACE Consensus Statement", Endocr Pract., 19(1): 107-16.
Haque et al. (2002) "Post-Mortem Findings in Familial Partial Lipodystrophy", Dunnigan Variety. Diabet Med., 19(12): 1022-1025.
He et al. (1998) "Humanization and Pharmacokinetics of a Monoclonal Antibody with Specificity for Both E- and P-Selectin", J Immunol., 160: 1029-1035.
Hegele (2001) "Premature Atherosclerosis Associated with Monogenic Insulin Resistance", Circulation, 103(18): 2225-2229.
Henikoff et al. (1992) "Amino Acid Substitution Matrices from Protein Blocks", Proc. Natl. Acad. Sci. USA, 89: 10915-10919.
Hoogenboom and Chames (2000) "Natural and Designer Binding Sites Made by Phage Display Technology", Immunol Today, 21(8): 371-377.
Hsing and Bishop (1999) "Requirement for Nuclear Factor-kB Activation by a Distinct Subset of CD40-Mediated Effector Functions in B Lymphocytes", J Immunol., 162: 2804-2811.
Hudson and Kortt (1999) "High Avidity scFv Multimers; Diabodies and Triabodies", J Immunol Meth., 231: 177-189.
Hukshorn et al. (2003) "Pegylated Human Recombinant Leptin (PEG-OB) Causes Additional Weight Loss in Severely Energy-Restricted, Overweight Men", Am J Clin Nutr., 77: 771-776.
International Search Report and Written Opinion for PCT/US2019/066908 mailed Mar. 25, 2020.
Janoschek et al. (2006) "gp130 Signaling in Proopiomelanocortin Neurons Mediates the Acute Anorectic Response to Centrally Applied Ciliary Neurotrophic Factor", PNAS, 103(28): 10707-10712.
Javor et al. (2004) "Proteinuric Nephropathy in Acquired and Congenital Generalized Lipodystrophy: Baseline Characteristics and Course During Recombinant Leptin Therapy", J Clin Endocrinol Metab., 89(7): 3199-3207.
Kabat (1978) "The Structural Basis for Antibody Complementary", Adv. Prot. Chem., 32: 1-75.
Kabat et al. (1977) "Unusual Distributions of Amino Acids in Complementarity-Determining (Hypervariable) Segments of Heavy and Light Chains of Immunoglobulins and Their Possible Roles in Specificity of Antibody-Combining Sites", J. Biol. Chem., 252: 6609-6616.
Kaithamana et al. (1999) "Induction of Experimental Autoimmune Graves' Disease in BALB/c Mice", J Immunol., 163: 5157-5164.
Karlin et al. (1990) "Methods for Assessing the Statistical Significance of Molecular Sequence Features by Using General Scoring Schemes", Proc. Natl. Acad. Sci. USA, 87: 2264-2268.
Karlin et al. (1993) "Applications and Statistics for Multiple High-Scoring Segments in Molecular Sequences", Proc. Natl. Acad. Sci. USA, 90: 5873-5877.
Kawahara et al. (2003) "Bypassing Antibiotic Selection: Positive Screening of Genetically Modified Cells with an Antigen-Dependent Proliferation Switch", Nucleic Acids Research, 31(No. 7 e32): 1-8.
Kievet et al. (2013) "Chronic Treatment with a Melanocortin-4 Receptor Agonist Causes Weight Loss, Reduces Insulin Resistance, and Improves Cardiovascular Function in Diet-Induced Obese Rhesus Macaques", Diabetes, 62: 490-497.
Kruizenga et al. (2005) "Development and Validation of a Hospital Screening Tool for Malnutriton: The Short Nutritional Assessment Questionnaire (SNAQ)", Clin Nutr 24: 75-82.
Kruizenga et al. (2010) "The SNAQRC, An Easy Traffic Light System as a First Step in the Recognition of Undernutrition in Residential Care", J Nutr Health Aging, 14(2): 83-89.
Kühnen et al. (2016) "Proopiomelanocortin Deficiency Treated with a Melanocortin-4 Receptor Agonist", N Engl J Med, 375: 240-246.
Kyratsous et al. (2015) "Reply to Dimitrov et al.: VelociSuite Technologies are a Foundation for Rapid Therapeutic Antibody Development", PNAS 112(37): E5116.
Lambert et al. (2001) "Ciliary Neurotrophic Factor Activates Leptin-like Pathways and Reduces Body Fat, Without Cachexia or Rebound Weight Gain, Even in Leptin-Resistant Obesity", PNAS, 98(8): 4652-4657.
Le Doussal et al. (1991) "Enhanced In Vivo Targeting of an Asymmetric Bivalent Hapten to Double-Antigen-Positive Mouse B Cells with Monoclonal Antibody Conjugate Cocktails", J Immunol., 146(1): 169-175.
Liu et al. (2010) "Acute Administration of Leptin Produces Anxiolytic-like Effects: A Comparison with Fluoxetine", Psychopharmacology, Springer, Berlin, DE, 207(4): 535-545.
Lloyd et al. (2009) "Modeling the Human Immune Response: Performance of a 10(11) Human Antibody Repertoire Against a Broad Panel of Therapeutically Relevant Antigens", Protein Engineering & Selection, 22(3): 159-168.
Lüdtke, et al. (2005) "Hepatic Steatosis in Dunnigan-Type Familial Partial Lipodystrophy", Am J Gastroenterol., 100(10): 2218-2224.
Maccallum et al. (1996) "Antibody-Antigen Interactions: Contact Analysis and Binding Site Topography", J. Mol. Biol., 262: 732-745.
Mack et al. (1995) "A Small Bispecific Antibody Construct Expressed as a Functional Single-Chain Molecule with High Tumor Cell Cytotoxicity", Proc Natl Acad Sci., 92: 7021-7025.

(56) References Cited

OTHER PUBLICATIONS

Madden et al. (1996) "Applications of Network BLAST Server", Meth. Enzymol., 266: 131-141.
Malecki et al. (2002) "Molecular Immunolabeling with Recombinant Single-Chain Variable Fragment (scFv) Antibodies Designed with Metal-Binding Domains", Proc Natl Acad Sci., 99(1): 213-218.
Marks & Cone (2001) "Central Melanocortins and The Regulation of Weight During Acute and Chronic Disease", Recent Prog Horm Res., 56: 359-375.
Marsh et al. (1999) "Effects of Neuropeptide Y Deficiency on Hypothalamic Agouti-Related Protein Expression and Responsiveness to Melanocortin Analogues", Brain Research, 848: 66-77.
Marsh et al. (1999) "Response of Melanocortin-4 Receptor-Deficient Mice to Anorectic and Orexigenic Peptides", Nature Genetics, 21: 119-122.
Martin et al. (1991) "Molecular Modeling of Antibody Combining Sites", Methods Enzymol., 203: 121-153.
Mendez et al. (1997) "Functional Transplant of Megabase Human Immunoglobulin Loci Recapitulates Human Antibody Response in Mice", Nat Gen., 15: 146-156.
Menne et al. (2000) "A Comparison of Signal Sequence Prediction Methods Using a Test Set of Signal Peptides", Bioinformatics, 16(8): 741-742.
Meyaard et al. (1997) "LAIR-1, a Novel Inhibitory Receptor Expressed on Human Mononuclear Leukocytes", Immunity, 7: 283-290.
Misra et al. (2003) "Clinical Features and Metabolic Derangements in Acquired Generalized Lipodystrophy: Case Reports and Review of the Literature", Medicine (Baltimore), 82(2): 129-146.
Misra et al. (2004) "Clinical Features and Metabolic and Autoimmune Derangements in Acquired Partial Lipodystrophy: Report of 35 Cases and Review of the Literature", Medicine (Baltimore), 83(1): 18-34.
Mori et al. (2004) "Socs3 Deficiency in the Brain Elevates Leptin Sensitivity and Confers Resistance to Diet-Induced Obesity", Nature Medicine, 10(7): 739-743.
Morris & Rui (2009) "Recent Advances in Understanding Leptin Signaling and Leptin Resistance", Am J Physiol Endocrinol Metab., 297(6): E1247-59.
Morrison (1985) "Transfectomas Provide Novel Chimeric Antibodies", Science 229: 1202-1207.
Murphy et al. (2014) "Mice with Megabase Humanization of their Immunoglobulin Genes Generate Antibodies as Efficiently as Normal Mice", PNAS, 111(14): 5153-5158.
Neelemaat et al. (2008) "Screening Malnutrition in Hospital Outpatients. Can the SNAQ Malnutrition Screening Tool Also be Applied to this Population?" Clin Nutr 27:439-446.
Oral & Chan (2010) "Rationale for Leptin-Replacement Therapy for Severe Lipodystrophy", Endocr Pract., 16(2): 324-333.
Oral et al. (2019) "Long-Term Effectiveness and Safety of Metreleptin in the Treatment of Patients with Partial Lipodystrophy", Endocrine, 64(3): 500-511.
O'Sullivan et al. (2007) "Cytokine Receptor Signaling Through the Jak-Stat-Socs Pathway in Disease," Mol. Immunol., 44(10): 2497-2506.
Ottaway et al. (2015) "Diet-Induced Obese Mice Retain Endogenous Leptin Action", Cell Metabolism, 21:877-882.
Özen, et al.(2020) "Current Diagnosis, Treatment and Clinical Challenges in the Management of Lipodystrophy Syndromes in Children and Young People", J Clin Res Pediatr Endocrinol, 12(1):17-28.
Paul (1993) "Fundamental Immunology", 3rd Edition, Laboratory of Immunology National Institute of Allergy and Infection Diseases National Institutes of Health, pp. 292-295.
PCT International Search Report and Written Opinion for International application No. PCT/US2018/066075 mailed Feb. 25, 2019.
Pearson (2000) "Flexible Sequence Similarity Searching with the FASTA3 Program Package", Methods in Molecular Biology, 132: 185-219.
Pedersen et al. (1992) "Antibody Modeling: Beyond Homology", Immunomethods, 1(2): 126-136.
Powell et al. (2011) "New Drug Targets for the Treatment of Obesity", Clin. Pharmacol. Ther., 90(1): 40-51.
Raso et al. (1997) "Intracellular Targeting with Low pH-Triggered Bispecific Antibodies" J Biol Chem 272(44):27623-27628.
Rebouissou et al. (2009) "Frequent In-Frame Somatic Deletions Activate GP130 in Inflammatory Hepatocellular Tumours," Nature, 457(7226): 200-205.
Reineke (2004) "Antibody Epitope Mapping Ussing Arrays of Synthetic Peptides," Methods Mol. Biol., 248: 443-463.
Rhythm Pharma. Press Release, PRNewswire, Rhythm Presents Cardiovascular Safety Data from Phase 1b/2a Clinical Trials of Setmelanotide in Obesity (Nov. 6, 2015).
Savage et al. (2009) "Complement Abnormalities in Acquired Lipodystrophy Revisited", J Clin Endocrinol Metab., 94(1): 10-16.
Segal et al. (2001) "Introduction: Bispecific Antibodies" J Immunol Meth., 248: 1-6.
Shetty et al. (2011) "Leptin Administration to Overweight and Obese Subjects for Six Months Increases Free Leptin Concentrations but Does not Alter Circulating Hormones of the Thyroid and IGF Axes During Weight Loss Induced by a Mild Hypocaloric Diet", Eur. J Endocrinol., 165(2): 249-254.
Shields et al. (2002) "Lack of Fucose on Human IgG1 N-Linked Oligosaccharide Improves Binding to Human FcγRIII and Antibody-dependent Cellular Toxicity", JBC, 277: 26733-26740.
Smith et al. (1975) "Lipodystrophy, Pancreatitis, and Eosinophilia", Gut., 16(3): 230-234.
States et al. (1991) "Improved Sensitivity of Nucleic Acid Database Searches Using Application-Specific Scoring Matrices", Methods, 3: 66-70.
Stefater et al. (2012) "The Anorectic Effect of CNTF Does Not Require Action in Leptin-Responsive Neurons", Endocrinology, 153(6): 2647-54.
Suthaus et al. (2010) "Forced Homo- and Heterodimerization of all gp 130-type Receptor Complexes Leads to Constitutive Ligand-Independent Signaling and Cytokine-Independent Growth", Mol. Biol. Cell., 1(15): 2797-807.
Taga et al. (1997) "Gp130 and the interleukin-6 family of cytokines", Annu. Rev. Immunol, 15: 797-819.
Tang et al. (1999) "Use of a Peptide Mimotope to Guide the Humanization of MRK-16, and Anti-P-Glycoprotein Monoclonal Antibody", J Biol Chem., 274(39): 27371-27378.
Traunecker et al. (1991) "Bispecific Single Chain Molecules (Janusins) Target Cytotoxic Lymphocytes on HIV Infected Cells", Embo J., 10(12): 3655-3659.
UK Working Party on Acute Pancreatitis (2005) "UK Guidelines for the Management of Acute Pancreatitis", Gut.; 54 (Suppl 3): iii1-iii9.
Vajdos et al. (2002) "Comprehensive Functional Maps of the Antigen-binding Site of an Anti-ErbB2 Antibody Obtained with Shotgun Scanning Mutagenesis", J. Mol. Biol., 320: 415-428.
Van Der Klaauw & Farooqi (2015) "The Hunger Genes: Pathways to Obesity", Cell., 161(1): 119-132.
Van Maldergem et al. (2002) "Genotype-Phenotype Relationships in Berardinelli-Seip Congenital Lipodystrophy", J Med Genet., 39(10): 722-733.
Vaughan et al. (1996) "Human Antibodies with Sub-Nanomolar Affinities Isolated from a Large Non-Immunized Phage Display Library", Nat Biotechnol., 14: 309-314.
Villanueva and Myers (2008) "Leptin Receptor Signaling and the Regulation of Mammalian Physiology", Int J Obes., 32: S8-S12.
Volkel et al. (2001) "Optimized Linker Sequences for the Expression of Monomeric and Dimeric Bispecific Single-Chain Diabodies", Prot Eng. 14(10): 815-823.
Von Heijne (1983) "Patterns of Amino Acids Near Signal-Sequence Cleavage Sites", Eur J Biochem., 133: 17-21.
Von Heijne (1986) "A New Method for Predicting Signal Sequence Cleavage Sites", Nucl Acids Res., 14(11): 4683-4690.
Wikberg & Mutulis (2008) "Targeting Melanocortin Receptors: An Approach to Treat Weight Disorders and Sexual Dysfunction", Nat Rev Drug Discov., 7(4): 307-323.

(56) References Cited

OTHER PUBLICATIONS

Wootton, et al. (1993) "Statistics of Local Complexity in Amino Acid Sequences and Sequence Databases", Comput. Chem., 17:149-163.
Wren et al. (2002) "SIGNAL—Sequence Information and GeNomic AnaLysis", Comp Meth Prog Biomed., 68: 177-181.
Wright et al. (2000) "Lymphoid/Neuronal Cell Surface OX2 Glycoprotein Recognizes a Novel Receptor on Macrophages Implicated in the Control of Their Function", Immunity, 13: 233-242.
Wu et al. (1999) "Humanization of a Murine Monoclonal Antibody by Simultaneous Optimization of Framework and CDR Residues", J. Mol. Biol., 294: 151-162.
Yiannias et al. (2006) "Peripheral T-Cell Lymphoma Presenting as Lipoatrophy and Nodules", Int J Dermatol., 45(12): 1415-1419.
Zabeau et al. (2003) "The Ins and Outs of Leptin Receptor Activation", FEBS Letters, 546: 45-50.
Zabeau et al. (2015) "Leptin: From Structural Insights to the Design of Antagonists", Life Sciences, 140: 49-56.
Zadeh et al. (2013) "The Liver Diseases of Lipodystrophy: The Long-term Effect of Leptin Treatment", J Hepatol., 59(1): 131-137.
Zhang et al. (1994) "Positional Cloning of the Mouse Obese Gene and Its Human Homologue", Nature, 372: 425-432.
Zhang et al. (1997) "PowerBLAST: A New Network BLAST Application for Interactive or Automated Sequence Analysis and Annotation", Genome Res., 7: 649-656.
Zhao et al. (2014) "Leptin and IL-6 Family Cytokines Synergize to Stimulate Müller Glia Reprogramming and Retina Regeneration," Cell Reports, 9(1): 272-284.
Accession No. NP_002294.2.
Accession No. XP_005543194.1.
Ahmann, et al. (2015) "Efficacy and safety of liraglutide versus placebo added to basal insulin analogues (with or without metformin) in patients with type 2 diabetes: a randomized, placebo-controlled trial," Diabetes, Obesity and Metabolism 17(11):1056-1064.
Al-Lazikani et al., (1997) "Standard Conformations for the Canonical Structures of Immunoglobulins", J. Mol. Biol. 273:927-948.
Allison, et al. (2014) "Connecting leptin signaling to biological function," Journal of Endocrinology 223:T25-T35.
Altschul et al. (1990) "Basic Local Alignment Search Tool", J. Mol. Biol. 215:403-410.
Altschul et al. (1997) "Gapped BLAST and PSI-BLAST: a new generation of protein database search programs", Nucleic Acids Res. 25:3389-402.
Al Qaraghuli, et al. (2020) "Antibody-Protein Binding and Conformational Changes: Identifying Allosteric Signaling Pathways to Engineer a Better Effector Response", Nature Scientific Reports, 10:13969.
Bhaskar, et al. (2016) "An Allosteric Antibody to the Leptin Receptor Reduces Body Weight and Reverses the Diabetic Phenotype in the $Lep^{ob}/Lep^{ob}$ Mouse," Obesity 00:(00) 1-8.
Bray and Wadden (2015) "Improving Long-Term Weight Loss Maintenance: Can We Do It?", Obesity 23:2-3.
Carpenter et al. (2012) "Structure of the Human Obesity Receptor Leptin-Binding Domain Reveals the Mechanism of Leptin Antagonism by a Monoclonal Antibody", Structure 20(3):487-497.
Chagnon et al. (2000) "Associations Between the Leptin Receptor Gene and Adiposity in Middle-Aged Caucasian Males from the HERITAGE Family Study", Journal of Clinical Endocrinology & Metabolism 85(1):29-34.
Deddish et al. (1990) "Carboxypeptidase M in Madin-Darby Canine Kidney Cells" J. Biological Chemistry 265(25):15083-15089.
Edwards, et al. (2003) "The Remarkable Flexibility of the Human Antibody Repertoire; Isolation of Over One Thousand Different Antibodies to a Single Protein", BLyS, Journal of Molecular Biology, 334:103-118.
Ehring (1999) "Hydrogen Exchange/Electrospray Ionization Mass Spectrometry Studies of Structural Features of Proteins and Protein/Protein Interactions" Analytical Biochemistry 267(2):252-259.
Engen and Smith (2001) The Basics of Ion Chromatography, Anal. Chem. 73:256A-265A.
Farooqi, et al. (2007) "Clinical and Molecular Genetic Spectrum of Congenital Deficiency of the Leptin Receptor," N. Engl. J. Med. 356:237-247.
Farooqui, et al. (2002) "Beneficial effects of leptin on obesity, T cell hyporesponsiveness, and neuroendocrine/metabolic dysfunction of human congenital leptin deficiency," The Journal of Clinical Investigation 110(8):1093-1103.
Fazeli et al. (2006) "Identification of a monoclonal antibody against the leptin receptor that acts as an antagonist and blocks human monocyte and T cell activation", J. Immunol. Methods 312:190-200.
Friedman (2014) "Leptin at 20: an overview", J. Endocrinol. 223(1):T1-8.
Friedman and Halaas (1998) "Leptin and the regulation of body weight in mammals" Nature 395(6704):763-70.
Garg (2011) "Lipodystrophies: Genetic and Acquired Body Fat Disorders", Journal of Clinical Endocrinology and Metabolism, 96(11):3313-3325.
Goel, et al. (2004) "Plasticity Within The Antigen-Combining Site May Manifest as Molecular Mimicry in the Humoral Immune Response", J. Immunol., 173:7358-7367.
Gonnet et al. (1992) "Exhaustive Matching of the Entire Protein Sequence Database", Science 256: 1443-1445.
Goodson (1984) in Medical Applications of Controlled Release, vol. 2, pp. 115-138.
Gorska, et al. (2010) "Leptin Receptors", European Journal of Medical Research, 15(Supplemental II):50-54.
Haniu, et al. (1998) "Human Leptin Receptor, Determination of Disulfide Structure and N-Glycosylation Sites of the Extracellular Domain" J Biol Chem 273(44): 28691-69.
Halpern, et al. (2010) "Combinations of Drugs in the Treatment of Obesity", Pharmaceuticals, 3:2398-2415.
Iepsen, et al. (2014) "Treatment With a GLP-1 Receptor Agonist Diminishes the Decrease in Free Plasma Leptin During Maintenance of Weight Loss," International Journal of Obesity, 39(5):834-841.
Junghans et al. (1990) "Anti-Tac-H, a Humanized Antibody to the Interleukin 2 Receptor with New Features for Immunotherapy in Malignant and Immune Disorders", Cancer Res. 50:1495-1502.
Justice, et al. (2016) "Using the Mouse to Model Human Disease: Increasing Validity and Reproducibility", Disease, Models & Mechanisms 9:101-103.
Kazane et al., (2012) "Synthesis of Bispecific Antibodies using Genetically Encoded Unnatural Amino Acids", J. Am. Chem. Soc., 134:9918-9921 [Epub: Dec. 4, 2012].
Kazane, et al. (2013) "Self-Assembled Antibody Multimers through Peptide Nucleic Acid Conjugation," Journal of the American Chemical Society, 135(1):340-346.
Khan, et al. (2014) "Adjustable Locks and Flexible Keys: Plasticity of Epitope-Paratope Interactions in Germline Antibodies", J. Immunol. 192:5398-5405.
Klein et al. (2012) "Progress in overcoming the chain association issue in bispecific heterodimeric lgG antibodies", mAbs 4:6, 653-663.
Kufer et al. (2004) "A revival of bispecific antibodies", Trends Biotechnol. 22:239-244.
Langer (1990) "New Methods of Drug Delivery", Science 249:1527-1533.
Li, et al. (2016) "The Role of Leptin in Central Nervous System Diseases", NeuroReport 27(5):350-355.
Lin, et al. (2018) "Leptin signaling axis specifically associates with clinical prognosis and is multifunctional in regulating cancer progression", Oncontarget 9(24):17210-17219.
Mancour, et al. (2012) "Ligand-Induced Architecture of the Leptin Receptor Signaling Complex," Molecular Cell 48:655-661.
Marcic et al. (2000) "Replacement of the Transmembrane Anchor in Angiotensin I-converting Enzyme (ACE) with a Glycosylphosphatidylinositol Tail Affects Activation of the $B_2$ Bradykinin Receptor by ACE Inhibitors", J. Biol Chem. 275(21):16110-8.
Mak, et al. (2014) "Exploiting the therapeutic potential of leptin signaling in cachexia", Current Opinion in Supportive and Palliative Care 8(4):352-357.

(56) References Cited

OTHER PUBLICATIONS

Martin et al., (1989) "Modeling antibody hypervariable loops: A combined algorithm", Proc. Natl. Acad. Sci. USA 86:9268-9272.
Mayo Clinic (2015) "Lipodystrophy Syndromes: New Treatment, Newer Questions", Published online Sep. 1, 2015, 4 pages.
Mazen, et al. (2011) "Homozygosity for a Novel Missense Mutation in the Leptin Receptor Gene (P316T) in two Egyptian Cousins with Severe Early Onset Obesity," Molecular Genetics and Metabolism, 102:461-464.
McMurphy et al., (2014) "The Anti-Tumor Activity of a Neutralizing Nanobody Targeting Leptin Receptor in a Mouse Model of Melanoma", PLOS One (2014) 9(2):e89895.
Meehan, et al. (2016) "Metreleptin for Injection to Treat the Complications of Leptin Efficiency in Patients with Congenital or Acquired Generalized Lipodystrophy," Clinical Pharmacology 9(1):59-68.
Molek, et al. ( 2014) "Screening of synthetic phage display scFv libraries yields competitive ligands of human leptin receptor", Biochemical and Biophysical Research Communications 452(3):479-483.
Moon et al. (2013) "Leptin's Role in Lipodystrophic and Nonlipodystrophic Insulin-Resistant and Diabetic Individuals", Endocrine Reviews, 34(3):377-412.
Mordenti et al. (1991) "Interspecies Scaling of Clearance and Volume of Distribution Data for Five Therapeutic Proteins", Pharmaceut. Res. 8:1351.
Morris, et al. (1996) "Epitope Mapping of Protein Antigens by Competition ELISA", The Protein Protocols Handbook, Humana Press, pp. 595-600.
Osorio (2014) "Leptin and Leptin Receptor Expressions in Prostate Tumors May Predict Disease Aggressiveness?", Acta Cirurgica Brasileira, 29(supl.3), 5pages.
Padlan (1994) "Anatomy of the Antibody Molecule", Molecular Immunology, 31(3):169-217.
Park and Ahima (2014) "Leptin Signaling", F1000Prime Reports, 73(6), 8 pages.
Paz-Filho, et al. (2014) "Leptin treatment: Facts and expectations," Metabolism, pp. 1-11, http://dx.doi.org/10.1016/j.metabol.2014.07.014.
Phillips (2001) "The Challenge of Gene Therapy and DNA Delivery", J. Pharm. Pharmacology 53:1169-1174.
International Search Report and Written Opinion received for PCT/US2017/060690 on Jan. 10, 2018, 17 pages.
PCT International Search Report and Written Opinion received for PCT/US2016/056465, on Jan. 10, 2017.
Pearson (1994) "Using the FASTA Program to Search Protein and DNA Sequence Databases", Methods Mol. Biol. 24: 307-331.
Peelman, et al. (2014) "Insights into signaling assemblies of the leptin receptor," Journal of Endocrinology 223:T9-T23.
Poosarla, et al. (2017) "Computational De Novo Design of Antibodies Binding to a Peptide With High Affinity", Biotechn. Bioeng., 114(6):1331-1342.
Powell et al. (1998) "Compendium of excipients for parenteral formulations" PDA (1998) J. Pharm. Sci. Technol. 52:238-311.
Procaccini, et al. (2015) "Leptin in autoimmune diseases," Metabolism Clinical and Experimental 64:92-104.
Rabia, et al. (2018) "Understanding and Overcoming Trade-Offs Between Antibody Affinity, Specificity, Stability and Solubility," Biochemical Engineer Journal, 137:365-374.
Reddy et al., (2000) "Elimination of Fc Receptor-Dependent Effector Functions of a Modified IgG4 Monoclonal Antibody to Human CD4", J. Immunol. 164:1925-1933.
Rosenbaum, et al. (2002) "Low Dose Leptin Administration Reverse Effects of Sustained Weight-Reduction on Energy Expenditure and Circulating Concentrations of Thyroid Hormones," The Journal of Clinical Endocrinology & Metabolism 87(5):2391-2394.
Rosenbaum, et al. (2005) "Low-dose Leptin Reverses Skeletal Muscle, Autonomic, and Neuroendocrine Adaptations to Maintenance of Reduced Weight" The Journal of Clinical Investigation 115(12):3579-3586.
Sefton (1987) "Implantable Pumps", CRC Crit. Ref. Biomed. Eng. 14:201-240.
Shimomura, et al. (1999) "Leptin Reverses Insulin Resistance and Diabetes Mellitus in Mice with Congenital Lipodystrophy," Nature 401:73-76.
Sinha, et al. (1996) "Evidence of Free and Bound Leptin in Human Circulation," The Journal of Clinical Investigation 98(6):1277-1282.
Sweeney (2002) "Leptin signalling", Cell Signal 14(8):655-663.
Tartaglia et al., (1995) "Identification and Expression Cloning of a Leptin Receptor, OB-R", Cell, 83(7):1263-1271.
Tartaglia (1997) "The Leptin Receptor", J. Biol. Chem 7:272(10):6093-6096.
Taylor et al. (1992) "A transgenic mouse that expresses a diversity of human sequence heavy and light chain immunoglobulins", Nucl. Acids Res. 20:6287-6295.
Tomer (2000) "Characterization of a discontinuous epitope of the human immunodeficiency virus (HIV) core protein p24 by epitope excision and differential chemical modification followed by mass spectrometric peptide mapping analysis", Protein Science 9:487-496.
Tutt et al. (1991) "Trispecific F(ab')$_3$ Derivatives that use Cooperative Signaling via the TCR/CD3 Complex and CD2 to Activate and Redirect Resting Cytotoxic T Cells", J. Immunol. 147:60-69.
University of Utah Healthcare (2014) "Knowing the Difference Between Inherited and Acquired Cancers Can Save Lives", Published online Sep. 5, 2014, 3 pages.
Ussar, et al. (2011) "Receptor Antibodies as Novel Therapeutics for Diabetes," Science Translational Medicine, 3(113):22-24.
Wauman, et al. (2011) "Leptin Receptor Signaling: Pathways to Leptin Resistance", Frontiers in Biosciences 16:2771-2793.
Wu et al. (1987) "Receptor-mediated in Vitro Gene Transformation by a Soluble DNA Carrier System", J. Biol. Chem. 262:4429-4432.
Zabeau et al. (2014) "Antagonizing leptin: current status and future directions" Biol. Chem. 395(5):499-514.
Akinci, et al. (2018) "Update on Therapeutic Options in Lipodystrophy," Current Diabetes Reports 18 :139, pp. 1-12.
Kawaji, et al. (2001) "Anti-leptin Receptor Antibody Mimics the Stimulation of Lipolysis Induced by Leptin in Isolated Mouse Fat Pads", Journal of Lipid Research, 42(10):1671-1677.
Molina, et al. (2014) "Pressure Ulcers—Burns/Annals of Physical Rehavilitation Medicine," Lipoatrophia Semicircularis: A case report Abstract P159-e, 57S : e212-e217.
Nolis (2014) "Exploring the Pathophysicology Behind the More Common Genetic and Acquired Lipodystrophies," Journal of Human Genetics, 59 : 16-23.
Purdham, et al. (2007) "A Neutralizing Leptin Receptor Antibody Mitigates Hypertrophy and Hemodynamic Dysfunction in the Postinfarcted Rat Heart", Am. J. Physiol, Heart Circ. Physiol., 295(1):H441-H446.
Stears, et al. (2014) "Diagnosis and Management of Lipodystrophy: a Practical Update," Clinical Lipidology, 9(2): 235-259.
2008 Guidance Document "Ethical Considerations for Clinical Trials on Medicinal Products Conducted with the Pediatric Population".
Addy et al. (2008) "Safety, Tolerability, Pharmacokinetics, and Pharmacodynamic Properties of Taranabant, a Novel Selective Cannabinoid-1 Receptor Inverse Agonist, for the Treatment of Obesity: Results from a Double-blind, Placebo-controlled, Single Oral Dose Study in Healthy Volunteers," J Clin Pharmacol., 48(4): 418-427.
Aijluni (2017) "Efficacy and Safety of Metreleptin in Patients with Partial Lipodystrophy: Lessons from an Expanded Access Program," Journal of Diabetes & Metabolism, 7(3): 1000659, 7 pages.
Al-Attar et al. (2007) "Quantitative and Qualitative Differences in Subcutaneous Adipose Tissue Stores Across Lipodystrophy Types Shown by Magnetic Resonance Imaging," BMC Med Imaging, 7: 3.
Allen, Loyd V. Jr. Ph.D. "The Art, Science and Technology of Pharmaceutical Compounding," in American Pharmacists Association (Washington, D.C., 1999), Introduction pages xxxii-xxxvii.
Angrisani et al. (2017) "Bariatric Surgery and Endoluminal Procedures: IFSO Worldwide Survey 2014," Obes Surg., 27(9): 2279-2289.

(56) References Cited

OTHER PUBLICATIONS

Aronis et al. (2011) "Preadipocyte Factor-1 Levels Are Higher in Women with Hypothalamic Amenorrhea and Are Associated with Bone Mineral Content and Bone Mineral Density through a Mechanism Independent of Leptin," J. Clin. Endocrinol. Metab., 96(10): E1634-E1639.
Barash et al. (1996) "Leptin Is a Metabolic Signal to the Reproductive System," Endocrinology, 137(7): 3144-3147.
Baumann et al. (1996) "The Full-length Leptin Receptor Has Signaling Capabilities of Interleukin 6-type Cytokine Receptors," Proc Natl Acad Sci USA, 93: 8374-8378.
Boden et al. (1996) "Effect of Fasting on Serum Leptin in Normal Human Subjects," J Clin Endocrinol Metab. 81(9): 3419-3423.
Brown et al. (2016) "The Diagnosis and Management of Lipodystrophy Syndromes: A Multi-Society Practice Guideline," J Clin Endocrinol Metab., 101(12): 4500-4511.
Buettner et al. (2002) "Definition and Characterization of Relative Hypo- and Hyperleptinemia in a Large Caucasian Population," J Endocrinol. 175(3): 745-756.
Burakiewicz et al. (2017) "Quantifying Fat Replacement of Muscle by Quantitative MRI in Muscular Dystrophy," J Neurol., 264(10): 2053-2067.
Campfield et al. (1995) "Recombinant Mouse OB Protein: Evidence for a Peripheral Signal Linking Adiposity and Central Neural Networks," Science, 269:546-549.
Chan et al. (2016) "Immunogenicity Associated with Metreleptin Treatment in Patients with Obesity or Lipodystrophy," Clin Endocrinol., 85(1): 137-149.
Chan et al. (2003) "The Role of Falling Leptin Levels in the Neuroendocrine and Metabolic Adaptation to Short-term Starvation in Healthy Men," J Clin Invest., 111(9): 1409-1421.
Chehab et al. (1996) "Correction of the Sterility Defect in Homozygous Obese Female Mice by Treatment with the Human Recombinant Leptin," Nat Genet., 12: 318-320.
Christiansen et al. (2014) "Increased Bone Mineral Content in Patients with Congenital Generalized Lipodystrophy is Unaffected by Metreleptin Replacement Therapy," Endocrine Reviews. 96th Annual Meeting and Expo of the Endocrine Society, ENDO Chicago, IL, USA., 35(3) Abstract No. OR43-6.
Ciofi et al. (2009) "Brain-endocrine Interactions: A Microvascular Route in the Mediobasal Hypothalamus," Endocrinology, 150: 5509-5519.
Clement et al. (1998) "A Mutation in the Human Leptin Receptor Gene Causes Obesity and Pituitary Dysfunction," Nature, 392(6674): 398-401.
Cohen et al. (2001) "Selective Deletion of Leptin Receptor in Neurons Leads to Obesity," J Clin Invest., 108: 1113-1121.
Considine et al. (1996) "Serum Immunoreactive-Leptin Concentrations in Normal-Weight and Obese Humans," N. Engl. J. Med., 334(5): 292-295.
Coppari et al. (2005) "The Hypothalamic Arcuate Nucleus: A Key Site for Mediating Leptin's Effects on Glucose Homeostasis and Locomotor Activity," Cell Metab., 1: 63-72.
Courteix, et al. (2007) "Preserved Bone Health in Adolescent Elite Rhythmic Gymnasts Despite Hypoleptinemia," Hormone Research, 68: 20-27.
Cowley et al. (2001) "Leptin Activates Anorexigenic POMC Neurons Through a Neural Network in the Arcuate Nucleus," Nature, 411: 480-484.
Dalton et al. (2015) "Preliminary Validation and Principal Components Analysis of the Control of Eating Questionnaire (CoEQ) for the Experience of Food Craving," Eur J Clin Nutr., Nature Publishing Group, 69(12): 1313-1317.
Dardeno et al. (2010) "Leptin in Human Physiology and Therapeutics," Front Neuroendocrinol., 31(3): 377-393.
De Luca et al. (2005) "Complete Rescue of Obesity, Diabetes, and Infertility in db/db Mice by Neuron-specific LEPR-B Transgenes," J Clin Invest., 115: 3484-3493.
Denroche et al. (2013) "Leptin Administration Enhances Islet Transplant Performance in Diabetic Mice," Diabetes 62: 2738-2746.
Dubern et al. (2012) "Leptin and Leptin Receptor-related Monogenic Obesity," Biochimie., 94(10): 2111-2115.
Ducy et al. (2000) "Leptin Inhibits Bone Formation Through a Hypothalamic Relay: A Central Control of Bone Mass," Cell, 100: 197-207.
Ebihara et al. (2007) "Efficacy and Safety of Leptin-Replacement Therapy and Possible Mechanisms of Leptin Actions in Patients with Generalized Lipodystrophy," J Clin Endocrinol Metab., 92(2): 532-541.
El-Zayadi (2008) "Hepatic Steatosis: A Benign Disease or A Silent Killer," World J Gastroenterol., 14(26): 4120-4126.
European Publication Notice received for EP Application No. 21207469.4, dated Sep. 14, 2022, 1 page.
Farooqi et al. (1999) "Effects of Recombinant Leptin Therapy in a Child with Congenital Leptin Deficiency," The New England Journal of Medicine, 341(12): 879-884.
Federico et al. (2006) "Treatment of Patients with Non-alcoholic Fatty Liver Disease: Current Views and Perspectives," Digestive & Liver Disease, 38(11): 789-801.
Feng et al. (2018) "Roles and Mechanisms of Leptin in Osteogenic Stimulation in Cervical Ossification of the Posterior longitudinal Ligament," Journal of Orthopaedic Surgery and Research, 13: 165, 8 pages.
Fenton et al. (2020) "Rheostat Positions: A New Classification of Protein Positions Relevant to Pharmacogenomics Medicinal Chemistry Research," 29: 1133-1146.
Festi et al. (2004) "Hepatic Steatosis in Obese Patients: Clinical Aspects and Prognostic Significance," Obes Rev., 5(1): 27-42.
Flak and Myers (2016) "Minireview: CNS Mechanisms of Leptin Action," Mol Endocrinol., 30: 3-12.
Flegal et al. (2016) "Trends in Obesity Among Adults in the United States, 2005 to 2014," JAMA. American Medical Association, 315(21): 2284-2291.
Flint et al. (2000) "Reproducibility, Power and Validity of Visual Analogue Scales in Assessment of Appetite Sensations in Single Test Meal Studies," Int. J. Obes. Relat. Metab. Disord., 24(1): 38-48.
Funcke et al. (2014) "Monogenic Forms of Childhood Obesity Due to Mutations in the Leptin Gene," Mol Cell Pediatr., 1(1): 3.
Gavrila et al. (2003) "Diurnal and Ultradian Dynamics of Serum Adiponectin in Healthy Men: Comparison with Leptin, Circulating Soluble Leptin Receptor, and Cortisol Patterns," J Clin Endocrinol Metab., 88(6): 2838-2843.
Ghazali et al. (2003) "Bone Mineral Density Directly Correlates with Elevated Serum Leptin in Hemodialysis Patients," Nephrology Dialysis Transplantation, 18: 1882-1890.
Ghorban-Sabbagh et al. (2016) "Correlation Between Serum Leptin and Bone Mineral Density in Hemodialysis Patients," J. Renal Inj. Prev., 5(3): 112-117.
Gibson et al. (2004) "Congenital Leptin Deficiency Due to Homozygosity for the Delta133G Mutation: Report of Another Case and Evaluation of Response to Four Years of Leptin Therapy," J Clin Endocrin. & Metab., 89(10): 4821-4826.
Halaas et al. (1995) "Weight-Reducing Effects of the Plasma Protein Encoded by the Obese Gene," Science, 269: 543-546.
Halaas et al. (1997) "Physiological Response to Long-term Peripheral and Central Leptin Infusion in Lean and Obese Mice," Proc Natl Acad Sci USA., 94: 8878-8883.
Haque et al. (2002) "Serum Adiponectin and Leptin Levels in Patients with Lipodystrophies," The Journal of Clinical Endocrinology and Metabolism, 87(5): 2395-2398.
Harris et al. (1998) "A Leptin Dose-response Study in Obese (ob/ob) and Lean (+/?) Mice," Endocrinology, 139:8-19.
Herrick et al. (2016) "Leptin, Leptin Soluble Receptor, and the Free Leptin Index following a Diet and Physical Activity Lifestyle Intervention in Obese Males and Females," J Obes. Hindawi., 2016(2): 8375828, 5pages.
Heymsfield et al. (1999) "Recombinant Leptin for Weight Loss in Obese and Lean Adults, A Randomized, Controlled, Dose-Escalation Trial," JAMA, 282(16): 1568-1575.

(56) References Cited

OTHER PUBLICATIONS

Hukshorn et al. (2000) "Weekly Subcutaneous Pegylated Recombinant Native Human Leptin (PEG-OB) Administration in Obese Men," J Clin Endocrinol Metab., 85(11): 4003-4009.
Jakubke et al. (1985) "Amino Acids, Peptides, Proteins," M. Mir., pp. 93-94 (English translation of the Russian reference).
Jakubke et al. (1985) "Amino Acids, Peptides, Proteins," M. Mir., pp. 93-94 (Russian reference).
Jing et al. (2016) "Mechanical Vibration Mitigates the Decrease of Bone Quantity and Bone Quality of Leptin Receptor-Deficient Db/Db Mice by Promoting Bone Formation and Inhibiting Bone Resorption," Journal of Bone and Mineral Research, 31(9): 1713-1724.
Klopfenstein et al. (2012) "Comparison of 3 T MRI and CT for the Measurement of Visceral and Subcutaneous Adipose Tissue in Humans," Br J Radiol., 85(1018): e826-30.
Krishna et al. (2009) "Potent and Selective Agonism of the Melanocortin Receptor 4 with MK-0493 Does Not Induce Weight Loss in Obese Human Subjects: Energy Intake Predicts Lack of Weight Loss Efficacy," Clin Pharmacol Ther., 86(6): 659-66.
Lammert et al. (2001) "Soluble Leptin Receptor Represents the Main Leptin Binding Activity in Human Blood," Biochem Biophys Res Commun., 283(4): 982-988.
Licinio et al. (2004) "Phenotypic Effects of Leptin Replacement on Morbid Obesity, Diabetes Mellitus, Hypogonadism, and Behavior in Leptin-Deficient Adults," Proc Natl Acad Sci USA., 101(13): 4531-4536.
Lou et al. (2010) "Reduced Body Weight and Increased Energy Expenditure in Transgenic Mice Over-Expressing Soluble Leptin Receptor," PLoS One 5(7): e11669.
Mantzoros et al. (2011) "Leptin in Human Physiology and Pathophysiology," Am J. Physiol. Endocrinol. Metab., 301(4): E567-584.
Mashkovsky (2012) "Drugs," 16th ed., revised, corrected and supplemented, M.: New Wave pp. 12-13 (English translation of the Russian reference).
Mashkovsky (2012) "Drugs," 16th ed., revised, corrected and supplemented, M.: New Wave pp. 12-13 (Russian reference).
McDuffie et al. (2004) "Effects of Exogenous Leptin on Satiety and Satiation in Patients with Lipodystrophy and Leptin Insufficiency," J. Clin. Endocrinol. Metab., 89(9): 4258-4263.
Minicocci et al. (2012) "Mutations in the ANGPTL3 Gene and Familial Combined Hypolipidemia: A Clinical and Biochemical Characterization," J Clin Endocrinol Metab., 97(7): E1266-1275.
Mironov et al. (2012) "Guidelines for Conducting Preclinical Studies of Drugs, Part One," M.: Grif and K, pp. 858-860, table 2 (English translation of the Russian reference).
Mironov et al. (2012) "Guidelines for Conducting Preclinical Studies of Drugs, Part One," M.: Grif and K, pp. 858-860, table 2 (Russian reference).
Montague et al. (1997) "Congenital Leptin Deficiency is Associated with Severe Early-onset Obesity in Humans," Nature, 387(6636): 903-908.
Mould and Green (2010) "Pharmacokinetics and Pharmacodynamics of Monoclonal Antibodies," BioDrugs, 24(1): 29-39.
Muniyappa et al. (2017) "Metreleptin Therapy Lowers Plasma Angiopoietin-like Protein 3 in Patients with Generalized Lipodystrophy," Journal of Clin Lipidol., 11(2): 543-550.
Muzzin et al. (1996) "Correction of Obesity and Diabetes in Genetically Obese Mice by Leptin Gene Therapy," Proc Natl Acad Sci USA., 93: 14804-14808.
Ng et al. (2014) "Global, Regional, and National Prevalence of Overweight and Obesity in Children and Adults During 1980-2013: A Systematic Analysis for the Global Burden of Disease Study 2013," Lancet 384(9945): 766-781.
Nidhina Haridas (2015) "Regulation of Angiopoietin-Like Proteins (ANGPTLs) 3 and 8 by Insulin," J Clin Endocrinol Metab., 100(10): E1299-1307.
Norsted et al. (2008) "Protein Components of the Blood-brain Barrier (BBB) in the Mediobasal Hypothalamus," Journal of Chemical Neuroanatomy, 36: 107-121.
Oral et al. (2002) "Leptin-Replacement Therapy for Lipodystrophy," N Engl J Med., 346(8): 570-578.
Oral, E., "Clinical Protocol to Investigate the Efficacy of Recombinant Human Leptin (Metreleptin) in Nonalcoholic Steatohepatitis (NASH) or Nonalcoholic Fatty Liver Disease (NAFLD) Associated with Lipodystrophy," University of Michigan, Oct. 8, 2012, 12 pages, [online]: U.S. National Library of Medicine, retrieved on Oct. 7, 2019, ClinicalTrials.gov Identified NCT01679197.
Oral, E., "Clinical Protocol to Investigate the Long-term Safety and Efficacy of Metreleptin in Various Forms of Partial Lipodystrophy," University of Michigan, Sep. 29, 2015, 8 pages, [online] U.S. National Library of Medicine, retrieved on Oct. 28, 2021, ClinicalTrials.gov Identifier: NCT02654977.
Özsu, et al. (2017) "Early-onset Severe Obesity Due to Complete Deletion of the Leptin Gene in a Boy," J Pediatr Endocrinol Metab., 30(11): 1227-1230.
Patni and Garg (2015) "Congenital Generalized Lipodystrophies—New Insights into Metabolic Dysfunction," Nat Rev Endocrinol., 11: 522-534.
Paz-Filho et al. (2011) "Ten Years of Leptin Replacement Therapy," Obesity Reviews, 12: e315-e323.
PCT International Search Report from PCT/US2019/026173 dated Jul. 30, 2019, 15 pages.
Pelleymounter et al. (1995) "Effects of the obese Gene Product on Body Weight Regulation in ob/ob Mice," Science, 269: 540-543.
Ravussin et al. (2009) "Enhanced Weight Loss with Pramlintide/Metreleptin: An Integrated Neurohormonal Approach to Obesity Pharmacotherapy," Obesity, 17(9): 1736-1743.
Ravussin et al. (2014) "A Missing Link in Bodyweight Homeostasis: The Catabolic Signal of the Overfed State," Cell Metab., 20(4): 565-572.
Roemmich et al. (2003) "Relationship of Leptin to Bone Mineralization in Children and Adolescents," J. Clin. Endocrinol. Metab., 88(2): 599-604.
Ruhl and Everhart (2001) "Leptin Concentrations in the United States: Relations with Demographic and Anthropometric Measures," Am J Clin Nutr., 74(3): 295-301.
Schoeller et al. (1997) "Entrainment of the Diurnal Rhythm of Plasma Leptin to Meal Timing," J Clin Invest., 100(7): 1882-1887.
Schurgin et al. (2004) "Endocrine and Metabolic Effects of Physiologic r-metHuLeptin Administration during Acute Caloric Deprivation in Normal-Weight Women," J Clin Endocrinol Metab., 89(11): 5402-5409.
Selezneva et al. (2015) "Complex Approach to Study Pharmacological Agents In Vitro, Ex Vivo, In Vivo," International Research Journal, 6(37): 125-127 In Russian with English Abstract.
Shimomura et al. (1998) "Insulin Resistance and Diabetes Mellitus in Transgenic Mice Expressing Nuclear SREBP-1c in Adipose Tissue: Model for Congenital Generalized Lipodystrophy," Genes Dev., 12: 3182-3194.
Sienkiewicz et al. (2011) "Long-term Metreleptin Treatment Increases Bone Mineral Density and Content at the Lumbar Spine of Lean Hypoleptinemic Women," Metabolism Clinical and Experimental, 60: 1211-1221.
Simha (2014) "Metreleptin for Metabolic Disorders Associated with Generalized or Partial Lipodystrophy," Expert Rev. Endocrinol. Metab., 9(3): 205-212.
Simha et al. (2002) "Effect of Subcutaneous Leptin Replacement Therapy on Bone Metabolism in Patients with Generalized Lipodystrophy," The Journal of Clinical Endocrinology and Metabolism, 87(11): 4942-4945.
Sjöström (1998) "Randomised Placebo-controlled Trial of Orlistat for Weight Loss and Prevention of Weight Regain in Obese Patients," Lancet 352(9123): 167-172.
Smith et al. (2010) "Multicenter, Placebo-Controlled Trial of Lorcaserin for Weight Management," N. Engl. J. Med., 363(3): 245-256.
Stoner "Setemelanotide in a Single Patient with Partial Lipodystrophy," Rhythm Pharmaceuticals, Inc., Ann Arbor, MI, Aug. 25, 2017, 5 pages, [online] U.S. National Library of Medicine, retrieved on Sep. 10, 2019, ClinicalTrials.gov Identifier: NCT03262610.
Tartaglia et al. (1996) "The Full-length Leptin Receptor Has Signaling Capabilities of Interleukin 6-type Cytokine Receptors," Proc Natl Acad Sci USA., 93: 8374-8378.

(56) References Cited

OTHER PUBLICATIONS

Tikka (2016) "The Role of ANGPTL3 in Controlling Lipoprotein Metabolism," Endocrine, 52(2): 187-193.
Tokuriki et al. (2009) "Stability Effects of Mutations and Protein Evolvability," Current Opinion Struc. Biol., 19: 596-604.
"Trial of Leptin Replacement Therapy in Patients with Lipodystrophy" [online] Mar. 11, 2009 (retrieved on Aug. 4, 2021), Retrieved from ClinicalTrials.gov, Identifier: NCT00896298 (Year:2009).
Tyagi and Gupta (1998) "Chemical Modification and Chemical Crosslinking for Protein/Enzyme Stabilization," Biochemistry, 63(3): 395-407 (English Abstract).
Tyagi and Gupta (1998) "Chemical Modification and Chemical Crosslinking for Protein/Enzyme Stabilization," Biochemistry, 63(3): 395-407 (Russian reference).
Upadhyay (2015) "The Role of Leptin in Regulating Bone Metabolism," Metabolism, 64(1): 105-113.
Valenzuela et al. (2003) "High-throughput Engineering of the Mouse Genome Coupled with High-Resolution Expression Analysis," Nature Biotechnology, 21(6): 652-659.
Van Dielen et al. (2002) "Leptin and Soluble Leptin Receptor Levels in Obese and Weight-Losing Individuals," J Clin Endocrinol Metab., 87(4): 1708-1716.
Wabitsch et al. (2015) "Severe Early-Onset Obesity Due to Bioinactive Leptin Caused by a p.N103K Mutation in the Leptin Gene," J Clin Endocrinol Metab., 100(9): 3227-3230).
Warren et al. (1999) "Functional Hypothalamic Amenorrhea: Hypoleptinemia and Disordered Eating," The Journal of Clinical Endocrinology & Metabolism, 84(3): 873-877.
Welt et al. (2004) "Recombinant Human Leptin in Women with Hypothalamic Amenorrhea," N. Engl. J. Med., 351: 987-997.
White and Tartaglia (1996) "Leptin and OB-R: Body Weight Regulation by a Cytokine Receptor," Cytokine & Growth Factor Reviews 7(4): 303-309.
Yadav and Pitchumoni (2003) "Issues in Hyperlipidemic Pancreatitis," J Clinical Gastroenterol., 36(1): 54-62.
Zhang et al. (2016) "Characteristics of Patients Potentially Eligible for Pharmacotherapy for Weight Loss in Primary Care Practice in the United States," Obes Sci Pract., 2(2): 104-114.
Zuchero et al. (2016) "Discovery of Novel Blood-Brain Barrier Targets to Enhance Brain Uptake of Therapeutic Antibodies," Neuron, 89: 70-82.
Lu et al. (2005) "Leptin: A Potential Novel Antidepressant", PNAS, 103(5): 1593-1596.
Wang et al. (2009) "Leptin Replacement Restores Supraspinal Cholinergic Antinociception in Leptin-Deficient Obese Mice", The Journal of Pain, 10(8): 836-843.
Yue et al. (2016) "Leptin Receptor Promotes Adipogenesis and Reduces Osteogenesis by Regulating Mesenchymal Stromal Cells in Adult Bone Marrow," Cell Stem Cell, 18(6): 782-796.
Park et al. (2007) "Long-Term Efficacy of Leptin Replacement in Patients with Dunningan-Type Familial Partial Lipodystrophy," Metabolism Clinical and Experimental, 56:508-516.

* cited by examiner

* $P<0.05$ Isotype Control vs H4H17322P2
@$P<0.05$ Isotype Control vs H4H18457P2
#$P<0.05$ Isotype Control vs H4H18464P2

* $P<0.05$ Isotype Control vs H4H17322P2
@$P<0.05$ Isotype Control vs H4H18457P2
#$P<0.05$ Isotype Control vs H4H18464P2

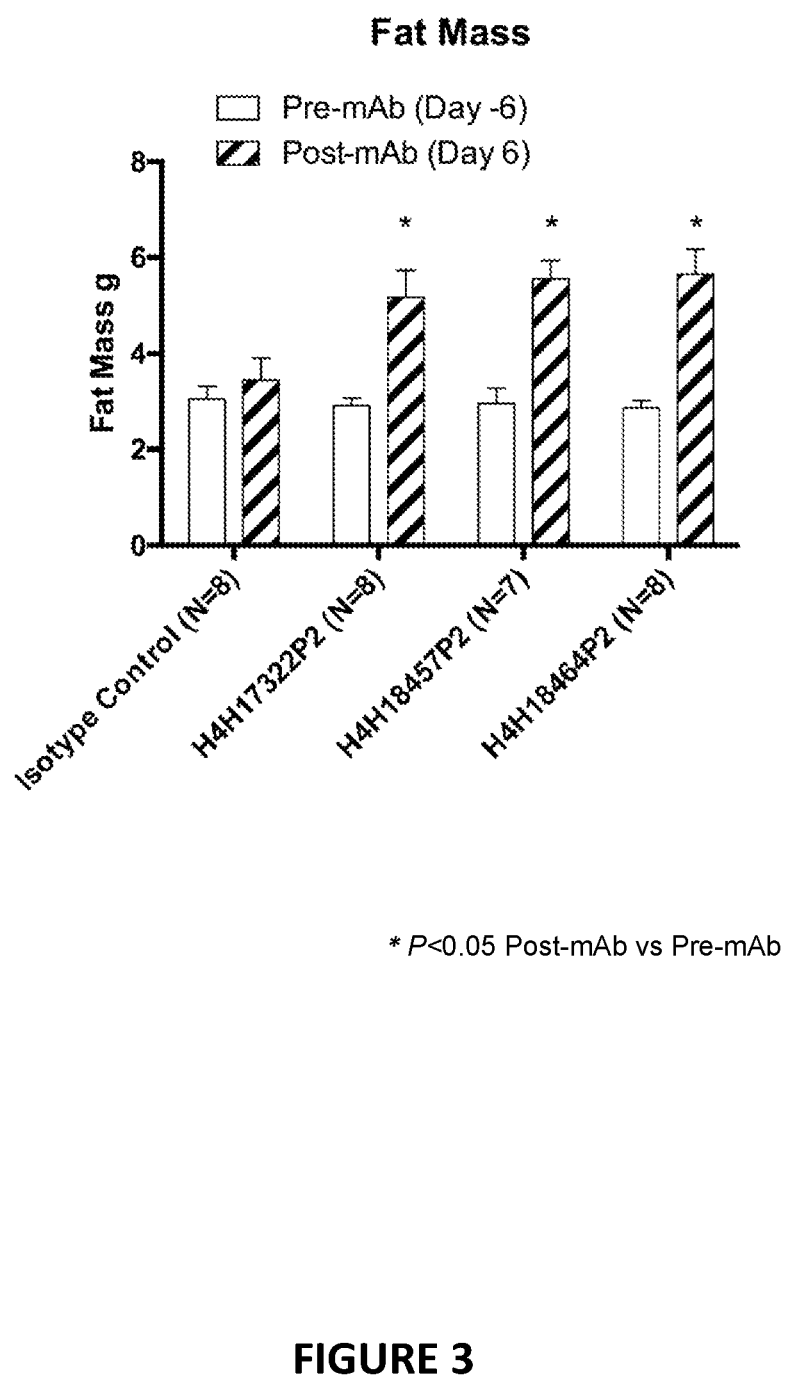

Fat Mass

Pre-mAb (Day -6)
Post-mAb (Day 6)

Fat Mass g 8
6
4
2
0

*
*
*

Isotype Control (N=8)
H4H17322P2 (N=8)
H4H18457P2 (N=7)
H4H18464P2 (N=8)

* *P*<0.05 Post-mAb vs Pre-mAb

FIGURE 3

MONOSPECIFIC ANTIBODIES THAT ANTAGONIZE LEPTIN RECEPTOR

CROSS-REFERENCE TO RELATED APPLICATIONS

This application is a continuation of U.S. patent application Ser. No. 16/736,760, filed Jan. 7, 2020, which is a divisional of U.S. patent application Ser. No. 15/807,426, filed on Nov. 8, 2017, now U.S. Pat. No. 10,550,192, which claims the benefit under 34 U.S.C § 119(e) of U.S. Provisional Application No. 62/419,062, filed Nov. 8, 2016, which is herein specifically incorporated by reference in its entirety.

SEQUENCE LISTING

An official copy of the sequence listing is submitted concurrently with the specification electronically via Patent Center as an XML formatted sequence. The contents of the electronic sequence listing (10271U503 Sequence Listing ST26.xml; Size 131,072 bytes; and Date of Creation: Nov. 16, 2022) is herein incorporated by reference in its entirety.

BACKGROUND

Leptin is a polypeptide hormone predominantly expressed by adipose tissue and is involved in the regulation of metabolism, energy balance and food intake. Leptin activity is mediated by interaction with, and signaling through, the leptin receptor. Leptin receptor, (also known as "LEPR," "WSX," "OB receptor," "OB-R," and "CD295") is a single-pass transmembrane receptor of the class I cytokine receptor family with a large (818 amino acid) extracellular domain. Elevated expression of leptin, the Ob-R leptin receptor or both can contribute to multiple disorders including, but not limited to, anorexia or other psychiatric eating disorders, chronic kidney disease cachexia, other cachexias such as congestive heart failure cachexia, pulmonary cachexia, radiation cachexia, and cancer cachexia, autoimmune disorders such as inflammatory bowel disease, lupus erythematosus, multiple sclerosis, psoriasis, cardiovascular diseases, elevated blood pressure, depression, nonalcoholic fatty liver disease, neurodegenerative disorders, depression, cancer such as hepatocellular carcinoma, melanoma and breast cancer.

Proposed therapeutic approaches for addressing high leptin signaling include use of leptin receptor peptide antagonists and antagonist mutants such as soluble leptin receptor variants, competitive LEPR antagonists such as antibody 9F8 (Fazeli et al. (2006) J Immunological Methods 312, 190-200) or nanobodies targeting leptin receptor (McMurphy et al., PLOS One (2014) 9(2):e89895), fibronectin III domains, orexigenic substances (e.g., ghrelin and NPY), blockade of leptin's downstream mediators (e.g., melanocortin receptor 4) and/or lifestyle changes. Such approaches, however, have generally shown limited efficacy. Thus, a need exists in the art for alternative approaches to treating leptin resistance and other conditions associated with elevated serum leptin levels, and/or excessive LEPR signaling.

BRIEF SUMMARY

The present invention provides antibodies and antigen-binding fragments thereof that bind human leptin receptor (LEPR). The antibodies of the present invention are antagonist antibodies; i.e., binding of the anti-LEPR antibodies of the invention to LEPR result in blockade or down-regulation of leptin receptor signaling in cells. Accordingly, in various embodiments, the antagonist antibodies of the present invention exhibit weak partial agonist activity. Instead, the antibodies of the present invention are useful, e.g., for down-regulating the biological activity of leptin in a subject. The antibodies and antigen-binding fragments of the present invention are therefore useful in the therapeutic treatment of diseases and disorders associated with elevated leptin signaling.

The antibodies of the invention can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al., 2000, *J. Immunol.* 164:1925-1933).

Exemplary LEPR antagonist antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary LEPR antagonist antibodies. Table 2 sets forth the nucleic acid sequence identifiers of the HCVRs, LCVRs, HCDR1, HCDR2 HCDR3, LCDR1, LCDR2 and LCDR3 of the exemplary LEPR antagonist antibodies.

The present invention provides antibodies or antigen-binding fragments thereof that specifically bind LEPR, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-LEPR antibodies listed in Table 1. In certain embodiments, the HCVR/LCVR amino acid sequence pair is selected from the group consisting of SEQ ID NOs: 2/10, 18/10, 26/10, 34/10, 42/10, 50/10, 58/10, 66/10, and 74/82.

The present invention also provides antibodies or antigen-binding fragments thereof that specifically bind LEPR, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-LEPR antibodies listed in Table 1. In certain embodiments, the HCDR3/LCDR3 amino acid sequence pair is selected from the group consisting of SEQ ID NOs: 8/16, 24/16, 32/16, 40/16, 48/16, 56/16, 64/16, 72/16, 80/16 and 80/88.

The present invention also provides antibodies or antigen-binding fragments thereof that specifically bind LEPR, comprising a set of six CDRs (i.e., HCDR1, HCDR2, HCDR3, LCDR1, LCDR2, and LCDR3) contained within any of the exemplary anti-LEPR antibodies listed in Table 1. In certain embodiments, the HCDR1, HCDR2, HCDR3, LCDR1, LCDR2, and LCDR3 amino acid sequences set is selected from the group consisting of SEQ ID NOs: 4, 6, 8, 12, 14, 16; 20, 22, 24, 12, 14, 16; 28, 30, 32, 12, 14, 16; 36, 38, 40, 12, 14, 16; 52, 54, 56, 12, 14, 16; 60, 62, 64, 12, 14, 16; 68, 70, 72, 12, 14, 16; and 76, 78, 80, 84, 86, 88.

In a related embodiment, the present invention provides antibodies, or antigen-binding fragments thereof that specifically bind LEPR, comprising a set of six CDRs (i.e., HCDR1, HCDR2, HCDR3, LCDR1, LCDR2, and LCDR3) contained within an HCVR/LCVR amino acid sequence pair as defined by any of the exemplary anti-LEPR antibodies listed in Table 1. For example, the present invention includes antibodies or antigen-binding fragments thereof that specifically bind LEPR, comprising the HCDR1, HCDR2, HCDR3, LCDR1, LCDR2, and LCDR3 amino acid sequences set contained within an HCVR/LCVR amino acid sequence pair selected from the group consisting of SEQ ID NOs: 2/10, 18/10, 26/10, 34/10, 42/10, 50/10, 58/10, 66/10, and 74/82. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-LEPR antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-LEPR antibodies listed in Table 1.

The present invention also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-LEPR antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-LEPR antibody listed in Table 1.

The present invention also provides recombinant expression vectors capable of expressing a polypeptide comprising a heavy or light chain variable region of an anti-LEPR antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, the invention provides a pharmaceutical composition comprising a recombinant human antibody or fragment thereof which specifically binds LEPR and a pharmaceutically acceptable carrier. In a related aspect, the invention features a composition which is a combination of an anti-LEPR antibody and a second therapeutic agent. In one embodiment, the second therapeutic agent is any agent that is advantageously combined with an anti-LEPR antibody.

In yet another aspect, the invention provides therapeutic methods for down-regulating or abolishing LEPR signaling using an anti-LEPR antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by down-regulating or abolishing LEPR signaling, or by blocking the activity of leptin.

Other embodiments will become apparent from a review of the ensuing detailed description.

BRIEF DESCRIPTION OF THE FIGURES

FIG. 3 shows the average fat mass of mice treated with 30 mg/kg of anti-LEPR antibodies H4H17322P2, H4H18457P2, or H4H18464, or with an isotope control antibody.

DETAILED DESCRIPTION

Figure 1:
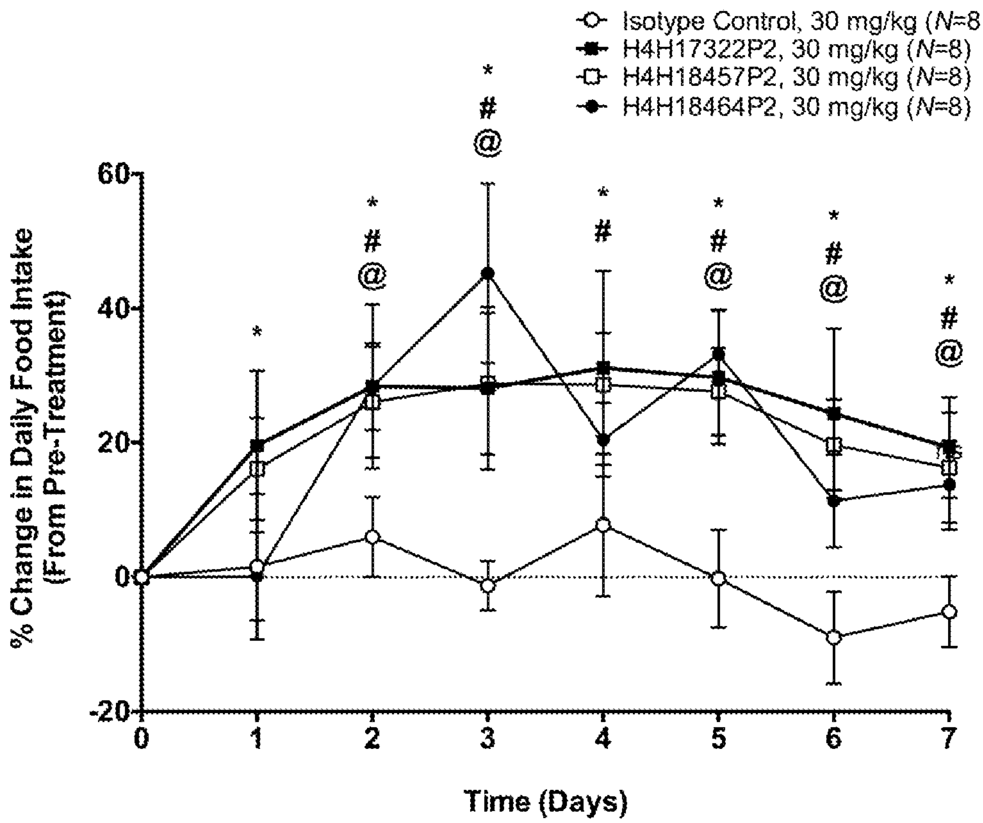
FIG. 1 shows the percent change in food intake of mice treated with 30 mg/kg of anti-LEPR antibodies H4H17322P2, H4H18457P2, or H4H18464, or with an isotope control antibody.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "leptin receptor," "LEPR," and the like, as used herein, refers to the human leptin receptor, comprising the amino acid sequence as set forth in SEQ ID NO: 89 (see also UniProtKB/Swiss-Prot Accession No. P48357). Alternative names for LEPR used in the scientific literature include "OB receptor," "OB-R," and "CD295." LEPR is also referred to as "WSX" (see, e.g., U.S. Pat. No. 7,524, 937). The expression "LEPR" includes both monomeric and multimeric (e.g., dimeric) LEPR molecules. As used herein, the expression "monomeric human LEPR" means a LEPR protein or portion thereof that does not contain or possess any multimerizing domains and that exists under normal conditions as a single LEPR molecule without a direct physical connection to another LEPR molecule. An exemplary monomeric LEPR molecule is the molecule referred to herein as "hLEPR.mmh" comprising the amino acid sequence of SEQ ID NO:90 (see, e.g., Example 3, herein). As used herein, the expression "dimeric human LEPR" means a construct comprising two LEPR molecules connected to one another through a linker, covalent bond, non-covalent bond, or through a multimerizing domain such as an antibody Fc domain. An exemplary dimeric LEPR molecule is the molecule referred to herein as "hLEPR.mFc" comprising the amino acid sequence of SEQ ID NO:91 (see, e.g., Example 3, herein), or the molecule referred to herein as "hLEPR.hFc" comprising the amino acid sequence of SEQ ID NO:92. As used herein, expressions such "anti-LEPR antibody," "antibody that specifically binds LEPR," "LEPR-specific binding protein," and the like, unless specifically indicated otherwise, refer to molecules that bind full length human LEPR, monomeric human LEPR, dimeric human LEPR, or other constructs that comprise or consist of the LEPR extracellular domain.

All references to proteins, polypeptides and protein fragments herein are intended to refer to the human version of the respective protein, polypeptide or protein fragment unless explicitly specified as being from a non-human species. Thus, the expression "LEPR" means human LEPR unless specified as being from a non-human species, e.g., "mouse LEPR," "monkey LEPR," etc.

As used herein, the expression "cell surface-expressed LEPR" means one or more LEPR protein(s), or the extracellular domain thereof, that is/are expressed on the surface of a cell in vitro or in vivo, such that at least a portion of a LEPR protein is exposed to the extracellular side of the cell membrane and is accessible to an antigen-binding portion of an antibody. A "cell surface-expressed LEPR" can comprise or consist of a LEPR protein expressed on the surface of a cell which normally (e.g., in the native or wild-type state) expresses LEPR protein. Alternatively, "cell surface-expressed LEPR" can comprise or consist of LEPR protein expressed on the surface of a cell that normally does not express human LEPR on its surface but has been artificially engineered to express LEPR on its surface.

As used herein, the expressions such as "anti-LEPR antibody," or "antibody that binds human leptin receptor," include both monovalent antibodies with a single specificity, as well as bispecific antibodies comprising a first arm that binds LEPR and a second arm that binds a second (target) antigen, wherein the anti-LEPR arm comprises any of the HCVR/LCVR or CDR sequences as set forth in Table 1 herein.

The term "antibody", as used herein, means any antigen-binding molecule or molecular complex comprising at least one complementarity determining region (CDR) that specifically binds to or interacts with a particular antigen (e.g., LEPR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region.

The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-LEPR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments of the invention, the anti-LEPR antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention encompasses antibodies having one or more mutations in the hinge, $C_H$2 or $C_H$3 region, which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes variants of the anti-LEPR antibodies disclosed herein comprising one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-LEPR antibodies comprising variants of any of the HCVR, LCVR, and/or CDR amino acid sequences disclosed herein having one or more conservative substitutions. For example, the present invention includes anti-LEPR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein. In certain embodiments, the present invention provides anti-LEPR antibodies comprising variant HCVR, LCVR and/or CDR amino acid sequences relative to the sequences set forth in Table 1 herein (e.g., comprising conservative amino acid substitutions), wherein such variant antibodies nonetheless exhibit one or more functions and/or properties of the exemplary anti-LEPR antibodies disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The present invention includes anti-LEPR antibodies and antigen-binding fragments thereof that comprise amino acid sequences that are substantially similar or substantially identical to one or more variable domain or CDR amino acid sequences as found in any of the exemplary anti-LEPR antibodies disclosed herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402, each herein incorporated by reference.

Anti-LEPR Antibodies Comprising Fc Variants

According to certain embodiments of the present invention, anti-LEPR antibodies are provided comprising an Fc domain comprising one or more mutations which enhance or diminish antibody binding to the FcRn receptor, e.g., at acidic pH as compared to neutral pH. For example, the present invention includes anti-LEPR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-LEPR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

The anti-LEPR antibodies of the present invention may comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Biological Characteristics of the Antibodies

The present invention includes antibodies and antigen-binding fragments thereof that bind human LEPR and antagonize LEPR signaling. Such antibodies may be referred to herein as "antagonist antibodies." In the context of the present invention, an "antagonist of LEPR signaling" means an antibody or fragment thereof that binds to LEPR and inhibits an intracellular effect that normally results from the interaction of leptin with LEPR in cells that express LEPR. In various embodiments, the antagonist antibodies of the invention inhibit the function of LEPR agonists, and/or the function of LEPR partial agonists. In certain embodiments, "antagonizing LEPR signaling" means inhibition of leptin-stimulated transcriptional activation of STAT3, which can be detected using any method that can measure or identify, directly or indirectly, STAT3 activity, e.g., using a labeled version of STAT3 expressed in a reporter cell line. For example, the present invention includes antagonist antibodies and antigen-binding fragments thereof that down-regulate LEPR signaling in a cell-based reporter assay as described in Example 6, or a substantially similar assay. The present invention also includes antagonist antibodies and antigen-binding fragments thereof that demonstrate complete inhibition of leptin induced LEPR signaling with $IC_{50}$ values ranging from 723 pM to 1.8 nM in the assay of Example 6, or a substantially similar assay. Cell-based binding assays that detect antibody binding to cells expressing LEPR such as the assay described in Example 5 herein, demonstrated binding to HEK293/hLEPR-GPI cells with binding ratios of 824- to 3187-fold without Leptin and of 398- to 3106-fold in the presence of 1 μM Leptin. Antibodies of the invention were found to bind LEPR even in the presence of excess leptin at 1 μM, indicating that the LEPR antibodies of the invention bind to sites on hLEPR that do not overlap with Leptin binding sites. The invention also includes anti-LEPR antibodies that antagonize leptin signaling but also promote partial LEPR signaling in the absence of leptin; such antibodies are also referred to herein as "partial agonists" or "antibodies that exhibit agonism of LEPR signaling."

In certain exemplary embodiments of the present invention, anti-LEPR antibodies are provided that bind human dimeric LEPR (hLEPR.hFc, SEQ ID NO:92) in the presence or absence of leptin, with none of the antibodies of the invention demonstrating greater than 40% blockade of the LEPR:leptin interaction, e.g., using an assay format as defined in Example 4 herein, or a substantially similar assay.

The present invention includes antibodies and antigen-binding fragments thereof that bind monomeric human LEPR with high affinity. For example, the present invention includes anti-LEPR antibodies that bind monomeric human LEPR (e.g., hLEPR.mmh, SEQ ID NO:90) with a $K_D$ of less than about 10 nM as measured by surface plasmon resonance at 25° C., or less than about 25 nM as measured by surface plasmon resonance at 37° C., e.g., using an assay format as defined in Example 3 herein, or a substantially similar assay. According to certain embodiments, anti-LEPR antibodies are provided that bind monomeric human LEPR at 25° C. with a $K_D$ of less than about 12 nM, less than about 11 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM or less than about 100 pM as measured by surface plasmon resonance, e.g., using an assay format as defined in Example 3 herein, or a substantially similar assay.

The present invention also includes antibodies and antigen-binding fragments thereof that bind monomeric human LEPR (e.g., hLEPR.mmh, SEQ ID NO:90) with a dissociative half-life (t½) of greater than about 5 minutes as measured by surface plasmon resonance at 25° C. or greater than about 1 minute as measured by surface plasmon resonance at 37° C., e.g., using an assay format as defined in Example 3 herein, or a substantially similar assay. According to certain embodiments, anti-LEPR antibodies are provided that bind monomeric human LEPR at 25° C. with a t½ of greater than about 5 minutes, greater than about 10 minutes, greater than about 20 minutes, greater than about 40 minutes, greater than about 50 minutes or longer, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:91) with high affinity. For example, the present invention includes anti-LEPR antibodies that bind dimeric human LEPR (e.g., hLEPR.mFc, SEQ ID NO:91) with a $K_D$ of less than about 4 nM as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a $K_D$ of less than about 15 nM, less than about 10 nM, less than about 9.0 nM, less than about 8.0 nM, less than about 7.0 nM, less than about 6.0 nM, less than about 5.0 nM, less than about 4.0 nM, less than about 3.0 nM, less than about 2.0 nM, less than about 1.0 nM, less than about 900 pM, less than about 800 pM, less than about 700 pM, less than about 600 pM, less than about 500 pM, less than about 400 pM, less than about 300 pM, less than about 200 pM, or less than about 100 pM, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:91) with a dissociative half-life (t½) of greater than about 10 minutes as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a t½ of greater than about 15 minutes, about 20 minutes, greater than about 30 minutes, greater than about 40 minutes, greater than 50 minutes, greater than about 60 minutes, greater than about 70 minutes, greater than 80 minutes, greater than 90 minutes, greater than 100 minutes, or longer, as measured by surface plasmon resonance, e.g., using an assay format as defined in Example 3 herein, or a substantially similar assay.

The present invention also includes antibodies and antigen-binding fragments thereof that bind LEPR in complex with human leptin ("LEPR in complex with human leptin" may also be represented by the expression "leptin:LEPR"). For example the present invention includes antibodies and antigen-binding fragments thereof that are capable of binding to a pre-formed complex comprising hLEPR and human leptin. That is, according to certain embodiments, the interaction between anti-LEPR antibodies and LEPR is not inhibited by the presence of leptin in complex with LEPR; likewise, the interaction between leptin and LEPR, according to this aspect of the invention, is not inhibited by the presence of an anti-LEPR antibody. An exemplary assay format for determining whether an antibody or antigen-binding fragment thereof binds to LEPR in complex with human leptin is set forth in Example 4 herein.

The present invention also includes antibodies and antigen-binding fragments thereof that bind cell surface-expressed LEPR in the presence and/or absence of human leptin. Cell surface-expressed LEPR means LEPR or a portion thereof (e.g., an extracellular portion of LEPR) expressed on the surface of a cell, either naturally or in an engineered cell line, such that an antibody or antigen-binding fragment thereof is capable of binding to the LEPR molecule. In certain embodiments, cell surface-expressed LEPR includes recombinant complexes comprising an extracellular domain of LEPR connected to a cell via a tag or anchor (e.g., a GPI anchor as illustrated in Example 6 herein). According to this aspect of the invention, antibodies are provided which are capable of binding cell surface-expressed LEPR in the absence of leptin, and are also capable of binding cell surface-expressed LEPR in the presence of leptin (i.e., under circumstances wherein leptin is capable of binding to cell surface-expressed LEPR). That is, according to certain embodiments, the interaction between anti-LEPR antibodies and cell surface-expressed LEPR is not inhibited by the presence of leptin in complex with cell surface-expressed LEPR. Antibodies according to this aspect of the invention are capable of forming a three-member complex on the surface of a cell comprising the antibody, cell surface-expressed LEPR and leptin. An exemplary assay format for determining whether an antibody or antigen-binding fragment thereof is capable of binding cell surface-expressed LEPR in the presence and absence of human leptin is set forth in Example 5 herein.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a LEPR protein. Alternatively, the epitope may consist of a plurality of non-contiguous amino acids (or amino acid sequences) of LEPR. In some embodiments, the epitope is located on or near the leptin-binding domain of LEPR. In other embodiments, the epitope is located at a region distinct from the leptin-binding domain of LEPR, e.g., at a location on the surface of LEPR at which an antibody, when bound to such an epitope, does not interfere with leptin binding to LEPR.

Various techniques known to persons of ordinary skill in the art can be used to identify the amino acids within an epitope recognized by a particular antibody. Exemplary techniques include, e.g., alanine scanning mutational analysis, peptide blot analysis, and peptide cleavage analysis. In addition, methods such as epitope excision, epitope extraction and chemical modification of antigens can be employed (Tomer (2000) Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259;

Engen and Smith (2001) *Anal. Chem.* 73:256A-265A. X-ray crystallography analysis of an antibody in complex with its antigen may also be used to identify the amino acids within a polypeptide with which an antibody interacts.

The present invention further includes anti-LEPR antibodies that bind to the same epitope as any of the specific exemplary antibodies described herein (e.g. antibodies comprising any of the amino acid sequences as set forth in Table 1 herein). Likewise, the present invention also includes anti-LEPR antibodies that compete for binding to LEPR with any of the specific exemplary antibodies described herein (e.g. antibodies comprising any of the amino acid sequences as set forth in Table 1 herein).

One can determine whether an antibody binds to the same epitope as, or competes for binding with, a reference anti-LEPR antibody by using routine methods known in the art and exemplified herein. For example, to determine if a test antibody binds to the same epitope as a reference anti-LEPR antibody of the invention, the reference antibody is allowed to bind to a LEPR protein. Next, the ability of a test antibody to bind to the LEPR molecule is assessed. If the test antibody is able to bind to LEPR following saturation binding with the reference anti-LEPR antibody, it can be concluded that the test antibody binds to a different epitope than the reference anti-LEPR antibody. On the other hand, if the test antibody is not able to bind to the LEPR molecule following saturation binding with the reference anti-LEPR antibody, then the test antibody may bind to the same epitope as the epitope bound by the reference anti-LEPR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al. (1990) Cancer Res. 50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-LEPR antibody, the above-described binding methodology is performed in two orientations: In a first orientation, the reference antibody is allowed to bind to a LEPR protein under saturating conditions followed by assessment of binding of the test antibody to the LEPR molecule. In a second orientation, the test antibody is allowed to bind to a LEPR molecule under saturating conditions followed by assessment of binding of the reference antibody to the LEPR molecule. If, in both orientations, only the first (saturating) antibody is capable of binding to the LEPR molecule, then it is concluded that the test antibody and the reference antibody compete for binding to LEPR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-LEPR antibodies of the present invention can be fully human antibodies. Methods for generating monoclonal antibodies, including fully human monoclonal antibodies are known in the art. Any such known methods can be used in the context of the present invention to make human antibodies that specifically bind to human LEPR.

Using VELOCIMMUNE™ technology, for example, or any other similar known method for generating fully human monoclonal antibodies, high affinity chimeric antibodies to LEPR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-LEPR antibody. While the constant region selected may vary according to specific use, high affinity antigen-binding and target specificity characteristics reside in the variable region. In certain instances, fully human anti-LEPR antibodies are isolated directly from antigen-positive B cells.

Bioequivalents

The anti-LEPR antibodies and antibody fragments of the present invention encompass proteins having amino acid sequences that vary from those of the described antibodies but that retain the ability to bind human LEPR. Such variant antibodies and antibody fragments comprise one or more additions, deletions, or substitutions of amino acids when compared to parent sequence, but exhibit biological activity that is essentially equivalent to that of the described antibodies. Likewise, the anti-LEPR antibody-encoding DNA sequences of the present invention encompass sequences that comprise one or more additions, deletions, or substitutions of nucleotides when compared to the disclosed sequence, but that encode an anti-LEPR antibody or antibody fragment that is essentially bioequivalent to an anti-LEPR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-LEPR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-LEPR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-LEPR antibodies that bind to human LEPR but not to LEPR from other species. The present invention also includes anti-LEPR antibodies that bind to human LEPR and to LEPR from one or more non-human species. For example, the anti-LEPR antibodies of the invention may bind to human LEPR and may bind or not bind, as the case may be, to one or more of mouse, rat, guinea pig, hamster, gerbil, pig, cat, dog, rabbit, goat, sheep, cow, horse, camel, cynomolgous, marmoset, rhesus or chimpanzee LEPR. According to certain exemplary embodiments of the present invention, anti-LEPR antibodies are provided which specifically bind human LEPR and cynomolgus monkey (e.g., *Macaca fascicularis*) LEPR. Other anti-LEPR antibodies of the invention bind human LEPR but do not bind, or bind only weakly, to cynomolgus monkey LEPR.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al. (1991) *J. Immunol.* 147:60-69; Kufer et al. (2004) *Trends Biotechnol.* 22:238-244. The anti-LEPR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human LEPR, and the other arm of the immunoglobulin is specific for a second antigen. The LEPR-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. (2012) mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-LEPR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like.

The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-LEPR antibodies may be determined empirically; for example, patient progress can be monitored by periodic assessment, and the dose adjusted accordingly. Moreover, interspecies scaling of dosages can be performed using well-known methods in the art (e.g., Mordenti et al. (1991) *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.) (1974) CRC Pres., Boca Raton, Florida. In yet another embodiment, a controlled release system can be placed in proximity of the composition's target, thus requiring only a fraction of the systemic dose (see, e.g., Goodson (1984) in Medical Applications of Controlled Release, supra, vol. 2, pp. 115-138). Other controlled release systems are discussed in the review by Langer (1990) Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an antagonist anti-LEPR antibody (e.g., an anti-LEPR antibody comprising any of the HCVR/LCVR or CDR sequences as set forth in Table 1 herein). The therapeutic composition can comprise any of the anti-LEPR antibodies disclosed herein, or antigen-binding fragments thereof, and a pharmaceutically acceptable carrier or diluent.

The antibodies of the invention are useful, inter alia, for the treatment, prevention and/or amelioration of any disease or disorder associated with or mediated by elevated leptin levels (hyperleptinemia) and/or elevated expression of OB-R leptin receptor that results in excess LEPR signaling. In various embodiments, the disease or disorder is selected, but not limited to, anorexia or other psychiatric eating disorders, chronic kidney disease cachexia, other cachexias such as congestive heart failure cachexia, pulmonary cachexia, radiation cachexia, and cancer cachexia, autoimmune disorders such as inflammatory bowel disease, lupus erythematosus, multiple sclerosis, psoriasis, cardiovascular diseases, elevated blood pressure, depression, neurodegenerative disorders, cancer such as hepatocellular carcinoma, melanoma and breast cancer.

The present invention also includes anti-LEPR antibodies and antigen-binding fragments thereof that are useful for antagonizing LEPR signaling in cells, tissues and organs expressing normal or high leptin levels. As used herein, a LEPR mutant that exhibits enhanced signaling in the presence of leptin (as compared to wild-type LEPR) is referred to as a "signaling enhanced LEPR mutant." An exemplary signaling-enhanced LEPR mutation is LEPR-Q223R (Chagnon et al. (2009) *Journal of Clinical Endocrinology & Metabolism* 85(1):29-34). Thus, the present invention includes anti-LEPR antibodies and antigen-binding fragments thereof that are useful for the treatment, prevention and/or amelioration of diseases and disorders caused by or associated with enhanced signaling LEPR mutants.

In the context of the methods of treatment described herein, the anti-LEPR antibodies may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the anti-LEPR antibodies described herein in combination with one or more additional therapeutically active components, and methods of treatment comprising administering such combinations to subjects in need thereof.

The anti-LEPR antagonist antibodies of the present invention may be co-formulated with and/or administered in combination with one or more additional therapeutically active component(s), such as. e.g., pharmaceutical products prescribed for the treatment of congestive heart failure cachexia, pulmonary cachexia and cancer cachexia, autoimmune disorders such as inflammatory bowel disease, lupus erythematosus, multiple sclerosis, psoriasis, cardiovascular diseases, elevated blood pressure, neurodegenerative disorders, depression, cancer such as hepatocellular carcinoma, melanoma, breast cancer, and other diseases and disorders associated with or caused by decreased leptin signaling. Examples of such additional therapeutically active components include, but are not limited to, e.g., angiotensin-converting enzyme inhibitors (e.g., ACE, ACE-I, benazepril, captopril, enalapril, fosinopril, lisinopril, moexipril, perindopril, quinapril, ramapril, trandolapril), angiotensin receptor blockers (e.g., ARB), smooth muscle relaxants (e.g., hydralazine), long-acting nitrates (e.g., isosorbide dinitrate with or without, e.g., ACE-I and ARBs), diuretics (e.g., loop diuretics, thiazide-like diuretics and potassium-sparing diuretics), iron-deficient anemia treatments (e.g., parenteral iron), long- or short-acting bronchodilators (e.g., β2 agonists such as arformoterol, buphenine, clenbuterol, dopexamine, epinephrine, fentoterol, formoterol, isoetarine, isoprenaline, isoproterenol, levosalbutamol, orciprenaline, pirbuterol, procaterol, ritodrine, salbutamol, albuterol, terbutaline, tiotropium), anticholinergics (e.g., hyoscyamine, atropine, phenobarbital, scopolamine, dicyclomine, phenobarbital, mepenzolate and combinations such as atropine, hyoscyamine, phenobarbital and scopolamine), corticosteroids (e.g., hydrocortisone, hydrocortisone-17-valerate, hydrocortisone-17-butyrate, prednisone, prednisolone, triamcinolone acetonide, triamcinolone alcohol, betamethasone, dexamethasone, fluocortolone, flunisolide, budesonide), long-term antibiotics (e.g., macrolides such as erythromycin, azithromycin, and methylxanthines such as theophylline) non-steroidal anti-inflammatory drugs (NSAIDs) (e.g., aspirin, celecoxib, diclofenac, diflunisal, etodolac, ibuprofen, indomethacin, ketoprofen, naproxen, oxaprozin, piroxicam, salsalate, sulindac, tolmetin, etc.), 5-aminosalicylic acids (5-ASA) (e.g., mesalazine), immunosuppressants (e.g., prednisone, TNF inhibitors, azathioprine, methotrexate, 6-mercaptopurine), relapsing-remitting multiple sclerosis therapies (e.g., interferon beta-1a, interferon beta-1b, glatiramer acetate, mitoxantrone, natalizumab, fingolimod, teriflunomide, dimethyl fumarate, alemtuzumab, daclizumab, CD20 monoclonal antibodies such as rituximab, ocrelizumab and ofatumumab), topical agents for psoriasis treatment (e.g., topical agents such as para-aminobenzoic acid, coconut oil, coal tar, dithranol, corticosteroids such as desoximetasone, fluocinonide, vitamin $D_3$ and other vitamin D analogues, psoralen, and systemic agents such as methotrexate, ciclosporin, hydroxycarbamide, fumarates such as dimethyl fumarate and retinoids), TNF-α antagonists (e.g., infliximab, adalimumab, golimumab and certolizumab pegol), psoriasis treatments that target T-cells (e.g., efalizumab and alefacept), treatments for hypertension and cardiovascular disease (e.g., aspirin, statins such as atorvastatin, fluvastatin, lovastatin, mevastatin, pitavastatin, pravastatin, rosuvastatin, simvastatin and combinations such as simvastatin+ezetimibe, lovastatin+niacin, and atorvastatin+amlodipine), therapies for neurodegenerative disorders (e.g., dimebon, and proline-rich peptide (PRP)-1), antidepressants (e.g., sertraline, citalopram, fluoxetine, escitalopram, trazodone, venlafaxine, bupropion, duloxetine, paroxetine, amitriptyline, venlafacine, desvenlafaxine, and nortriptyline), and anti-cancer therapies (e.g., sorafenib, JX-594, interleukin-2, ipilimumab (Yervoy), nivolumab (Opdivo), pembrolizumab (Keytruda), vemurafenib (Zelboraf), dabrafenib (Tafinlar), Trametinib (Mekinist), anthracyclines such as doxorubicin (Adriamycin®), epirubicin (Ellence®), taxanes such as paclitaxel (Taxol®) and docetaxel (Taxotere®), 5-fluorouracil (5-FU), cyclophosphamide (Cytoxan®), carboplatin (Paraplatin®) or a combination thereof).

Administration Regimens

According to certain embodiments of the present invention, multiple doses of an anti-LEPR antagonist antibody (or a pharmaceutical composition comprising a combination of an anti-LEPR antagonist antibody and any of the additional therapeutically active agents mentioned herein) may be administered to a subject over a defined time course. The methods according to this aspect of the invention comprise sequentially administering to a subject multiple doses of an anti-LEPR antibody of the invention. As used herein, "sequentially administering" means that each dose of anti-LEPR antibody is administered to the subject at a different point in time, e.g., on different days separated by a predetermined interval (e.g., hours, days, weeks or months). The present invention includes methods which comprise sequentially administering to the patient a single initial dose of an anti-LEPR antibody, followed by one or more secondary doses of the anti-LEPR antibody, and optionally followed by one or more tertiary doses of the anti-LEPR antibody.

The terms "initial dose," "secondary doses," and "tertiary doses," refer to the temporal sequence of administration of the anti-LEPR antibody of the invention. Thus, the "initial dose" is the dose which is administered at the beginning of the treatment regimen (also referred to as the "baseline dose," "loading dose," "starting dose," and the like); the "secondary doses" are the doses which are administered after the initial dose; and the "tertiary doses" are the doses which are administered after the secondary doses. The initial, secondary, and tertiary doses may all contain the same amount of anti-LEPR antibody, but generally may differ from one another in terms of frequency of administration. In certain embodiments, however, the amount of anti-LEPR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic and Analytic Uses of the Antibodies

The anti-LEPR antibodies of the present invention may also be used to detect and/or measure LEPR, or LEPR-expressing cells in a sample, e.g., for diagnostic purposes. For example, an anti-LEPR antibody, or fragment thereof, may be used to diagnose a condition or disease characterized by aberrant expression (e.g., over-expression, under-expression, lack of expression, etc.) of LEPR. Exemplary diagnostic assays for LEPR may comprise, e.g., contacting a sample, obtained from a patient, with an anti-LEPR antibody of the invention, wherein the anti-LEPR antibody is labeled with a detectable label or reporter molecule. Alternatively, an unlabeled anti-LEPR antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure LEPR in a sample include enzyme-linked immunosorbent assay (ELISA), radioimmunoassay (RIA), and fluorescence-activated cell sorting (FACS).

Samples that can be used in LEPR diagnostic assays according to the present invention include any tissue or fluid sample obtainable from a patient which contains detectable quantities of LEPR protein, or fragments thereof, under normal or pathological conditions. Generally, levels of LEPR in a particular sample obtained from a healthy patient (e.g., a patient not afflicted with a disease or condition associated with abnormal LEPR levels or activity) will be measured to initially establish a baseline, or standard, level of LEPR. This baseline level of LEPR can then be compared against the levels of LEPR measured in samples obtained from individuals suspected of having a LEPR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Antigen-Binding Proteins that Specifically Bind the Leptin Receptor (LEPR)

Anti-LEPR antibodies were obtained by immunizing a VELOCIMMUNE® mouse (i.e., an engineered mouse comprising DNA encoding human immunoglobulin heavy and kappa light chain variable regions) with an immunogen comprising the extracellular domain of LEPR. The antibody immune response was monitored by a LEPR-specific immunoassay. Using previously described techniques, fully human anti-LEPR antibodies were isolated and purified.

Certain biological properties of the exemplary anti-LEPR antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-LEPR antibodies of the invention. The corresponding nucleic acid sequence identifiers are set forth in Table 2.

TABLE 1

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H17322P2 | 2 | 4 | 6 | 8 | 10 | 12 | 14 AAS | 16 |
| H4H18437P2 | 18 | 20 | 22 | 24 | 10 | 12 | 14 AAS | 16 |
| H4H18439P2 | 26 | 28 | 30 | 32 | 10 | 12 | 14 AAS | 16 |
| H4H18440P2 | 34 | 36 | 38 | 40 | 10 | 12 | 14 AAS | 16 |
| H4H18457P2 | 42 | 44 | 46 | 48 | 10 | 12 | 14 AAS | 16 |
| H4H18462P2 | 50 | 52 | 54 | 56 | 10 | 12 | 14 AAS | 16 |
| H4H18464P2 | 58 | 60 | 62 | 64 | 10 | 12 | 14 AAS | 16 |
| H4H18466P2 | 66 | 68 | 70 | 72 | 10 | 12 | 14 AAS | 16 |
| H4H18508P2 | 74 | 76 | 78 | 80 | 82 | 84 | 86 GAS | 88 |

TABLE 2

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H17322P2 | 1 | 3 | 5 | 7 | 9 | 11 | 13 gctgcatcc | 15 |
| H4H18437P2 | 17 | 19 | 21 | 23 | 9 | 11 | 13 gctgcatcc | 15 |
| H4H18439P2 | 25 | 27 | 29 | 31 | 9 | 11 | 13 gctgcatcc | 15 |
| H4H18440P2 | 33 | 35 | 37 | 39 | 9 | 11 | 13 gctgcatcc | 15 |
| H4H18457P2 | 41 | 43 | 45 | 47 | 9 | 11 | 13 gctgcatcc | 15 |
| H4H18462P2 | 49 | 51 | 53 | 55 | 9 | 11 | 13 gctgcatcc | 15 |
| H4H18464P2 | 57 | 59 | 61 | 63 | 9 | 11 | 13 gctgcatcc | 15 |
| H4H18466P2 | 65 | 67 | 69 | 71 | 9 | 11 | 13 gctgcatcc | 15 |
| H4H18508P2 | 73 | 75 | 77 | 79 | 81 | 83 | 85 ggtgcatcc | 87 |

Antibodies are typically referred to herein according to the following nomenclature: Fc prefix (e.g. "H4H," "H1M," "H2M," etc.), followed by a numerical identifier (e.g. "17322," 18457", etc.), followed by a "P" or "N" suffix. Thus, according to this nomenclature, an antibody may be referred to herein as, e.g., "H4H17322P2," "H4H18457P2," etc. The Fc prefixes on the antibody designations used herein (H4H, H1M and H2M) indicate the particular Fc region isotype of the antibody. For example, an "H4H" antibody has a human IgG4 Fc, whereas an "H1M" antibody has a mouse IgG1 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Comparator Antibody. The Comparator antibody used in the following Examples refers to Fab 9F8 described in Fazeli et al. (2006) J Immunol Methods 312:190-200 and Carpenter et al. (2012) Structure 20(3):487-97.

Example 3. Surface Plasmon Resonance Derived Binding Affinities and Kinetic Constants of Human Monoclonal Anti-LEPR Antibodies Equilibrium dissociation constants ($K_D$ values) for antigen binding to purified anti-LEPR monoclonal antibodies of the invention were determined using a real-time surface plasmon resonance biosensor using a Biacore 4000 instrument. All binding studies were performed in running buffer containing 10 mM HEPES, 150 mM NaCl, 3 mM EDTA, and 0.05% v/v Surfactant Tween-20, pH 7.4 (HBS-ET running buffer) at 25° C. and 37° C. The Biacore sensor surface was first derivatized by amine coupling with a monoclonal mouse anti-human Fc antibody (GE, #BR-1008-39) to the capture anti-LEPR monoclonal antibodies. The LEPR reagents tested for binding to the anti-LEPR monoclonal antibodies included recombinant human LEPR extracellular domain expressed with a C-terminal myc-myc-hexahistidine tag (hLEPR.MMH; SEQ ID NO:90), recombinant cynomolgus monkey LEPR extracellular domain expressed with a C-terminal myc-myc-hexahistidine tag (mfLEPR.MMH; SEQ ID NO:93), recombinant mouse LEPR extracellular domain expressed with a C-terminal myc-myc-hexahistidine tag (mLEPR.MMH; SEQ ID NO:94), recombinant rat LEPR extracellular domain expressed with a C-terminal myc-myc-hexahistidine tag (rLEPR.MMH; SEQ ID NO:95), and recombinant human LEPR extracellular domain expressed with a C-terminal mouse IgG2a Fc tag (hLEPR.mFc; SEQ ID NO:91). LEPR constructs that include MMH tags are monomeric LEPR constructs, and LEPR constructs including an mFc tag are dimeric LEPR constructs. Different concentrations of LEPR reagents were first prepared in HBS-ET running buffer at final concentrations ranging from 100 nM to 3.7 nM in 3-fold serial dilutions and were then injected over the anti-LEPR monoclonal antibody captured surface for 4 minutes at a flow rate of 304/minute. The dissociation of monoclonal antibody bound LEPR reagent was monitored for 10 minutes in HBS-ET running buffer. Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln(2)}{60 * kd}$$

Binding kinetics parameters for hLEPR-MMH, mfLEPR-MMH, hLEPR.mFc, mLEPR-MMH or rLEPR-MMH binding to different anti-LEPR monoclonal antibodies of the invention at 25° C. and 37° C. are shown in Tables 3 through 13.

TABLE 3

Binding kinetics parameters of anti-LEPR antibodies binding to hLEPR-MMH at 25° C.

| mAb Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H17322P2 | 178 ± 1.2 | 66 | 4.38E+04 | 2.24E−04 | 5.11E−09 | 52 |
| H4H18437P2 | 171 ± 0.5 | 56 | 5.74E+04 | 3.75E−03 | 6.53E−08 | 3.1 |
| H4H18439P2 | 156 ± 0.7 | 21 | 1.07E+04 | 1.13E−03 | 1.06E−07 | 10 |
| H4H18440P2 | 170 ± 0.5 | 71 | 4.23E+04 | 4.97E−04 | 1.18E−08 | 23 |
| H4H18457P2 | 166 ± 0.9 | 119 | 2.55E+05 | 2.52E−03 | 9.89E−09 | 5 |
| H4H18462P2 | 175 ± 0.6 | 34 | 6.79E+04 | 7.65E−03 | 1.13E−07 | 1.5 |
| H4H18464P2 | 160 ± 0.4 | 60 | 1.24E+05 | 1.13E−03 | 9.09E−09 | 10 |
| H4H18466P2 | 161 ± 0.5 | 24 | 2.64E+04 | 5.11E−03 | 1.94E−07 | 2.3 |
| H4H18508P2 | 180 ± 1.5 | 127 | 1.76E+05 | 1.67E−03 | 9.53E−09 | 7 |
| Comparator Antibody | 380 ± 8.2 | 26 | 4.48E+04 | 7.46E−05 | 1.66E−09 | 155 |
| Isotype Control Antibody | 171 ± 0.4 | 4 | NB* | NB* | NB* | NB* |

*NB indicates that no binding was observed under the current experimental conditions.

TABLE 4

Binding kinetics parameters of anti-LEPR antibodies binding to hLEPR-MMH at 37° C.

| mAb Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H17322P2 | 225 ± 3 | 99 | 6.95E+04 | 8.12E−04 | 1.17E−08 | 14 |
| H4H18437P2 | 213 ± 3 | 55 | 1.14E+05 | 8.84E−03 | 7.76E−08 | 1.3 |
| H4H18439P2 | 180 ± 1.5 | 19 | 2.32E+04 | 4.69E−03 | 2.02E−07 | 2.5 |
| H4H18440P2 | 207 ± 1.2 | 95 | 6.34E+04 | 1.73E−03 | 2.73E−08 | 7 |
| H4H18457P2 | 198 ± 1.6 | 108 | 3.45E+05 | 8.55E−03 | 2.48E−08 | 1.4 |
| H4H18462P2 | 204 ± 2.1 | 31 | 4.58E+04 | 1.14E−02 | 2.48E−07 | 1.0 |
| H4H18464P2 | 185 ± 1.2 | 68 | 1.54E+05 | 3.15E−03 | 2.05E−08 | 3.7 |
| H4H18466P2 | 184 ± 1.3 | 26 | 4.55E+04 | 6.74E−03 | 1.48E−07 | 1.7 |
| H4H18508P2 | 204 ± 1.4 | 117 | 2.69E+05 | 6.88E−03 | 2.55E−08 | 1.7 |
| Comparator Antibody | 315 ± 7.6 | 37 | 5.39E+04 | 4.81E−04 | 8.92E−09 | 24 |
| Isotype Control Antibody | 193 ± 1.5 | 6 | NB* | NB* | NB* | NB* |

*NB indicates that no binding was observed under the current experimental conditions.

As shown in Table 3, at 25° C., all of the anti-LEPR monoclonal antibodies of the invention bound to hLEPR-MMH with $K_D$ values ranging from 5.11 nM to 194 nM. As shown in Table 4, at 37° C., all of the anti-LEPR monoclonal antibodies of the invention bound to hLEPR-MMH with $K_D$ values ranging from 11.7 nM to 248 nM.

TABLE 5

Binding kinetics parameters of anti-LEPR antibodies binding to mfLEPR-MMH at 25° C.

| mAb Captured | mAb Capture Level (RU) | 100 nM mfLEPR-MMH Bound (RU) | $k_a$ (1/Ms) | $k_d$ (1/s) | $K_D$ (M) | t½ (min) |
|---|---|---|---|---|---|---|
| H4H17322P2 | 177 ± 0.5 | 102 | 7.02E+04 | 2.92E−04 | 4.16E−09 | 40 |
| H4H18437P2 | 171 ± 0.3 | 70 | 6.87E+04 | 4.05E−03 | 5.89E−08 | 2.9 |
| H4H18439P2 | 155 ± 0.5 | 22 | 1.57E+04 | 1.52E−03 | 9.63E−08 | 8 |
| H4H18440P2 | 170 ± 0.9 | 67 | 4.95E+04 | 2.68E−03 | 5.41E−08 | 4.3 |
| H4H18457P2 | 165 ± 0.4 | 133 | 2.73E+05 | 3.31E−03 | 1.22E−08 | 3.5 |
| H4H18462P2 | 174 ± 0.4 | 42 | 7.42E+04 | 1.33E−02 | 1.79E−07 | 0.9 |
| H4H18464P2 | 159 ± 0.4 | 15 | 3.82E+04 | 2.31E−03 | 6.04E−08 | 5.0 |
| H4H18466P2 | 161 ± 0.5 | 30 | 4.50E+04 | 6.69E−03 | 1.48E−07 | 1.7 |

TABLE 5-continued

Binding kinetics parameters of anti-LEPR antibodies binding to mfLEPR-MMH at 25° C.

| mAb Captured | mAb Capture Level (RU) | 100 nM mfLEPR-MMH Bound (RU) | $k_a$ (1/Ms) | $k_d$ (1/s) | $K_D$ (M) | t½ (min) |
|---|---|---|---|---|---|---|
| H4H18508P2 | 178 ± 0.4 | 145 | 2.04E+05 | 1.63E−03 | 8.00E−09 | 7 |
| Comparator Antibody | 359 ± 4.8 | 1 | NB* | NB* | NB* | NB* |
| Isotype Control Antibody | 171 ± 0.4 | 0 | NB* | NB* | NB* | NB* |

*NB indicates that no binding was observed under the current experimental conditions.

TABLE 6

Binding kinetics parameters of anti-LEPR antibodies binding to mfLEPR-MMH at 37° C.

| mAb Captured | mAb Capture Level (RU) | 100 nM mfLEPR-MMH Bound (RU) | $k_a$ (1/Ms) | $k_d$ (1/s) | $K_D$ (M) | t½ (min) |
|---|---|---|---|---|---|---|
| H4H17322P2 | 218 ± 1.7 | 142 | 1.43E+05 | 1.10E−03 | 7.72E−09 | 10 |
| H4H18437P2 | 207 ± 1.4 | 58 | 8.69E+04 | 1.27E−02 | 1.47E−07 | 0.9 |
| H4H18439P2 | 178 ± 1.4 | 14 | 4.69E+04 | 7.92E−03 | 1.69E−07 | 1.5 |
| H4H18440P2 | 204 ± 1 | 66 | 7.15E+04 | 7.24E−03 | 1.01E−07 | 1.6 |
| H4H18457P2 | 195 ± 1.4 | 117 | 3.47E+05 | 1.04E−02 | 3.00E−08 | 1.1 |
| H4H18462P2 | 199 ± 1.1 | 28 | 1.29E+05 | 3.37E−02 | 2.61E−07 | 0.3 |
| H4H18464P2 | 183 ± 0.6 | 13 | 3.92E+04 | 8.41E−03 | 2.15E−07 | 1.4 |
| H4H18466P2 | 181 ± 0.9 | 27 | 8.43E+04 | 1.38E−02 | 1.64E−07 | 0.8 |
| H4H18508P2 | 200 ± 1 | 125 | 2.85E+05 | 7.89E−03 | 2.77E−08 | 1.5 |
| Comparator Antibody | 298 ± 3.2 | −1 | NB* | NB* | NB* | NB* |
| Isotype Control Antibody | 190 ± 1 | 1 | NB* | NB* | NB* | NB* |

*NB indicates that no binding was observed under the current experimental conditions.

As shown in Table 5, at 25° C., all of the anti-LEPR monoclonal antibodies of the invention bound to mfLEPR-MMH with $K_D$ values ranging from 4.16 nM to 179 nM. As shown in Table 6, at 37° C., all of the anti-LEPR monoclonal antibodies of the invention bound to mfLEPR-MMH with $K_D$ values ranging from 7.72 nM to 261 nM.

TABLE 7

Binding kinetics parameters of anti-LEPR antibodies binding to hLEPR-mFc at 25° C.

| mAb Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H17322P2 | 176 ± 0.4 | 74 | 6.45E+04 | 1.14E−04 | 1.77E−09 | 102 |
| H4H18437P2 | 169 ± 1.1 | 70 | 1.02E+05 | 5.36E−04 | 5.27E−09 | 22 |
| H4H18439P2 | 155 ± 0.2 | 53 | 4.87E+04 | 1.80E−04 | 3.69E−09 | 64 |
| H4H18440P2 | 169 ± 0.5 | 140 | 1.54E+05 | 6.82E−05 | 4.43E−10 | 169 |
| H4H18457P2 | 165 ± 0.8 | 149 | 4.91E+05 | 4.23E−04 | 8.63E−10 | 27 |
| H4H18462P2 | 173 ± 0.5 | 68 | 9.08E+04 | 2.96E−04 | 3.26E−09 | 39 |
| H4H18464P2 | 159 ± 0.4 | 84 | 2.11E+05 | 1.88E−04 | 8.91E−10 | 61 |
| H4H18466P2 | 160 ± 0.2 | 37 | 3.97E+04 | 4.72E−04 | 1.19E−08 | 24 |

TABLE 7-continued

Binding kinetics parameters of anti-LEPR antibodies binding to hLEPR-mFc at 25° C.

| mAb Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H18508P2 | 178 ± 0.4 | 138 | 2.21E+05 | 2.99E−04 | 1.35E−09 | 39 |
| Comparator Antibody | 344 ± 4.9 | 36 | 1.56E+05 | 1.45E−05 | 9.28E−11 | 798 |
| Isotype Control Antibody | 170 ± 0.7 | −2 | NB* | NB* | NB* | NB* |

*NB indicates that no binding was observed under the current experimental conditions.

TABLE 8

Binding kinetics parameters of anti-LEPR antibodies binding to hLEPR-mFc at 37° C.

| mAb Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H17322P2 | 214 ± 1.8 | 105 | 1.33E+05 | 4.40E−04 | 3.31E−09 | 26 |
| H4H18437P2 | 202 ± 1.1 | 88 | 1.29E+05 | 5.56E−04 | 4.30E−09 | 21 |
| H4H18439P2 | 176 ± 0.7 | 67 | 6.09E+04 | 9.23E−04 | 1.51E−08 | 13 |
| H4H18440P2 | 200 ± 1.4 | 181 | 2.12E+05 | 1.12E−04 | 5.27E−10 | 103 |
| H4H18457P2 | 193 ± 1 | 166 | 5.56E+05 | 7.04E−04 | 1.27E−09 | 16 |
| H4H18462P2 | 196 ± 0.9 | 84 | 1.28E+05 | 5.43E−04 | 4.26E−09 | 21 |
| H4H18464P2 | 182 ± 0.4 | 105 | 4.04E+05 | 5.17E−04 | 1.28E−09 | 22 |
| H4H18466P2 | 179 ± 1 | 52 | 5.87E+04 | 5.20E−04 | 8.86E−09 | 22 |
| H4H18508P2 | 198 ± 1 | 146 | 4.71E+05 | 1.02E−03 | 2.16E−09 | 11 |
| Comparator Antibody | 288 ± 2.5 | 50 | 1.50E+05 | 7.74E−05 | 5.14E−10 | 149 |
| Isotype Control Antibody | 188 ± 0.8 | 1 | NB* | NB* | NB* | NB* |

*NB indicates that no binding was observed under the current experimental conditions.

As shown in Table 7, at 25° C., all of the anti-LEPR monoclonal antibodies of the invention bound to hLEPR-mFc with $K_D$ values ranging from 443 pM to 11.9 nM. As shown in Table 8, at 37° C., all of the anti-LEPR monoclonal antibodies of the invention bound to hLEPR-mFc with $K_D$ values ranging from 527 pM to 15.1 nM.

TABLE 9

Binding kinetics parameters of anti-LEPR monoclonal antibodies binding to mLEPR-MMH at 25° C.

| mAb Captured | mAb Capture Level (RU) | 100 nM mLEPR-MMH Bound (RU) | $k_a$ (1/Ms) | $k_d$ (1/s) | $K_D$ (M) | t½ (min) |
|---|---|---|---|---|---|---|
| H4H17322P2 | 176 | 0 | NB* | NB* | NB* | NB* |
| H4H18437P2 | 169 | 6 | 1.58E+04 | 4.18E−03 | 2.64E−07 | 2.8 |
| H4H18439P2 | 155 | −2 | NB* | NB* | NB* | NB* |
| H4H18440P2 | 169 | −3 | NB* | NB* | NB* | NB* |
| H4H18457P2 | 164 | 1 | NB* | NB* | NB* | NB* |
| H4H18462P2 | 173 | 2 | NB* | NB* | NB* | NB* |
| H4H18464P2 | 159 | −1 | NB* | NB* | NB* | NB* |
| H4H18466P2 | 160 | 1 | NB* | NB* | NB* | NB* |
| H4H18508P2 | 177 | 25 | 2.78E+05 | 6.07E−02 | 2.18E−07 | 0.19 |
| Comparator Antibody | 334 ± 2.5 | 2 | NB* | NB* | NB* | NB* |
| Isotype Control Antibody | 169 | −2 | NB* | NB* | NB* | NB* |

*NB indicates that no binding was observed under the current experimental conditions.

TABLE 10

Binding kinetics parameters of anti-LEPR antibodies binding to mLEPR-MMH at 37° C.

| mAb Captured | mAb Capture Level (RU) | 100 nM mLEPR-MMH Bound (RU) | $k_a$ (1/Ms) | $k_d$ (1/s) | $K_D$ (M) | t½ (min) |
|---|---|---|---|---|---|---|
| H4H17322P2 | 212 | −1 | NB* | NB* | NB* | NB* |
| H4H18437P2 | 201 | 6 | 1.15E+04 | 1.33E−02 | 1.16E−06 | 0.9 |
| H4H18439P2 | 175 | −1 | NB* | NB* | NB* | NB* |
| H4H18440P2 | 200 | −1 | NB* | NB* | NB* | NB* |
| H4H18457P2 | 191 | −1 | NB* | NB* | NB* | NB* |
| H4H18462P2 | 194 | 3 | IC* | IC* | IC* | IC* |
| H4H18464P2 | 181 | 1 | NB* | NB* | NB* | NB* |
| H4H18466P2 | 178 | 3 | NB* | NB* | NB* | NB* |
| H4H18508P2 | 196 | 17 | 5.12E+05 | 1.05E−01 | 2.05E−07 | 0.11 |
| Comparator Antibody | 283 ± 1.1 | 0 | NB* | NB* | NB* | NB* |
| Isotype Control Antibody | 187 | 0 | NB* | NB* | NB* | NB* |

*NB indicates that no binding was observed under the current experimental conditions.

*IC indicates that observed binding was inclusive and was unable to fit the real time binding data under the current experimental conditions.

As shown in Table 9, at 25° C., two out of 9 of the anti-LEPR monoclonal antibodies of the invention bound to mLEPR-MMH with $K_D$ values of 218 nM and 264 nM. As shown in Table 10, at 37° C., two out of 9 of the anti-LEPR monoclonal antibodies of the invention bound to mLEPR-MMH with $K_D$ values of 205 nM and 1.16 μM.

TABLE 11

Binding kinetics parameters of anti-LEPR antibodies binding to rLEPR-MMH at 25° C.

| mAb Captured | mAb Capture Level (RU) | 100 nM rLEPR-MMH Bound (RU) | $k_a$ (1/Ms) | $k_d$ (1/s) | $K_D$ (M) | t½ (min) |
|---|---|---|---|---|---|---|
| H4H17322P2 | 176 ± 0.9 | 10 | IC* | IC* | IC* | IC* |
| H4H18437P2 | 169 ± 0.2 | 13 | 4.21E+04 | 1.38E−02 | 3.28E−07 | 0.8 |
| H4H18439P2 | 155 ± 0.2 | −1 | NB* | NB* | NB* | NB* |
| H4H18440P2 | 169 ± 0.4 | −2 | NB* | NB* | NB* | NB* |
| H4H18457P2 | 164 ± 0.5 | 18 | 2.83E+04 | 2.06E−02 | 7.30E−07 | 0.6 |
| H4H18462P2 | 173 ± 0.2 | 5 | 3.21E+04 | 1.08E−02 | 3.36E−07 | 1.1 |
| H4H18464P2 | 159 ± 0 | −1 | NB* | NB* | NB* | NB* |
| H4H18466P2 | 160 ± 0.6 | 5 | 2.10E+04 | 1.98E−02 | 9.43E−07 | 0.6 |
| H4H18508P2 | 177 ± 0.1 | 22 | 1.39E+05 | 4.76E−02 | 3.41E−07 | 0.24 |
| Comparator Antibody | 328 ± 1.6 | 1 | NB* | NB* | NB* | NB* |
| Isotype Control Antibody | 170 ± 0.2 | −1 | NB* | NB* | NB* | NB* |

*NB indicates that no binding was observed under the current experimental conditions.

*IC indicates that observed binding was inclusive and was unable to fit the real time binding data under the current experimental conditions.

TABLE 12

Binding kinetics parameters of anti-LEPR antibodies binding to rLEPR-MMH at 37° C.

| mAb Captured | mAb Capture Level (RU) | 100 nM rLEPR-MMH Bound (RU) | $k_a$ (1/Ms) | $k_d$ (1/s) | $K_D$ (M) | t½ (min) |
|---|---|---|---|---|---|---|
| H4H17322P2 | 212 ± 0.3 | 9 | 9.32E+04 | 3.28E−02 | 3.52E−07 | 0.4 |
| H4H18437P2 | 200 ± 0 | 10 | 3.07E+04 | 1.93E−02 | 6.29E−07 | 0.6 |
| H4H18439P2 | 175 ± 0.8 | 0 | NB* | NB* | NB* | NB* |
| H4H18440P2 | 200 ± 0.1 | 0 | NB* | NB* | NB* | NB* |
| H4H18457P2 | 192 ± 0.3 | 16 | 3.02E+04 | 1.75E−02 | 5.80E−07 | 0.7 |
| H4H18462P2 | 194 ± 0.9 | 5 | IC* | IC* | IC* | IC* |
| H4H18464P2 | 181 ± 0.1 | 1 | NB* | NB* | NB* | NB* |
| H4H18466P2 | 177 ± 0.7 | 6 | 3.26E+04 | 2.52E−02 | 7.71E−07 | 0.5 |
| H4H18508P2 | 196 ± 1.6 | 17 | 2.71E+05 | 4.57E−02 | 1.68E−07 | 0.25 |
| Comparator Antibody | 279 ± 0.4 | −1 | NB* | NB* | NB* | NB* |
| Isotype Control Antibody | 186 ± 0.1 | 0 | NB* | NB* | NB* | NB* |

*NB indicates that no binding was observed under the current experimental conditions.

*IC indicates that observed binding was inclusive and was unable to fit the real time binding data under the current experimental conditions.

As shown in Table 11, at 25° C., five out of 9 of the anti-LEPR monoclonal antibodies of the invention bound to rLEPR-MMH with $K_D$ values ranging from 328 nM to 943 nM. As shown in Table 12, at 37° C., five out of 9 of the anti-LEPR monoclonal antibodies of the invention bound to rLEPR-MMH with $K_D$ values ranging from 168 nM to 771 nM.

Example 4. Anti-LEPR Antibodies of the Invention do not Block hLEPR-hFc Binding to hLeptin The ability of anti-LEPR monoclonal antibodies of the invention to block binding of dimeric human LEPR to its natural ligand, human Leptin, was measured using a competition sandwich ELISA.

For the ELISA, human Leptin (hLeptin; R&D Systems, #398-LP-01M) was coated at a concentration of 5 µg/mL in PBS on a 96-well microtiter plate overnight at 4° C. Non-specific binding sites were subsequently blocked using a 0.5% (w/v) solution of BSA in PBS. A constant amount of 10 nM of extracellular domain portion of LEPR protein that was expressed with a C-terminal human Fc tag (hLEPR.hFc; SEQ ID NO:92) was titrated with anti-LEPR antibodies, hLeptin protein, or an isotype control antibody ranging from 8.5 pM to 500 nM in serial dilution. These antibody-protein or protein-protein complexes were then incubated for 1.5 hour at room temperature (RT). Complexes were subsequently transferred to microtiter plates coated with hLeptin and incubated for 2 hours at RT, the wells were washed, and plate-bound hLEPR-hFc was detected with an anti-human IgG polyclonal antibody conjugated with horseradish peroxidase (Jackson ImmunoResearch Inc, #109-035-098). Samples were developed with a TMB solution (BD Biosciences, #555214; substrate A and B mixed at 1:1 ratio as per manufacturer's instructions) to produce a colorimetric reaction and then neutralized with 1M sulfuric acid before measuring absorbance at 450 nm on a Victor X5 plate reader. Data analysis was performed using a sigmoidal dose-response model within Prism™ software (Graph Pad). Percent blockade at maximum concentration of the antibody tested was calculated as an indicator of the ability of the antibodies to block the binding of 10 nM of hLEPR-hFc to human Leptin on the plate. In the calculation, binding signal of 10 nM of hLEPR-hFc without the presence of the antibody was referenced as 100% binding or 0% blocking; and the baseline signal of buffer alone without the presence of hLEPR-hFc was referenced as 0% binding or 100% blocking The blocking data at 500 nM antibody concentration is summarized in Table 13.

TABLE 13

ELISA blocking of hLEPR-hFc binding to hLeptin by anti-LEPR antibodies

| Antibody | 500 nM Ab Blocking of 10 nM hLEPR-hFc Binding to hLeptin (% blockade) |
|---|---|
| H4H18440P2 | 3 |
| H4H18466P2 | 2 |
| H4H18457P2 | 4 |
| H4H18437P2 | 9 |
| H4H18464P2 | −5 |
| H4H17322P2 | 13 |
| H4H18439P2 | −1 |
| H4H18462P2 | 14 |
| H4H18508P2 | 40 |
| Controls | |
| Isotype control antibody | −3 |
| Human Leptin | 99 |
| Comparator Antibody | 99 |
| Mouse IgG2a Isotype control | 32 |

As shown in Table 13, none of the anti-LEPR antibodies of the invention demonstrated >40% blockade of the binding of hLEPR-hFc to the hLeptin coated surface. However, the Comparator Antibody and the hLeptin, as the positive control, were able to block 99% of the hLEPR-hFc binding to the hLeptin coated surface. The isotype control antibody demonstrated no measurable blocking at concentrations up to 500 nM.

Example 5. Cell Binding by FACS Analysis with HEK293/Mycx2-hLEPR(Ecto)-GPI Anchored Cells Leptin receptor, LEPR, is a single-pass transmembrane receptor of the class I cytokine receptor family with a large, 818 amino acid long extracellular domain (Tartaglia (1997) J. Biol. Chem 7:272(10):6093-6). LEPR can bind to Leptin, a protein predominantly expressed by adipose tissue that is involved in regulation of food intake and metabolism (Friedman (2014) J Endocrinol 223(1):T1-8). Different isoforms of LEPR exist yielding soluble or membrane-bound forms of the receptor and the membrane-bound forms differ in the length of their intracellular domain. The isoform with the longest intracellular domain is highly expressed in the hypothalamus, an important site of Leptin action in relation to obesity (Friedman and Halaas (1998) *Nature* 395(6704): 763-70). LEPR is localized predominantly within the cell bodies and to a lesser extent on the cell surface. LEPR undergoes ligand-induced internalization adding an additional level of regulation of Leptin signaling (Sweeney (2002) *Cell Signal* 14(8):655-63).

In order to assess cell binding by anti-LEPR antibodies of the invention, a HEK293 cell line was generated to stably express the extracellular domain of human LEPR (hLEPR; amino acids 22-839 of accession #P48357, Isoform B) with an N-terminal myc-myc tag and C-terminal peptide sequence from human carboxypeptidase M that guides the addition of glycosylphosphatidylinositol (GPI) (Marcic et al. (2000) *J Biol Chem.* 275(21):16110-8) such that the protein can be GPI-anchored to the membrane. Since the hLEPR in the cell line does not possess an intracellular domain, it is not internalized upon ligand binding, greatly increasing the amount of LEPR available for antibody and/or ligand binding. The cell line was selected in DMEM containing 10% FBS, NEAA, penicillin/streptomycin, and 500 μg/mL of G418, then sorted for high expression of the receptor using an anti-Myc antibody. The resulting stable cell line, referred to as HEK293/hLEPR-GPI, was maintained in DMEM containing 10% FBS, NEAA, and penicillin/streptomycin.

For the FACS analysis, HEK293 parental cells and HEK293/hLEPR-GPI cells were dissociated and plated onto 96-well v-bottom plates at $5\times10^5$ cells/well in PBS containing 2% FBS (FACS buffer). In order to test whether the anti-hLEPR antibodies binding to cells is affected by the presence of Leptin, FACS buffer with or without 1 μM human Leptin (R&D Systems, #398-LP) was incubated with the cells for 30 minutes at 4° C., followed by the addition of anti-LEPR antibodies or control antibodies at 10 nM in FACS buffer. The cells were subsequently incubated for 30 minutes at 4° C., followed by washing and then incubation with 16 μg/mL of Alexa Fluor®-647 conjugated secondary antibody (Jackson ImmunoResearch Laboratories Inc., #109-547-003) for 30 minutes at 4° C. Cells were subsequently fixed using BD CytoFix™ (Becton Dickinson, #554655), filtered, and analyzed on a HyperCyt Flow Cytometer (Beckman Coulter). Unstained and secondary antibody alone controls were also tested for all cell lines. The results were analyzed using ForeCyt (IntelliCyt) and FlowJo version 10 softwares to determine the geometric means of fluorescence for viable cells. The geometric mean of fluorescence for each sample was then normalized to the geometric mean of unstained cells to obtain relative binding per condition referred to as "binding ratios", and these binding ratios were recorded in Table 14 for each antibody tested.

As shown in Table 14, the 9 anti-LEPR antibodies of the invention tested at 10 nM demonstrated binding to HEK293/hLEPR-GPI cells with binding ratios ranging from 824-fold to 3187-fold without Leptin and 398-fold to 3590-fold in the presence of 1 μM Leptin. Based on the similarity of these binding ratios, the ability of the anti-LEPR antibodies of the invention to bind to LEPR expressed on cells does not appear to be significantly affected by the presence of excess Leptin at 1 μM, suggesting that the binding sites of the anti-LEPR antibodies on LEPR do not overlap with Leptin binding sites on LEPR. The anti-LEPR antibodies of the invention did not demonstrate any significant binding to the HEK293 parental cells with binding ratios with and without 1 μM Leptin ranging from 1- to 9-fold. Binding of the comparator to cells expressing GPI-anchored LEPR was significantly reduced in the presence of Leptin. The isotype control antibody and secondary antibody alone samples also did not demonstrate significant binding to either cell line with or without Leptin, with binding ratios ranging from 1- to 6-fold.

TABLE 14

Binding of 10 nM anti-LEPR antibodies to HEK293/hLEPR-GPI and HEK293 parental cells +/−1 μM Human Leptin

| | Binding Ratio: Normalized to Unstained Sample of Each Cell Line | | | |
|---|---|---|---|---|
| | No added Leptin | | 1 μM Leptin | |
| Antibody | HEK293 parental | HEK293/hLEPR-GPI | HEK293 parental | HEK293/hLEPR-GPI |
| H4H17322P2 | 3 | 1307 | 6 | 1317 |
| H4H18457P2 | 2 | 3187 | 3 | 3106 |
| H4H18464P2 | 5 | 2318 | 7 | 3590 |
| H4H18437P2 | 1 | 1314 | 2 | 1441 |
| H4H18439P2 | 4 | 1533 | 6 | 2477 |
| H4H18440P2 | 3 | 1640 | 7 | 2557 |
| H4H18462P2 | 2 | 1173 | 3 | 759 |
| H4H18466P2 | 1 | 824 | 2 | 398 |
| H4H18508P2 | 1 | 1311 | 2 | 1873 |
| Comparator Antibody | 6 | 2349 | 3 | 112 |
| Human IgG isotype control antibody | 1 | 6 | 2 | 4 |
| Anti-human IgG secondary antibody alone | 1 | 3 | 2 | 3 |
| Mouse IgG isotype control antibody | 2 | 2 | 3 | 3 |
| Anti-mouse IgG secondary antibody alone | 2 | 2 | 2 | 2 |
| Unstained | 1 | 1 | 1 | 1 |

Example 6: Anti-LEPR Antibodies of the Invention Demonstrated Complete Inhibition of Leptin Signaling in the Presence of hLeptin A bioassay was developed to detect the transcriptional activation of STAT3 via LEPR activation using a reporter cell line that stably expresses full-length human LEPR (hLEPR; amino acids 1 through 1165 of accession number NP_002294.2) along with a luciferase reporter (STAT3-Luc; Qiagen, #CLS-6028L) in an IMR-32 cell line, a human neuroblastoma cell line. The resulting stable cell line, referred to as IMR-32/STAT3-Luc/hLEPR, was isolated and maintained in MEM-Earl medium supplemented with 10% FBS, NEAA, 1 ug/mL Puromycin, 100 ug/mL of Hygromycin B and Penicillin/Streptomycin/L-Glutamine (Complete Medium).

The resulting bioassay was used to measure the effect of anti-LEPR antibodies of the invention on LEPR signaling in the presence or absence of Leptin. For the bioassay, IMR-32/STAT3-Luc/hLEPR cells were plated at a density of 20,000 cells/100 ul/well for 96 well format in the complete medium and then the following day the medium was replaced with the appropriate volume of Opti-MEM supplemented with 1% BSA and 0.1% FBS (Assay Buffer) for 30 minutes. To measure the effect of the antibodies of the invention in the absence of Leptin, the anti-LEPR antibodies or an isotype control antibody were half-log serially diluted to final concentrations ranging from 100 nM to 300 fM in Assay Buffer and were then added to the cells and subsequently incubated overnight at 37° C. in 5% $CO_2$. To measure the effect of the antibodies of the invention in the presence of Leptin, a fixed concentration of human Leptin (hLeptin; R&D Systems, #398-LP) at 200 pM in Assay Buffer was added to the cells, immediately followed by the addition of anti-LEPR antibodies or isotype control antibody that were half-log serially diluted to final concentrations ranging from 100 nM to 300 fM. The samples were then incubated overnight at 37° C. in 5% $CO_2$. OneGlo reagent (Promega, #E6051) was then added to the samples and luciferase activity was measured on a Envision Multilable Plate Reader (Perkin Elmer) in Luminescent mode. The relative light units (RLU) values were obtained and the results were analyzed using nonlinear regression with Graph Pad Prism software (Graph Pad). The maximum RLU value obtained from the hLeptin dose response was defined as 100% activation in the IMR-32/STAT3-Luc/hLEPR assay.

As shown in Table 15, in the absence of hLeptin, the anti-LEPR antibodies tested demonstrated weak stimulation of the IMR-32/STAT3-Luc/hLEPR cells with maximal activation of 4% to 8%, respectively, that of maximum activation obtained from the hLeptin dose response. One antibody with weak stimulation had an $EC_{50}$ value of 1.27 nM, while another of the antibodies, H4H18440P2, did not have a measurable $EC_{50}$ value. In the presence of 200 pM of hLeptin, three of the anti-LEPR antibodies that were tested demonstrated complete inhibition of Leptin in the IMR-32/STAT3-Luc/hLEPR cells with $IC_{50}$ values ranging from 723 pM (antibody H4H18457P2) to 1.83 nM (antibody H4H17322P2) or 2.9 nM (antibody H4H18464P2). Six of the anti-LEPR antibodies tested did not demonstrate any measurable inhibition in the presence of 200 pM of human Leptin. The isotype control antibody did not demonstrate any measurable stimulation of the IMR-32/STAT3-Luc/hLEPR cells in any of the assays.

TABLE 15

Activation and Inhibition of hLEPR by anti-LEPR antibodies

| | IMR-32/LEPR without human Leptin | | IMR-32/LEPR with 200 pM human Leptin | |
|---|---|---|---|---|
| Antibody | $EC_{50}$ (M) | % activation | $IC_{50}$ (M) | % inhibition |
| H4H18457P2 | N/A | N/A | 7.23E−10 | 100 |
| H4H17322P2 | 1.27E−09 | 8 | 1.83E−09 | 100 |
| H4H18464P2 | 1.30E−10 | 6 | 2.9E−09 | 100 |
| H4H18437P2 | N/A* | N/A* | N/A* | N/A* |
| H4H18439P2 | N/A* | N/A* | N/A* | N/A* |
| H4H18440P2 | IC* | 4 | N/A* | N/A* |
| H4H18462P2 | N/A* | N/A* | N/A* | N/A* |
| H4H18466P2 | N/A* | N/A* | N/A* | N/A* |
| H4H18508P2 | N/A* | N/A* | N/A* | N/A* |
| Comparator Antibody | N/A* | N/A* | 1.03E−09 | 100 |

*N/A denotes no measurable inhibition and/or activation in the assay

*IC denotes an inconclusive result in that a calculated $EC_{50}$ value could not be determined.

Example 7. Octet Cross-Competition Between Different Anti-LEPR Monoclonal Antibodies Binding competition between a panel of different anti-LEPR monoclonal antibodies was determined using a real time, label-free bio-layer interferometry assay on the Octet HTX biosensor platform (Pall ForteBio Corp.). The entire experiment was performed at 25° C. in buffer containing 10 mM HEPES, 150 mM NaCl, 3 mM EDTA, and 0.05% v/v Surfactant Tween-20, 1 mg/mL BSA, pH7.4 (HBS-EBT) with the plate shaking at the speed of 1000 rpm.

To assess whether two antibodies were able to compete with one another for binding to recombinant human LEPR expressed with a C-terminal myc-myc-hexahistidine tag (hLEPR.MMH; SEQ ID:90), about 0.25 nm of hLEPR-MMH was first captured onto anti-penta-His antibody coated Octet biosensor tips (Fortebio Inc, #18-5122) by submerging the biosensor tips for 5 minutes in wells containing 20 μg/mL of hLEPR-MMH. The antigen captured biosensor tips were then saturated with a first anti-LEPR monoclonal antibody (subsequently referred to as mAb-1) by dipping into wells containing 50 μg/mL solution of mAb-1 for 210 seconds. The biosensor tips were then subsequently dipped into wells containing a 50 μg/mL solution of a second anti-LEPR monoclonal antibody (subsequently referred to as mAb-2) for 150 seconds. The biosensor tips were washed in HBS-EBT buffer in between every step of the experiment. The real-time binding response was monitored during the entire course of the experiment and the binding response at the end of every step was recorded. The response of mAb-2 binding to hLEPR-MMH pre-complexed with mAb-1 was compared and competitive/non-competitive behavior of different anti-LEPR monoclonal antibodies was determined as shown in Table 16.

TABLE 16

Cross-competition between anti-LEPR monoclonal antibodies

| First antibody (mAb-1) binding to captured hLEPR-MMH | Second antibody (mAb-2) shown to compete with mAb-1 |
|---|---|
| H4H18439P2 | H4H18440P2 |
| H4H18440P2 | H4H18439P2 |
| H4H18457P2 | H4H18462P2 |
| | H4H18437P2 |
| | H4H18466P2 |
| | H4H18508P2 |
| H4H18462P2 | H4H18457P2 |
| | H4H18437P2 |

TABLE 16-continued

Cross-competition between anti-LEPR monoclonal antibodies

| First antibody (mAb-1) binding to captured hLEPR-MMH | Second antibody (mAb-2) shown to compete with mAb-1 |
|---|---|
| H4H18437P2 | H4H18466P2 |
| | H4H18457P2 |
| | H4H18462P2 |
| H4H18466P2 | H4H18466P2 |
| | H4H18457P2 |
| | H4H18462P2 |
| | H4H18437P2 |
| H4H17322P2 | None |
| H4H18464P2 | None |

As shown in Table 16, antibodies H4H18439P2 and H4H18440P2 compete with one another for binding to their respective epitopes. LEPR antibodies H4H18457P2, H4H18462P2, H4H18437P2, H4H18466P2 and H4H18508P2 compete with one another for binding to their respective epitopes. Antibodies H4H17322P2 and H4H18464P2 do not compete for binding to the respective epitopes of H4H18439P2, H4H18440P2, H4H18457P2, H4H18462P2, H4H18437P2, and H4H18466P2.

Example 8: In Vivo Efficacy Testing of LEPR Antagonist Antibodies in Humanized LEPR Mice The effects of three specific antagonist anti-LEPR antibodies of the invention, H4H17322P2, H4H18457P2 and H4H18464P2, on food intake, body weight and adiposity were determined in singly-housed genetically engineered LEPR$^{Hu/Hu}$ mice that express a leptin receptor which is composed of the human LEPR ectodomain sequence in place of the murine LEPR ectodomain sequence.

Figure 2:
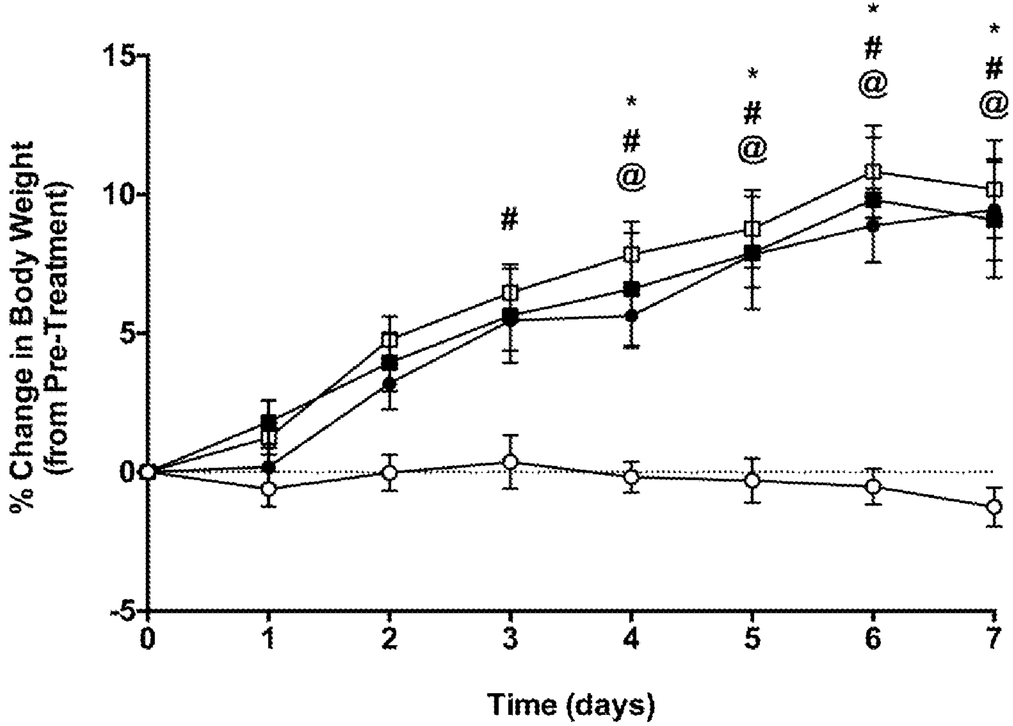
FIG. 2 shows the average percent change in body weight of mice treated with 30 mg/kg of anti-LEPR antibodies H4H17322P2, H4H18457P2, or H4H18464, or with an isotope control antibody.

Baseline daily food intake was measured between 5 days and 1 day prior to treatment (days −5 and −1). Four days prior to treatment and 6 days post treatment (days −4 and −6) body composition, including adiposity, was quantified by μCT. At day 0, thirty-two 12- to 13-week old male LEPR$^{HuHu}$ mice were randomized to four groups of 8 mice based on body weight from 1-day pretreatment (day −1). At day 0, each group received via subcutaneous injection either a single dose of isotype control antibody at 30 mg/kg, H4H17322P2 at 30 mg/kg, H4H18457P2 at 30 mg/kg, or H4H18464P2 at 30 mg/kg. The isotype control antibody does not bind any known mouse protein. Food intake and body weight were measured for the duration of the study for each animal. FIG. 1 summarizes the percent change in food intake from the average baseline daily food intake for each treatment group at each time point. The percent change in body weight from day 0 was calculated for each animal at each time point. FIG. 2 summarizes the average percent change in body weight for animals in each treatment group. FIG. 3 summarizes the average fat mass for animals in each antibody treatment group quantified by μCT 6 days prior to and 6 days following antibody treatment. All results are expressed as mean±SEM.

As shown in FIGS. 1 and 2, mice treated with the anti-LEPR antagonist antibodies demonstrated increases in percent change in food intake and percent change in body weight. These increases were not observed with the isotype control antibody treatment. As shown in FIG. 1, mice treated with H4H17322P2 at 30 mg/kg exhibited significant increases in food intake starting at one day after treatment (day 1) and at the subsequent time points compared to mice injected with isotype control antibody. Mice treated with H4H18457P2 at 30 mg/kg exhibited a significant increase in food intake starting at day 2 and at the subsequent time points compared to mice injected with isotype control antibody. Mice treated with H4H18464P2 at 30 mg/kg exhibited a significant increase in food intake starting at day 2 and at the subsequent time points, but not day 4 compared to mice injected with isotype control antibody. As shown in FIG. 2, mice treated with H4H17322P2 at 30 mg/kg exhibited a significant increase in percent body weight change starting four days after treatment (day 4) and at the subsequent time points compared to mice injected with isotype control antibody. Mice treated with H4H18457P2 at 30 mg/kg exhibited a significant increase in percent body weight change starting at day 3 and at the subsequent time points compared to mice injected with isotype control antibody. Mice treated with H4H18464P2 at 30 mg/kg exhibited a significant increase in percent body weight change starting at day 4 and at subsequent time points compared to mice injected with isotype control antibody. As depicted in FIG. 3, there were no differences in fat mass between the groups prior to treatment (day −4). Mice treated with H4H17322P2, H4H18457P2 and H4H18464P2 antibody at 30 mg/kg demonstrated a significant increase in fat mass 6 days after treatment (day 6) as compared to isotype control antibody. In conclusion, treatment with LEPR antagonist antibody, but not an isotype control antibody, increased food intake, body weight and adiposity in mice.

Example 9: Determination of Epitopes of Human LEPR to which the Anti-LEPR Antibodies of the Invention Bind To determine the epitope of human LEPR on which anti-LEPR antibodies of the invention bind, a Luminex FLEXMAP (FM3DD, LuminexCorp) flow cytometry based analysis was utilized to characterize the interaction of anti-LEPR antibodies with recombinant human LEPR protein domains. For the assay, approximately 3 million carboxylated Microplex® microspheres (Luminex, Cat #LC1000A), were washed, vortexed and sonicated in 0.1 M $NaPO_4$, pH 6.2 (activation buffer) then centrifuged to remove the supernatant. The microspheres were resuspended in 120 μl of activation buffer and the carboxylate groups (—COOH) were activated by addition of 15 μL of 50 mg/mL of N-hydroxysuccinimide (NHS, Thermo Scientific, Cat #24500) followed by addition of 15 μL of 50 mg/mL of 1-ethyl-3-[3-dimethylaminopropyl]carbodiimide (EDC, ThermoScientific, Cat #22980) at 25° C. After 10 minutes, the pH of the reaction was reduced to 5.0 with the addition of 600 μL of 50 mM MES, pH 5 (coupling buffer), and the microspheres were vortexed, and centrifuged to remove supernatant. The activated beads were immediately mixed with 500 μL of 20 μg/mL monoclonal anti-myc antibodies with either a mouse IgG or a human IgG, in coupling buffer and incubated for two hours at 25° C. The coupling reaction was quenched by addition of 50 μL of 1M Tris-HCl, pH 8.0 and the microspheres were rapidly vortexed, centrifuged, and washed four times with 1 mL of DPBS, to remove uncoupled proteins and other reaction components.

The transiently expressed LEPR proteins, included human LEPR extracellular domain expressed with a C-terminal myc-myc hexahistidine tag (human LEPR-MMH, SEQ ID NO: 89), human LEPR CRH1 (D1) expressed with a C-terminal myc-myc hexahistidine tag (human LEPR CRH1 (D1)-MMH, amino acids 1-208 of SEQ ID NO: 89 with a myc-myc hexahistidine tag, amino acids 209-236), human LEPR CRH1 (D1,D2) domain expressed with a C-terminal myc-myc hexahistidine tag (human LEPR CRH1 (D1,D2)-MMH, amino acids 1-318 of SEQ ID NO: 89 with a myc-myc hexahistidine tag, amino acids 319-346), human LEPR CRH1-Ig (D1,D2,D3) domain expressed with a C-terminal myc-myc hexahistidine tag (human LEPR CRH1 (D1,D2,D3)-MMH, amino acids 1-278 of SEQ ID NO: 89 with a myc-myc hexahistidine tag, amino acids 279-306), human LEPR CRH1-Ig (D2,D3) domain expressed with a C-terminal myc-myc hexahistidine tag (human LEPR CRH1-Ig (D2,D3)-MMH, amino acids 1-198 of SEQ ID NO: 89 with a myc-myc hexahistidine tag, amino acids 199-226), human LEPR Ig (D3) domain expressed with a C-terminal myc-myc hexahistidine tag (human LEPR Ig (D3)-MMH, amino acids 1-88 of SEQ iD NO: 89 with a myc-myc hexahistidine tag, amino acids 89-116), human LEPR CRH2 domain expressed with a C-terminal myc-myc hexahistidine tag (human LEPR CRH2-MMH, amino acids 1-207 of SEQ ID NO: 89 with a myc-myc-hexahistidine tag, amino acids 208-235), human LEPR FNIII domain expressed with a C-terminal myc-myc hexahistidine tag (human LEPR FNIII-MMH, amino acids 1-204 of SEQ ID NO: 89 with a myc-myc hexahistidine tag, amino acids 205-232), and human LEPR Ig-CRH2-FNIII domain expressed with a C-terminal myc-myc hexahistidine tag (human LEPR Ig-CRH2-FNIII-MMH, amino acids 1-510 of SEQ ID NO: 89 with a myc-myc-hexahistidine tag, amino acids 511-538), were suspended in serum free CHO-S-SFM II Medium (Thermo Fisher, Cat #31033020) and were then clarified by centrifugation. Aliquots of microspheres with immobilized anti-myc monoclonal antibodies, prepared as described above, were added individually to 1 mL of the each of these protein supernatants. The microspheres were gently mixed, incubated for two hours at 25° C., washed twice with 1 mL of DBPS, centrifuged to remove the supernatant and finally resuspended in 1 mL of DPBS buffer. Forty eight μL of anti-myc IgG coupled microspheres from individual reactions with full length human LEPR and with each of the human LEPR domain proteins were withdrawn and mixed together in 3.6 mL of PBS+20 mg/mL BSA+0.05% sodium azide (blocking buffer).

From this mixed pool, 75 μL of microspheres were plated per well on a 96 well filter plate (Millipore, Cat. No: MSBVN1250) and mixed with 25 μl of individual anti-human LEPR monoclonal antibodies (0.5 or 5 μg/mL), incubated for two hours at 25° C. and then washed twice with 200 μl of DPBS with 0.05% Tween 20 (washing buffer). To detect and quantify the amounts of bound anti-LEPR antibody levels to individual microspheres, either 100 μL of 2.5 μg/mL R-Phycoerythrin conjugated goat F(ab')2 anti-human kappa (Southern Biotech, Cat #2063-09) in blocking buffer or 100 μL of 1.25 μg/mL R-Phycoerythrin AffiniPure F(ab') in blocking buffer or 100 μl of 1.25 μg/mL R-Phycoerythrin AffiniPure F(ab')2 Fragment Goat Anti-Mouse IgG, F(ab')2 Fragment Specific (Jackson Immunoresearch, Cat. No: 115-116-072) in blocking buffer, was added and incubated for 30 minutes at 25° C. After 30 minutes, the samples were washed twice with 200 μL of washing buffer and resuspended in 150 μL of wash buffer. The Median Fluorescence intensity (MFI) of the microspheres was measured in a Luminex Analyzer.

The results of the Luminex based analysis are tabulated in Table 17. Luminex MFI signal intensities indicate that the nine anti-LEPR antibodies of the invention bound to the complete human LEPR extracellular domain. Anti-LEPR antibodies H4H18439P2 and H4H18440P2, bound to epitopes within the CRH1 D2 domain of human LEPR. Anti-LEPR antibody H4H17322P2 and COMP3551, bound to epitopes within the CRH2 domain of human LEPR. Anti-LEPR antibodies, H4H18437P2, H4H18457P2, H4H18508P2, H4H18466P2 and H4H18462P2, bound to epitopes within the FNIII domain of human LEPR. Anti-LEPR antibody, H4H18464P2 bound to epitopes within the Ig(D3) domain of human LEPR.

TABLE 17

Luminex MFI signal of anti-LEPR antibodies binding to myc tag captured full-length extracellular domain of human LEPR and isolated human LEPR domains.

| Antibody | CRH1 (D1) | CRH1 (D1, D2) | CRH1-Ig (D1, D2, D3) | CRH1-Ig (D2, D3) | Ig (D3) | CRH2 | FNIII | Ig-CRH2-FNIII | Full Length extracellular domain | Probable Binding site |
|---|---|---|---|---|---|---|---|---|---|---|
| H4H17322P2 | 14 | 50 | 31 | 58 | 26 | 19745 | 23 | 15097 | 8932 | CRH2 |
| H4H18437P2 | 21 | 82 | 34 | 43 | 26 | 25 | 1593 | 15625 | 8644 | FNIII |
| H4H18457P2 | 13 | 53 | 31 | 43 | 18 | 18 | 1187 | 13235 | 7500 | FNIII |
| H4H18508P2 | 10 | 274 | 217 | 372 | 24 | 18 | 741 | 13007 | 5865 | FNIII |
| H4H18466P2 | 15 | 56 | 209 | 76 | 26 | 17 | 457 | 11270 | 5070 | FNIII |
| H4H18439P2 | 11 | 21179 | 8021 | 10026 | 18 | 16 | 13 | 43 | 5472 | CRH1 D2 |
| H4H18440P2 | 8 | 19337 | 8245 | 9165 | 14 | 17 | 10 | 32 | 7035 | CRH1 D2 |
| H4H18464P2 | 13 | 59 | 5557 | 3742 | 27 | 24 | 23 | 15119 | 9385 | Ig(D3) |
| H4H18462P2 | 5381 | 5731 | 3961 | 47 | 21 | 24 | 581 | 14858 | 5852 | FNIII |
| H4H18462P2* | 615 | 665 | 461 | 25 | 10 | 8 | 229 | 11153 | 3610 | FNIII |
| Comparator Antibody | −14 | 19 | −57 | 27 | 10 | 9404 | 73 | 7112 | 3908 | CRH2 |

*Antibody tested at 0.5 μg/mL instead of 5 μg/mL.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

SEQUENCE LISTING

```
Sequence total quantity: 95
SEQ ID NO: 1            moltype = DNA  length = 378
FEATURE                 Location/Qualifiers
misc_feature            1..378
                        note = synthetic
source                  1..378
                        mol_type = other DNA
                        organism = synthetic construct
SEQUENCE: 1
cagctgcagc tgcaggagtc gggcccagga ctggtgaagc cttcggagac cctgtccctc  60
acctgcactg tctctggtgc ctctatcagc agtagtcgtt tctacggggg ctggatccgc  120
cagcccccag ggaagggtct ggagtggatt ggggatatct attatagtgg gaatacctac  180
tacaacccgt ccctccagag tcgagtcacc atatccgtag acacgtccaa gaatcagttc  240
tccctgaagc tgagctctgt gaccgccgca gacacggctg tgtattactg tgcgagacac  300
cttatgatta cgtttggggg acttatcgtc gagggttttg atatttgggg ccaagggaca  360
atggtcaccg tctcttca                                                378

SEQ ID NO: 2            moltype = AA  length = 126
FEATURE                 Location/Qualifiers
REGION                  1..126
                        note = synthetic
source                  1..126
                        mol_type = protein
                        organism = synthetic construct
SEQUENCE: 2
QLQLQESGPG LVKPSETLSL TCTVSGASIS SSRFYGGWIR QPPGKGLEWI GDIYYSGNTY  60
YNPSLQSRVT ISVDTSKNQF SLKLSSVTAA DTAVYYCARH LMITFGGLIV EGFDIWGQGT  120
MVTVSS                                                             126

SEQ ID NO: 3            moltype = DNA  length = 30
FEATURE                 Location/Qualifiers
misc_feature            1..30
                        note = synthetic
source                  1..30
                        mol_type = other DNA
                        organism = synthetic construct
SEQUENCE: 3
ggtgcctcta tcagcagtag tcgtttctac                                   30

SEQ ID NO: 4            moltype = AA  length = 10
FEATURE                 Location/Qualifiers
REGION                  1..10
                        note = synthetic
source                  1..10
                        mol_type = protein
                        organism = synthetic construct
SEQUENCE: 4
GASISSSRFY                                                         10

SEQ ID NO: 5            moltype = DNA  length = 21
FEATURE                 Location/Qualifiers
misc_feature            1..21
                        note = synthetic
source                  1..21
                        mol_type = other DNA
                        organism = synthetic construct
SEQUENCE: 5
atctattata gtgggaatac c                                            21

SEQ ID NO: 6            moltype = AA  length = 7
FEATURE                 Location/Qualifiers
REGION                  1..7
                        note = synthetic
source                  1..7
                        mol_type = protein
                        organism = synthetic construct
SEQUENCE: 6
IYYSGNT                                                            7
```

-continued

```
SEQ ID NO: 7           moltype = DNA  length = 54
FEATURE                Location/Qualifiers
misc_feature           1..54
                       note = synthetic
source                 1..54
                       mol_type = other DNA
                       organism = synthetic construct
SEQUENCE: 7
gcgagacacc ttatgattac gtttggggga cttatcgtcg agggttttga tatt        54

SEQ ID NO: 8           moltype = AA  length = 18
FEATURE                Location/Qualifiers
REGION                 1..18
                       note = synthetic
source                 1..18
                       mol_type = protein
                       organism = synthetic construct
SEQUENCE: 8
ARHLMITFGG LIVEGFDI                                                18

SEQ ID NO: 9           moltype = DNA  length = 324
FEATURE                Location/Qualifiers
misc_feature           1..324
                       note = synthetic
source                 1..324
                       mol_type = other DNA
                       organism = synthetic construct
SEQUENCE: 9
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 10          moltype = AA  length = 108
FEATURE                Location/Qualifiers
REGION                 1..108
                       note = synthetic
source                 1..108
                       mol_type = protein
                       organism = synthetic construct
SEQUENCE: 10
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK               108

SEQ ID NO: 11          moltype = DNA  length = 18
FEATURE                Location/Qualifiers
misc_feature           1..18
                       note = synthetic
source                 1..18
                       mol_type = other DNA
                       organism = synthetic construct
SEQUENCE: 11
cagagcatta gcagctat                                                18

SEQ ID NO: 12          moltype = AA  length = 6
FEATURE                Location/Qualifiers
REGION                 1..6
                       note = synthetic
source                 1..6
                       mol_type = protein
                       organism = synthetic construct
SEQUENCE: 12
QSISSY                                                             6

SEQ ID NO: 13          moltype =   length =
SEQUENCE: 13
000

SEQ ID NO: 14          moltype =   length =
SEQUENCE: 14
000

SEQ ID NO: 15          moltype = DNA  length = 30
FEATURE                Location/Qualifiers
misc_feature           1..30
                       note = synthetic
source                 1..30
```

```
                        mol_type = other DNA
                        organism = synthetic construct
SEQUENCE: 15
caacagagtt acagtacccc tccgatcacc                                    30

SEQ ID NO: 16           moltype = AA  length = 10
FEATURE                 Location/Qualifiers
REGION                  1..10
                        note = synthetic
source                  1..10
                        mol_type = protein
                        organism = synthetic construct
SEQUENCE: 16
QQSYSTPPIT                                                          10

SEQ ID NO: 17           moltype = DNA  length = 366
FEATURE                 Location/Qualifiers
misc_feature            1..366
                        note = synthetic
source                  1..366
                        mol_type = other DNA
                        organism = synthetic construct
SEQUENCE: 17
caggtgcagc tggtggagtc tgggggaggc gtggtccagc ctgggaggtc cctgagactc  60
tcctgtgcag cctctggatt cactttcagt agctatggca tccactgggt ccgccaggct  120
ccaggcaagg ggctggagtg ggtggcagtt atatcatatg atggaaataa taaatactat  180
gcagactccg tgaagggccg attcaccatc tccagagaca attccaagaa cacgctgtat  240
ctgcaaatga acagcctgag agctgaggac acggctgtat attactgtgc gaaagatcta  300
tttttggagt ggttatttca cggtatgggc gtctggggcc aagggaccac ggtcaccgtc  360
tcctca                                                              366

SEQ ID NO: 18           moltype = AA  length = 122
FEATURE                 Location/Qualifiers
REGION                  1..122
                        note = synthetic
source                  1..122
                        mol_type = protein
                        organism = synthetic construct
SEQUENCE: 18
QVQLVESGGG VVQPGRSLRL SCAASGFTFS SYGIHWVRQA PGKGLEWVAV ISYDGNNKYY  60
ADSVKGRFTI SRDNSKNTLY LQMNSLRAED TAVYYCAKDL FLEWLFHGMG VWGQGTTVTV  120
SS                                                                  122

SEQ ID NO: 19           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 19
ggattcactt tcagtagcta tggc                                          24

SEQ ID NO: 20           moltype = AA  length = 8
FEATURE                 Location/Qualifiers
REGION                  1..8
                        note = synthetic
source                  1..8
                        mol_type = protein
                        organism = synthetic construct
SEQUENCE: 20
GFTFSSYG                                                            8

SEQ ID NO: 21           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 21
atatcatatg atggaaataa taaa                                          24

SEQ ID NO: 22           moltype = AA  length = 8
FEATURE                 Location/Qualifiers
REGION                  1..8
                        note = synthetic
source                  1..8
                        mol_type = protein
```

```
                         organism = synthetic construct
SEQUENCE: 22
ISYDGNNK                                                                8

SEQ ID NO: 23            moltype = DNA  length = 45
FEATURE                  Location/Qualifiers
misc_feature             1..45
                         note = synthetic
source                   1..45
                         mol_type = other DNA
                         organism = synthetic construct
SEQUENCE: 23
gcgaaagatc tatttttgga gtggttattt cacggtatgg gcgtc                      45

SEQ ID NO: 24            moltype = AA  length = 15
FEATURE                  Location/Qualifiers
REGION                   1..15
                         note = synthetic
source                   1..15
                         mol_type = protein
                         organism = synthetic construct
SEQUENCE: 24
AKDLFLEWLF HGMGV                                                        15

SEQ ID NO: 25            moltype = DNA  length = 372
FEATURE                  Location/Qualifiers
misc_feature             1..372
                         note = synthetic
source                   1..372
                         mol_type = other DNA
                         organism = synthetic construct
SEQUENCE: 25
cagctgcagc tgcaggagtc gggcccagga ctagtgaagc cttcggagac cctgtccctc  60
acctgcattg tctctggtgg cgacatcacc agtagtagtt attactggaa ctggatccgc  120
cagcccccag ggaaagggct ggagtggatt gggaatatct attatagtgg aagcaccaac  180
tacaacccgt ccctcaagag tcgagtcacc atatccatag acacgtccaa gagccagttc  240
tccctgaagc tgaggtctgt gaccgccgca gacacggctg tttattactg tgcgagatta  300
ttacgatatt ttgactggtc aaaaggatac cttgactact ggggccaggg aaccctggtc  360
accgtctcct ca                                                        372

SEQ ID NO: 26            moltype = AA  length = 124
FEATURE                  Location/Qualifiers
REGION                   1..124
                         note = synthetic
source                   1..124
                         mol_type = protein
                         organism = synthetic construct
SEQUENCE: 26
QLQLQESGPG LVKPSETLSL TCIVSGGDIT SSSYYWNWIR QPPGKGLEWI GNIYYSGSTN  60
YNPSLKSRVT ISIDTSKSQF SLKLRSVTAA DTAVYYCARL LRYFDWSKGY LDYWGQGTLV  120
TVSS                                                                 124

SEQ ID NO: 27            moltype = DNA  length = 30
FEATURE                  Location/Qualifiers
misc_feature             1..30
                         note = synthetic
source                   1..30
                         mol_type = other DNA
                         organism = synthetic construct
SEQUENCE: 27
ggtggcgaca tcaccagtag tagttattac                                       30

SEQ ID NO: 28            moltype = AA  length = 10
FEATURE                  Location/Qualifiers
REGION                   1..10
                         note = synthetic
source                   1..10
                         mol_type = protein
                         organism = synthetic construct
SEQUENCE: 28
GGDITSSSYY                                                              10

SEQ ID NO: 29            moltype = DNA  length = 21
FEATURE                  Location/Qualifiers
misc_feature             1..21
                         note = synthetic
source                   1..21
                         mol_type = other DNA
                         organism = synthetic construct
```

```
SEQUENCE: 29
atctattata gtggaagcac c                                      21

SEQ ID NO: 30          moltype = AA  length = 7
FEATURE                Location/Qualifiers
REGION                 1..7
                       note = synthetic
source                 1..7
                       mol_type = protein
                       organism = synthetic construct
SEQUENCE: 30
IYYSGST                                                      7

SEQ ID NO: 31          moltype = DNA  length = 48
FEATURE                Location/Qualifiers
misc_feature           1..48
                       note = synthetic
source                 1..48
                       mol_type = other DNA
                       organism = synthetic construct
SEQUENCE: 31
gcgagattat tacgatattt tgactggtca aaaggatacc ttgactac         48

SEQ ID NO: 32          moltype = AA  length = 16
FEATURE                Location/Qualifiers
REGION                 1..16
                       note = synthetic
source                 1..16
                       mol_type = protein
                       organism = synthetic construct
SEQUENCE: 32
ARLLRYFDWS KGYLDY                                            16

SEQ ID NO: 33          moltype = DNA  length = 369
FEATURE                Location/Qualifiers
misc_feature           1..369
                       note = synthetic
source                 1..369
                       mol_type = other DNA
                       organism = synthetic construct
SEQUENCE: 33
caggtgcagc tggtggagtc tgggggaggc atggtcaagc ctggagggtc cctgagactc  60
tcctgtgcag cctctggatt caccttcagt gactactata tgagctggat ccgccaggct  120
ccagggaagg gtctggagtg gatttcacac attagtatta ctggtagcac catatactac  180
gcagactctg tgaagggccg attcaccatc tccagggaca acgccaagaa ttcactgtat  240
ttggaaatga acagactgag agacgaggac acggccgtat attactgtac gagagatgag  300
ccggatattg tactagtaag gtacggtatg gacgtctggg gccaagggac cacggtcacc  360
gtctcctca                                                    369

SEQ ID NO: 34          moltype = AA  length = 123
FEATURE                Location/Qualifiers
REGION                 1..123
                       note = synthetic
source                 1..123
                       mol_type = protein
                       organism = synthetic construct
SEQUENCE: 34
QVQLVESGGG MVKPGGSLRL SCAASGFTFS DYYMSWIRQA PGKGLEWISH ISITGSTIYY  60
ADSVKGRFTI SRDNAKNSLY LEMNRLRDED TAVYYCTRDE PDIVLVRYGM DVWGQGTTVT  120
VSS                                                          123

SEQ ID NO: 35          moltype = DNA  length = 24
FEATURE                Location/Qualifiers
misc_feature           1..24
                       note = synthetic
source                 1..24
                       mol_type = other DNA
                       organism = synthetic construct
SEQUENCE: 35
ggattcacct tcagtgacta ctat                                   24

SEQ ID NO: 36          moltype = AA  length = 8
FEATURE                Location/Qualifiers
REGION                 1..8
                       note = synthetic
source                 1..8
                       mol_type = protein
                       organism = synthetic construct
SEQUENCE: 36
```

```
GFTFSDYY                                                          8

SEQ ID NO: 37          moltype = DNA  length = 24
FEATURE                Location/Qualifiers
misc_feature           1..24
                       note = synthetic
source                 1..24
                       mol_type = other DNA
                       organism = synthetic construct
SEQUENCE: 37
attagtatta ctggtagcac cata                                        24

SEQ ID NO: 38          moltype = AA  length = 8
FEATURE                Location/Qualifiers
REGION                 1..8
                       note = synthetic
source                 1..8
                       mol_type = protein
                       organism = synthetic construct
SEQUENCE: 38
ISITGSTI                                                          8

SEQ ID NO: 39          moltype = DNA  length = 48
FEATURE                Location/Qualifiers
misc_feature           1..48
                       note = synthetic
source                 1..48
                       mol_type = other DNA
                       organism = synthetic construct
SEQUENCE: 39
acgagagatg agccggatat tgtactagta aggtacggta tggacgtc              48

SEQ ID NO: 40          moltype = AA  length = 16
FEATURE                Location/Qualifiers
REGION                 1..16
                       note = synthetic
source                 1..16
                       mol_type = protein
                       organism = synthetic construct
SEQUENCE: 40
TRDEPDIVLV RYGMDV                                                 16

SEQ ID NO: 41          moltype = DNA  length = 351
FEATURE                Location/Qualifiers
misc_feature           1..351
                       note = synthetic
source                 1..351
                       mol_type = other DNA
                       organism = synthetic construct
SEQUENCE: 41
gaggtgcagc tggtggagtc tgggggaagt gtggtacggc ctggggaatc cctgagactc  60
tcctgtgcag cctctggatt cacatttgat gattatggca tgagctgggt ccgccaagct  120
ccagggaagg ggctggagtg ggtctctggt attagttgga atggtggcat cacagtttat  180
gcagactctg tgaagggccg attcaccgtc tccagagaca acgccaagaa ctccctgtat  240
ctgcaaatga acagtctgag agccgaggac acggccctct atcactgtgc gagagcccgt  300
tatggtggcg ccgactactg gggccaggga accctggtca ccgtctcctc a           351

SEQ ID NO: 42          moltype = AA  length = 117
FEATURE                Location/Qualifiers
REGION                 1..117
                       note = synthetic
source                 1..117
                       mol_type = protein
                       organism = synthetic construct
SEQUENCE: 42
EVQLVESGGS VVRPGESLRL SCAASGFTFD DYGMSWVRQA PGKGLEWVSG ISWNGGITVY  60
ADSVKGRFTV SRDNAKNSLY LQMNSLRAED TALYHCARAR YGGADYWGQG TLVTVSS     117

SEQ ID NO: 43          moltype = DNA  length = 24
FEATURE                Location/Qualifiers
misc_feature           1..24
                       note = synthetic
source                 1..24
                       mol_type = other DNA
                       organism = synthetic construct
SEQUENCE: 43
ggattcacat ttgatgatta tggc                                        24

SEQ ID NO: 44          moltype = AA  length = 8
```

```
FEATURE                Location/Qualifiers
REGION                 1..8
                       note = synthetic
source                 1..8
                       mol_type = protein
                       organism = synthetic construct
SEQUENCE: 44
GFTFDDYG                                                           8

SEQ ID NO: 45          moltype = DNA  length = 24
FEATURE                Location/Qualifiers
misc_feature           1..24
                       note = synthetic
source                 1..24
                       mol_type = other DNA
                       organism = synthetic construct
SEQUENCE: 45
attagttgga atggtggcat caca                                         24

SEQ ID NO: 46          moltype = AA  length = 8
FEATURE                Location/Qualifiers
REGION                 1..8
                       note = synthetic
source                 1..8
                       mol_type = protein
                       organism = synthetic construct
SEQUENCE: 46
ISWNGGIT                                                           8

SEQ ID NO: 47          moltype = DNA  length = 30
FEATURE                Location/Qualifiers
misc_feature           1..30
                       note = synthetic
source                 1..30
                       mol_type = other DNA
                       organism = synthetic construct
SEQUENCE: 47
gcgagagccc gttatggtgg cgccgactac                                   30

SEQ ID NO: 48          moltype = AA  length = 10
FEATURE                Location/Qualifiers
REGION                 1..10
                       note = synthetic
source                 1..10
                       mol_type = protein
                       organism = synthetic construct
SEQUENCE: 48
ARARYGGADY                                                         10

SEQ ID NO: 49          moltype = DNA  length = 366
FEATURE                Location/Qualifiers
misc_feature           1..366
                       note = synthetic
source                 1..366
                       mol_type = other DNA
                       organism = synthetic construct
SEQUENCE: 49
gaggtgcagc tggtggagtc tgggggagac ttggtacagc ctgggcggtc cctgagactc  60
tcctgtgcag cctctggatt cacctttagc agttttgcca tgagctgggt ccgccaggct  120
ccagggaggg gactggagtg ggtctcaagt ctcagtgata gtggtgataa cacatactac  180
gcagactccg tgaagggccg gttcaccatc tccagagaca attccaaaaa tacgttgtat  240
ctgcaaatga acaacctgag agccgaggac acggccgttt attactgtgc gaaagatctc  300
ttttcggggt ggttattcca tggttttgat gtctggggcc aagggacaat ggtcaccgtc  360
tcttca                                                             366

SEQ ID NO: 50          moltype = AA  length = 122
FEATURE                Location/Qualifiers
REGION                 1..122
                       note = synthetic
source                 1..122
                       mol_type = protein
                       organism = synthetic construct
SEQUENCE: 50
EVQLVESGGD LVQPGRSLRL SCAASGFTFS SFAMSWVRQA PGRGLEWVSS LSDSGDNTYY  60
ADSVKGRFTI SRDNSKNTLY LQMNNLRAED TAVYYCAKDL FSGWLFHGFD VWGQGTMVTV  120
SS                                                                 122

SEQ ID NO: 51          moltype = DNA  length = 24
FEATURE                Location/Qualifiers
```

```
misc_feature          1..24
                      note = synthetic
source                1..24
                      mol_type = other DNA
                      organism = synthetic construct
SEQUENCE: 51
ggattcacct ttagcagttt tgcc                                    24

SEQ ID NO: 52         moltype = AA  length = 8
FEATURE               Location/Qualifiers
REGION                1..8
                      note = synthetic
source                1..8
                      mol_type = protein
                      organism = synthetic construct
SEQUENCE: 52
GFTFSSFA                                                      8

SEQ ID NO: 53         moltype = DNA  length = 24
FEATURE               Location/Qualifiers
misc_feature          1..24
                      note = synthetic
source                1..24
                      mol_type = other DNA
                      organism = synthetic construct
SEQUENCE: 53
ctcagtgata gtggtgataa caca                                    24

SEQ ID NO: 54         moltype = AA  length = 8
FEATURE               Location/Qualifiers
REGION                1..8
                      note = synthetic
source                1..8
                      mol_type = protein
                      organism = synthetic construct
SEQUENCE: 54
LSDSGDNT                                                      8

SEQ ID NO: 55         moltype = DNA  length = 45
FEATURE               Location/Qualifiers
misc_feature          1..45
                      note = synthetic
source                1..45
                      mol_type = other DNA
                      organism = synthetic construct
SEQUENCE: 55
gcgaaagatc tcttttcggg gtggttattc catggttttg atgtc             45

SEQ ID NO: 56         moltype = AA  length = 15
FEATURE               Location/Qualifiers
REGION                1..15
                      note = synthetic
source                1..15
                      mol_type = protein
                      organism = synthetic construct
SEQUENCE: 56
AKDLFSGWLF HGFDV                                              15

SEQ ID NO: 57         moltype = DNA  length = 351
FEATURE               Location/Qualifiers
misc_feature          1..351
                      note = synthetic
source                1..351
                      mol_type = other DNA
                      organism = synthetic construct
SEQUENCE: 57
caggttcagc tggtgcagtc tggacctgaa gtgaaaaaac ctggggcctc agtgaaggtc  60
tcttgtaagg gttctggtta caccttttcc tggtatggaa tcagctggat ccgacaggcc  120
cctggacacg gccttgaatg gatgggatgg atcagcgctt ccagtggtaa tacaagattt  180
gcacagaagg tccagggcag actcaccatg accacagaca catcgacgag tacagcctac  240
atggagctga ggagcctgag atctgacgac acggccgttt attactgtgc gagaacgggg  300
actcggccct ttgactattg gggccaggga accctggtca ccgtctcctc a           351

SEQ ID NO: 58         moltype = AA  length = 117
FEATURE               Location/Qualifiers
REGION                1..117
                      note = synthetic
source                1..117
                      mol_type = protein
```

```
                         organism = synthetic construct
SEQUENCE: 58
QVQLVQSGPE VKKPGASVKV SCKGSGYTFS WYGISWIRQA PGHGLEWMGW ISASSGNTRF  60
AQKVQGRLTM TTDTSTSTAY MELRSLRSDD TAVYYCARTG TRPFDYWGQG TLVTVSS     117

SEQ ID NO: 59            moltype = DNA  length = 24
FEATURE                  Location/Qualifiers
misc_feature             1..24
                         note = synthetic
source                   1..24
                         mol_type = other DNA
                         organism = synthetic construct
SEQUENCE: 59
ggttacacct tttcctggta tgga                                        24

SEQ ID NO: 60            moltype = AA  length = 8
FEATURE                  Location/Qualifiers
REGION                   1..8
                         note = synthetic
source                   1..8
                         mol_type = protein
                         organism = synthetic construct
SEQUENCE: 60
GYTFSWYG                                                          8

SEQ ID NO: 61            moltype = DNA  length = 24
FEATURE                  Location/Qualifiers
misc_feature             1..24
                         note = synthetic
source                   1..24
                         mol_type = other DNA
                         organism = synthetic construct
SEQUENCE: 61
atcagcgctt ccagtggtaa taca                                        24

SEQ ID NO: 62            moltype = AA  length = 8
FEATURE                  Location/Qualifiers
REGION                   1..8
                         note = synthetic
source                   1..8
                         mol_type = protein
                         organism = synthetic construct
SEQUENCE: 62
ISASSGNT                                                          8

SEQ ID NO: 63            moltype = DNA  length = 30
FEATURE                  Location/Qualifiers
misc_feature             1..30
                         note = synthetic
source                   1..30
                         mol_type = other DNA
                         organism = synthetic construct
SEQUENCE: 63
gcgagaacgg ggactcggcc ctttgactat                                  30

SEQ ID NO: 64            moltype = AA  length = 10
FEATURE                  Location/Qualifiers
REGION                   1..10
                         note = synthetic
source                   1..10
                         mol_type = protein
                         organism = synthetic construct
SEQUENCE: 64
ARTGTRPFDY                                                        10

SEQ ID NO: 65            moltype = DNA  length = 366
FEATURE                  Location/Qualifiers
misc_feature             1..366
                         note = synthetic
source                   1..366
                         mol_type = other DNA
                         organism = synthetic construct
SEQUENCE: 65
gaggtgcagc tggtggagtc tgggggaggc ttggtccagc cggggggggtc cctgagactc  60
tcctgtacag cctctggatt caccttcagt agctatggtc tgcactgggt ccgccaggct  120
ccagggaagg gactggaata tgtttcaagt attaatcata atgggggtag taaatattat  180
gcagactctg tgaagggcag attcaccatc tccagagaca attcgaagaa cacgctgttt  240
cttcaaatgg gcagcctgaa aactgaggac atggctgttt attactgtgc gagagatctc  300
tttttggagt ggttattcca tggttttgat atctggggcc aagggacaat ggtcaccgtc  360
```

-continued

```
tcttca                                                          366

SEQ ID NO: 66          moltype = AA  length = 122
FEATURE                Location/Qualifiers
REGION                 1..122
                       note = synthetic
source                 1..122
                       mol_type = protein
                       organism = synthetic construct
SEQUENCE: 66
EVQLVESGGG LVQPGGSLRL SCTASGFTFS SYGLHWVRQA PGKGLEYVSS INHNGGSKYY  60
ADSVKGRFTI SRDNSKNTLF LQMGSLKTED MAVYYCARDL FLEWLFHGFD IWGQGTMVTV  120
SS                                                              122

SEQ ID NO: 67          moltype = DNA  length = 24
FEATURE                Location/Qualifiers
misc_feature           1..24
                       note = synthetic
source                 1..24
                       mol_type = other DNA
                       organism = synthetic construct
SEQUENCE: 67
ggattcacct tcagtagcta tggt                                      24

SEQ ID NO: 68          moltype = AA  length = 8
FEATURE                Location/Qualifiers
REGION                 1..8
                       note = synthetic
source                 1..8
                       mol_type = protein
                       organism = synthetic construct
SEQUENCE: 68
GFTFSSYG                                                        8

SEQ ID NO: 69          moltype = DNA  length = 24
FEATURE                Location/Qualifiers
misc_feature           1..24
                       note = synthetic
source                 1..24
                       mol_type = other DNA
                       organism = synthetic construct
SEQUENCE: 69
attaatcata atgggggtag taaa                                      24

SEQ ID NO: 70          moltype = AA  length = 8
FEATURE                Location/Qualifiers
REGION                 1..8
                       note = synthetic
source                 1..8
                       mol_type = protein
                       organism = synthetic construct
SEQUENCE: 70
INHNGGSK                                                        8

SEQ ID NO: 71          moltype = DNA  length = 45
FEATURE                Location/Qualifiers
misc_feature           1..45
                       note = synthetic
source                 1..45
                       mol_type = other DNA
                       organism = synthetic construct
SEQUENCE: 71
gcgagagatc tctttttgga gtggttattc catggttttg atatc               45

SEQ ID NO: 72          moltype = AA  length = 15
FEATURE                Location/Qualifiers
REGION                 1..15
                       note = synthetic
source                 1..15
                       mol_type = protein
                       organism = synthetic construct
SEQUENCE: 72
ARDLFLEWLF HGFDI                                                15

SEQ ID NO: 73          moltype = DNA  length = 357
FEATURE                Location/Qualifiers
misc_feature           1..357
                       note = synthetic
source                 1..357
```

```
                        mol_type = other DNA
                        organism = synthetic construct
SEQUENCE: 73
caggtgcagc tgcaggagtc gggcccagga ctggtgaagc cttcacagac cctgtccctc  60
acctgttctg tctctggtgg ctccataaac actggttctt acttctggac ttggatccgc  120
cagcacccag ggagggcct ggagtggatt gggtacatct attacaatgg agacacctac  180
tacaatccgt ccctcaagag tcgagttacc ttatcactag acacgtctaa gaaccagttc  240
tccctgaagc tgaactctct gactgccggg gacacggccg tttattactg tgcgagaagt  300
gactggaact ccctttttga ccactggggc caggggaccc tggtcaccgt ctcctca    357

SEQ ID NO: 74           moltype = AA  length = 119
FEATURE                 Location/Qualifiers
REGION                  1..119
                        note = synthetic
source                  1..119
                        mol_type = protein
                        organism = synthetic construct
SEQUENCE: 74
QVQLQESGPG LVKPSQTLSL TCSVSGGSIN TGSYFWTWIR QHPGEGLEWI GYIYYNGDTY  60
YNPSLKSRVT LSLDTSKNQF SLKLNSLTAG DTAVYYCARS DWNSLFDHWG QGTLVTVSS   119

SEQ ID NO: 75           moltype = DNA  length = 30
FEATURE                 Location/Qualifiers
misc_feature            1..30
                        note = synthetic
source                  1..30
                        mol_type = other DNA
                        organism = synthetic construct
SEQUENCE: 75
ggtggctcca taaacactgg ttcttacttc                                  30

SEQ ID NO: 76           moltype = AA  length = 10
FEATURE                 Location/Qualifiers
REGION                  1..10
                        note = synthetic
source                  1..10
                        mol_type = protein
                        organism = synthetic construct
SEQUENCE: 76
GGSINTGSYF                                                        10

SEQ ID NO: 77           moltype = DNA  length = 21
FEATURE                 Location/Qualifiers
misc_feature            1..21
                        note = synthetic
source                  1..21
                        mol_type = other DNA
                        organism = synthetic construct
SEQUENCE: 77
atctattaca atggagacac c                                           21

SEQ ID NO: 78           moltype = AA  length = 7
FEATURE                 Location/Qualifiers
REGION                  1..7
                        note = synthetic
source                  1..7
                        mol_type = protein
                        organism = synthetic construct
SEQUENCE: 78
IYYNGDT                                                           7

SEQ ID NO: 79           moltype = DNA  length = 33
FEATURE                 Location/Qualifiers
misc_feature            1..33
                        note = synthetic
source                  1..33
                        mol_type = other DNA
                        organism = synthetic construct
SEQUENCE: 79
gcgagaagtg actggaactc cctttttgac cac                              33

SEQ ID NO: 80           moltype = AA  length = 11
FEATURE                 Location/Qualifiers
REGION                  1..11
                        note = synthetic
source                  1..11
                        mol_type = protein
                        organism = synthetic construct
SEQUENCE: 80
```

```
ARSDWNSLFD H                                                    11

SEQ ID NO: 81           moltype = DNA  length = 324
FEATURE                 Location/Qualifiers
misc_feature            1..324
                        note = synthetic
source                  1..324
                        mol_type = other DNA
                        organism = synthetic construct
SEQUENCE: 81
gaaattgtgt tgacgcagtc tccaggcacc ctgtctttgt ctccagggga aagagccacc  60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                      324

SEQ ID NO: 82           moltype = AA  length = 108
FEATURE                 Location/Qualifiers
REGION                  1..108
                        note = synthetic
source                  1..108
                        mol_type = protein
                        organism = synthetic construct
SEQUENCE: 82
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK              108

SEQ ID NO: 83           moltype = DNA  length = 21
FEATURE                 Location/Qualifiers
misc_feature            1..21
                        note = synthetic
source                  1..21
                        mol_type = other DNA
                        organism = synthetic construct
SEQUENCE: 83
cagagtgtta gcagcagcta c                                         21

SEQ ID NO: 84           moltype = AA  length = 7
FEATURE                 Location/Qualifiers
REGION                  1..7
                        note = synthetic
source                  1..7
                        mol_type = protein
                        organism = synthetic construct
SEQUENCE: 84
QSVSSSY                                                         7

SEQ ID NO: 85           moltype =   length =
SEQUENCE: 85
000

SEQ ID NO: 86           moltype =   length =
SEQUENCE: 86
000

SEQ ID NO: 87           moltype = DNA  length = 27
FEATURE                 Location/Qualifiers
misc_feature            1..27
                        note = synthetic
source                  1..27
                        mol_type = other DNA
                        organism = synthetic construct
SEQUENCE: 87
cagcagtatg gtagctcacc ttggacg                                   27

SEQ ID NO: 88           moltype = AA  length = 9
FEATURE                 Location/Qualifiers
REGION                  1..9
                        note = synthetic
source                  1..9
                        mol_type = protein
                        organism = synthetic construct
SEQUENCE: 88
QQYGSSPWT                                                       9

SEQ ID NO: 89           moltype = AA  length = 1165
FEATURE                 Location/Qualifiers
REGION                  1..1165
```

```
                         note = hLEPR P48357
source                   1..1165
                         mol_type = protein
                         organism = synthetic construct
SEQUENCE: 89
MICQKFCVVL LHWEFIYVIT AFNLSYPITP WRFKLSCMPP NSTYDYFLLP AGLSKNTSNS  60
NGHYETAVEP KFNSSGTHFS NLSKTTFHCC FRSEQDRNCS LCADNIEGKT FVSTVNSLVF  120
QQIDANWNIQ CWLKGDLKLF ICYVESLFKN LFRNYNYKVH LLYVLPEVLE DSPLVPQKGS  180
FQMVHCNCSV HECCECLVPV PTAKLNDTLL MCLKITSGGV IFQSPLMSVQ PINMVKPDPP  240
LGLHMEITDD GNLKISWSSP PLVPFPLQYQ VKYSENSTTV IREADKIVSA TSLLVDSILP  300
GSSYEVQVRG KRLDGPGIWS DWSTPRVFTT QDVIYFPPKI LTSVGSNVSF HCIYKKENKI  360
VPSKEIVWWM NLAEKIPQSQ YDVVSDHVSK VTFFNLNETK PRGKFTYDAV YCCNEHECHH  420
RYAELYVIDV NINISCETDG YLTKMTCRWS TSTIQSLAES TLQLRYHRSS LYCSDIPSIH  480
PISEPKDCYL QSDGFYECIF QPIFLLSGYT MWIRINHSLG SLDSPPTCVL PDSVVKPLPP  540
SSVKAEITIN IGLLKISWEK PVFPENNLQF QIRYGLSGKE VQWKMYEVYD AKSKSVSLPV  600
PDLCAVYAVQ VRCKRLDGLG YWSNWSNPAY TVVMDIKVPM RGPEFWRIIN GDTMKKEKNV  660
TLLWKPLMKN DSLCSVQRYV INHHTSCNGT WSEDVGNHTK FTFLWTEQAH TVTVLAINSI  720
GASVANFNLT FSWPMSKVNI VQSLSAYPLN SSCVIVSWIL SPSDYKLMYF IIEWKNLNED  780
GEIKWLRISS SVKKYYIHDH FIPIEKYQFS LYPIFMEGVG KPKIINSFTQ DDIEKHQSDA  840
GLYVIVPVII SSSILLLGTL LISHQRMKKL FWEDVPNPKN CSWAQGLNFQ KPETFEHLFI  900
KHTASVTCGP LLLEPETISE DISVDTSWKN KDEMMPTTVV SLLSTTDLEK GSVCISDQFN  960
SVNFSEAEGT EVTYEDESQR QPFVKYATLI SNSKPSETGE EQGLINSSVT KCFSSKNSPL  1020
KDSFSNSSWE IEAQAFFILS DQHPNIISPH LTFSEGLDEL LKLEGNFPEE NNDKKSIYYL  1080
GVTSIKKRES GVLLTDKSRV SCPFPAPCLF TDIRVLQDSC SHFVENNINL GTSSKKTFAS  1140
YMPQFQTCST QTHKIMENKM CDLTV                                       1165

SEQ ID NO: 90            moltype = AA  length = 846
FEATURE                  Location/Qualifiers
REGION                   1..846
                         note = hLEPR-mmh aa 1-818: F22-D839 of P48357 aa
                          819-846:myc-myc-hexahistidine tag
source                   1..846
                         mol_type = protein
                         organism = synthetic construct
SEQUENCE: 90
FNLSYPITPW RFKLSCMPPN STYDYFLLPA GLSKNTSNSN GHYETAVEPK FNSSGTHFSN  60
LSKTTFHCCF RSEQDRNCSL CADNIEGKTF VSTVNSLVFQ QIDANWNIQC WLKGDLKLFI  120
CYVESLFKNL FRNYNYKVHL LYVLPEVLED SPLVPQKGSF QMVHCNCSVH ECCECLVPVP  180
TAKLNDTLLM CLKITSGGVI FQSPLMSVQP INMVKPDPPL GLHMEITDDG NLKISWSSPP  240
LVPFPLQYQV KYSENSTTVI READKIVSAT SLLVDSILPG SSYEVQVRGK RLDGPGIWSD  300
WSTPRVFTTQ DVIYFPPKIL TSVGSNVSFH CIYKKENKIV PSKEIVWWMN LAEKIPQSQY  360
DVVSDHVSKV TFFNLNETKP RGKFTYDAVY CCNEHECHHR YAELYVIDVN INISCETDGY  420
LTKMTCRWST STIQSLAEST LQLRYHRSSL YCSDIPSIHP ISEPKDCYLQ SDGFYECIFQ  480
PIFLLSGYTM WIRINHSLGS LDSPPTCVLP DSVVKPLPPS SVKAEITINI GLLKISWEKP  540
VFPENNLQFQ IRYGLSGKEV QWKMYEVYDA KSKSVSLPVP DLCAVYAVQV RCKRLDGLGY  600
WSNWSNPAYT VVMDIKVPMR GPEFWRIING DTMKKEKNVT LLWKPLMKND SLCSVQRYVI  660
NHHTSCNGTW SEDVGNHTKF TFLWTEQAHT VTVLAINSIG ASVANFNLTF SWPMSKVNIV  720
QSLSAYPLNS SCVIVSWILS PSDYKLMYFI IEWKNLNEDG EIKWLRISSS VKKYYIHDHF  780
IPIEKYQFSL YPIFMEGVGK PKIINSFTQD DIEKHQSDEQ KLISEEDLGG EQKLISEEDL  840
HHHHHH                                                            846

SEQ ID NO: 91            moltype = AA  length = 1051
FEATURE                  Location/Qualifiers
REGION                   1..1051
                         note = hLEPR-mFc aa 1-818: F22-D839 of P48357 aa 819-1051:
                          mouse IgG2a(E98-K330 of P01863)
source                   1..1051
                         mol_type = protein
                         organism = synthetic construct
SEQUENCE: 91
FNLSYPITPW RFKLSCMPPN STYDYFLLPA GLSKNTSNSN GHYETAVEPK FNSSGTHFSN  60
LSKTTFHCCF RSEQDRNCSL CADNIEGKTF VSTVNSLVFQ QIDANWNIQC WLKGDLKLFI  120
CYVESLFKNL FRNYNYKVHL LYVLPEVLED SPLVPQKGSF QMVHCNCSVH ECCECLVPVP  180
TAKLNDTLLM CLKITSGGVI FQSPLMSVQP INMVKPDPPL GLHMEITDDG NLKISWSSPP  240
LVPFPLQYQV KYSENSTTVI READKIVSAT SLLVDSILPG SSYEVQVRGK RLDGPGIWSD  300
WSTPRVFTTQ DVIYFPPKIL TSVGSNVSFH CIYKKENKIV PSKEIVWWMN LAEKIPQSQY  360
DVVSDHVSKV TFFNLNETKP RGKFTYDAVY CCNEHECHHR YAELYVIDVN INISCETDGY  420
LTKMTCRWST STIQSLAEST LQLRYHRSSL YCSDIPSIHP ISEPKDCYLQ SDGFYECIFQ  480
PIFLLSGYTM WIRINHSLGS LDSPPTCVLP DSVVKPLPPS SVKAEITINI GLLKISWEKP  540
VFPENNLQFQ IRYGLSGKEV QWKMYEVYDA KSKSVSLPVP DLCAVYAVQV RCKRLDGLGY  600
WSNWSNPAYT VVMDIKVPMR GPEFWRIING DTMKKEKNVT LLWKPLMKND SLCSVQRYVI  660
NHHTSCNGTW SEDVGNHTKF TFLWTEQAHT VTVLAINSIG ASVANFNLTF SWPMSKVNIV  720
QSLSAYPLNS SCVIVSWILS PSDYKLMYFI IEWKNLNEDG EIKWLRISSS VKKYYIHDHF  780
IPIEKYQFSL YPIFMEGVGK PKIINSFTQD DIEKHQSDEP RGPTIKPCPP CKCPAPNLLG  840
GPSVFIFPPK IKDVLMISLS PIVTCVVVDV SEDDPDVQIS WFVNNVEVHT AQTQTHREDY  900
NSTLRVVSAL PIQHQDWMSG KEFKCKVNNK DLPAPIERTI SKPKGSVRAP QVYVLPPPEE  960
EMTKKQVTLT CMVTDFMPED IYVEWTNNGK TELNYKNTEP VLDSDGSYFM YSKLRVEKKN  1020
WVERNSYSCS VVHEGLHNHH TTKSFSRTPG K                                1051
```

```
SEQ ID NO: 92           moltype = AA  length = 1045
FEATURE                 Location/Qualifiers
REGION                  1..1045
                        note = hLEPR-hFc aa 1-818: F22-D839 of P48357 aa 819-1045:
                         human IgG1(D104-K330 of P01857)
source                  1..1045
                        mol_type = protein
                        organism = synthetic construct
SEQUENCE: 92
FNLSYPITPW RFKLSCMPPN STYDYFLLPA GLSKNTSNSN GHYETAVEPK FNSSGTHFSN  60
LSKTTFHCCF RSEQDRNCSL CADNIEGKTF VSTVNSLVFQ QIDANWNIQC WLKGDLKLFI  120
CYVESLFKNL FRNYNYKVHL LYVLPEVLED SPLVPQKGSF QMVHCNCSVH ECCECLVPVP  180
TAKLNDTLLM CLKITSGGVI FQSPLMSVQP INMVKPDPPL GLHMEITDDG NLKISWSSPP  240
LVPFPLQYQV KYSENSTTVI READKIVSAT SLLVDSILPG SSYEVQVRGK RLDGPGIWSD  300
WSTPRVFTTQ DVIYFPPKIL TSVGSNVSFH CIYKKENKIV PSKEIVWWMN LAEKIPQSQY  360
DVVSDHVSKV TFFNLNETKP RGKFTYDAVY CCNEHECHHR YAELYVIDVN INISCETDGY  420
LTKMTCRWST STIQSLAEST LQLRYHRSSL YCSDIPSIHP ISEPKDCYLQ SDGFYECIFQ  480
PIFLLSGYTM WIRINHSLGS LDSPPTCVLP DSVVKPLPPS SVKAEITINI GLLKISWEKP  540
VFPENNLQFQ IRYGLSGKEV QWKMYEVYDA KSKSVSLPVP DLCAVYAVQV RCKRLDGLGY  600
WSNWSNPAYT VVMDIKVPMR GPEFWRIING DTMKKEKNVT LLWKPLMKND SLCSVQRYVI  660
NHHTSCNGTW SEDVGNHTKF TFLWTEQAHT VTVLAINSIG ASVANFNLTF SWPMSKVNIV  720
QSLSAYPLNS SCVIVSWILS PSDYKLMYFI IEWKNLNEDG EIKWLRISSS VKKYYIHDHF  780
IPIEKYQFSL YPIFMEGVGK PKIINSFTQD DIEKHQSDDK THTCPPCPAP ELLGGPSVFL  840
FPPKPKDTLM ISRTPEVTCV VVDVSHEDPE VKFNWYVDGV EVHNAKTKPR EEQYNSTYRV  900
VSVLTVLHQD WLNGKEYKCK VSNKALPAPI EKTISKAKGQ PREPQVYTLP PSRDELTKNQ  960
VSLTCLVKGF YPSDIAVEWE SNGQPENNYK TTPPVLDSDG SFFLYSKLTV DKSRWQQGNV  1020
FSCSVMHEAL HNHYTQKSLS LSPGK                                        1045

SEQ ID NO: 93           moltype = AA  length = 844
FEATURE                 Location/Qualifiers
REGION                  1..844
                        note = MfLEPR-mmh aa 1-816: Macaca fascicularis LEPR
                         (F22-D837 ofXP_005543194.1 with a T827A substitution) aa
                         817-844:myc-myc-hexahistidine tag
source                  1..844
                        mol_type = protein
                        organism = synthetic construct
SEQUENCE: 93
FNLSYPITPW RFKLSCMPPN STYDYFLLPA GLSKNTSNLN GHYETAVEFN SSDTHFSNLS  60
KTTFHCCFRS EQDRNCSLCA DNIEGKTFVS TVNSSVFQQM GANWNIQCWL KGDLKLFICY  120
VESLFKNPFK NYKHKVHLLY VLPEVLEDSP LVPQKGSFQM VHCNCSVHER CECLVPVPTA  180
KLNDTLLMCL KITSGGVIFQ SPLMSVQPIN MVKPDPPLGL RMEITDDGNL KISWSSPPLV  240
PFPLQYEVKY SENSTTVIRE ADKIVSATSL LVDGILPGSS YEVQVRGKRL DGPGIWSDWS  300
TPHVFTTQDV IYFPPKILTS VGSNVSFHCI YKNENKIVSS KKIVWWMNLA EKIPQSQYDV  360
VSDHVSKVTF FNLNETKPRG KFTYDAVYCC NEHECHHRYA ELYVIDVNIN ISCETDGHLT  420
KMTCRWSTNT IQSLAGSTLQ LRYRRSSLYC FDIPSIHPIS KPKDCYLQSD GFYECVFQPI  480
FLLSGYTMWI RINHPLGSLD SPPTCVLPDS VVKPLPPSSV KAEIIKNIGL LKISWEKPVF  540
PENNLQFQIR YGLSGKEIQW KMYDVYDAKS KSVSLPVPDF CAVYAVQVRC KRSDGLGLWS  600
NWSNPAYTVV MDIKVPMRGP EFWRIINGDT MKKEKNVTLL WKPLMKNDSL CSVQRYVINH  660
HTSCNGTWSE DVGNHTKFTF LWTEQAHTVT VLAINSIGAS VANFNLTFSW PMSKVNIVQS  720
LSAYPLNSSC VILSWILSPS DYKLMYFIIE WKNLNEDGEI KWLRISSSVK KYYIHDHFIP  780
IEKYQFSLYP IFMEGVGKPK IINSFAQDNT EKHQNDEQKL ISEEDLGGEQ KLISEEDLHH  840
HHHH                                                               844

SEQ ID NO: 94           moltype = AA  length = 846
FEATURE                 Location/Qualifiers
REGION                  1..846
                        note = mLEPR-mmh aa 1-818: mouse LEPR (L22-G839 of
                         NP_666258.2) aa819-846: myc-myc-hexahistidine tag
source                  1..846
                        mol_type = protein
                        organism = synthetic construct
SEQUENCE: 94
LNLAYPISPW KFKLFCGPPN TTDDSFLSPA GAPNNASALK GASEAIVEAK FNSSGIYVPE  60
LSKTVFHCCF GNEQGQNCSA LTDNTEGKTL ASVVKASVFR QLGVNWDIEC WMKGDLTLFI  120
CHMEPLPKNP FKNYDSKVHL LYDLPEVIDD SPLPPLKDSF QTVQCNCSLR GCECHVPVPR  180
AKLNYALLMY LEITSAGVSF QSPLMSLQPM LVVKPDPPLG LHMEVTDDGN LKISWDSQTM  240
APFPLQYQVK YLENSTIVRE AAEIVSATSL LVDSVLPGSS YEVQVRSKRL DGSGVWSDWS  300
SPQVFTTQDV VYFPPKILTS VGSNASFHCI YKNENQIISS KQIVWWRNLA EKIPEIQYSI  360
VSDRVSKVTF SNLKATRPRG KFTYDAVYCC NEQACHHRYA ELYVIDVNIN ISCETDGYLT  420
KMTCRWSPST IQSLVGSTVQ LRYHRRSLYC PDSPSIHPTS EPKNCVLQRD GFYECVFQPI  480
FLLSGYTMWI RINHSLGSLD SPPTCVLPDS VVKPLPPSNV KAEITVNTGL LKVSWEKPVF  540
PENNLQFQIR YGLSGKEIQW KTHEVFDAKS KSASLLVSDL CAVYVVQVRC RRLDGLGYWS  600
NWSSPAYTLV MDVKVPMRGP EFWRKMDGDV TKKERNVTLL WKPLTKNDSL CSVRRYVVKH  660
RTAHNGTWSE DVGNRTNLTF LWTEPAHTVT VLAVNSLGAS LVNFNLTFSW PMSKVSAVES  720
LSAYPLSSSC VILSWTLSPD DYSLLYLVIE WKILNEDDGM KWLRIPSNVK KFYIHDNFIP  780
IEKYQFSLYP VFMEGVGKPK IINGFTKDAI DKQQNDAGEQ KLISEEDLGG EQKLISEEDL  840
HHHHHH                                                             846
```

-continued

```
SEQ ID NO: 95          moltype = AA  length = 846
FEATURE                Location/Qualifiers
REGION                 1..846
                       note = rLEPR-mmh aa 1-818: rat LEPR (L22-G839 of
                        NP_036728.1) aa819-846: myc-myc-hexahistidine tag
source                 1..846
                       mol_type = protein
                       organism = synthetic construct
SEQUENCE: 95
LNLAYPTSPW RFKLFCAPPS TTDDSFLSPA GVPNNTSSLK GASEALVEAK FNSTGIYVSE  60
LSKTIFHCCF GNEQGQNCSA LTGNTEGKTL ASVVKPLVFR QLGVNWDIEC WMKGDLTLFI  120
CHMEPLLKNP FKNYDSKVHL LYDLPEVIDD LPLPPLKDSF QTVQCNCSVR ECECHVPVPR  180
AKVNYALLMY LEITSAGVSF QSPLMSLQPM LVVKPDPPLG LRMEVTDDGN LKISWDSQTK  240
APFPLQYQVK YLENSTIVRE AAEIVSDTSL LVDSVLPGSS YEVQVRSKRL DGSGVWSDWS  300
LPQLFTTQDV MYFPPKILTS VGSNASFCCI YKNENQTISS KQIVWWMNLA EKIPETQYNT  360
VSDHISKVTF SNLKATRPRG KFTYDAVYCC NEQACHHRYA ELYVIDVNIN ISCETDGYLT  420
KMTCRWSPST IQSLVGSTVQ LRYHRRSLYC PDNPSIRPTS ELKNCVLQTD GFYECVFQPI  480
FLLSGYTMWI RINHSLGSLD SPPTCVLPDS VVKPLPPSNV KAEITINTGL LKVSWEKPVF  540
PENNLQFQIR YGLNGKEIQW KTHEVFDAKS KSASLPVSDL CAVYVVQVRC RRLDGLGYWS  600
NWSSPAYTLV MDVKVPMRGP EFWRIMDGDI TKKERNVTLL WKPLMKNDSL CSVRRYVVKH  660
RTAHNGTWSQ DVGNQTNLTF LWAESAHTVT VLAINSIGAS LVNFNLTFSW PMSKVNAVQS  720
LSAYPLSSSC VILSWTLSPN DYSLLYLVIE WKNLNDDDGM KWLRIPSNVN KYYIHDNFIP  780
IEKYQFSLYP VFMEGVGKPK IINGFTKDDI AKQQNDAGEQ KLISEEDLGG EQKLISEEDL  840
HHHHHH                                                             846
```

What is claimed is:

1. An isolated monospecific antibody comprising two light chain variable regions which are linked to light chain constant regions and two heavy chain variable regions which are linked to heavy chain constant regions, inter-connected by disulfide bonds;

wherein (a) the heavy chain variable regions comprise the complementarity determining regions of a heavy chain variable region that comprises an amino acid sequence set forth in a SEQ ID NO selected from the group consisting of SEQ ID NO: 2, SEQ ID NO: 42, and SEQ ID NO: 58; and (b) the light chain variable regions comprise the complementarity determining regions of a light chain variable region that comprises the amino acid sequence set forth in SEQ ID NO: 10.

2. The isolated monospecific antibody of claim 1, wherein the light chain variable regions comprise:

an LCDR1 that comprises the amino acid sequence set forth in SEQ ID NO: 12;

an LCDR2 that comprises the amino acid sequence set forth in SEQ ID NO: 14, and an LCDR3 that comprises the amino acid sequence set forth in SEQ ID NO: 16;

and the heavy chain variable regions comprise:

(i)

an HCDR1 that comprises the amino acid sequence set forth in SEQ ID NO: 4;

an HCDR2 that comprises the amino acid sequence set forth in SEQ ID NO: 6; and an HCDR3 that comprises the amino acid sequence set forth in SEQ ID NO: 8;

(ii)

an HCDR1 that comprises the amino acid sequence set forth in SEQ ID NO: 44;

an HCDR2 that comprises the amino acid sequence set forth in SEQ ID NO: 46; and an HCDR3 that comprises the amino acid sequence set forth in SEQ ID NO: 48;

or (iii)

an HCDR1 that comprises the amino acid sequence set forth in SEQ ID NO: 60;

an HCDR2 that comprises the amino acid sequence set forth in SEQ ID NO: 62; and an HCDR3 that comprises the amino acid sequence set forth in SEQ ID NO: 64.

3. The isolated monospecific antibody of claim 1, wherein the light chain variable regions comprise:

an LCDR1 that comprises the amino acid sequence set forth in SEQ ID NO: 12;

an LCDR2 that comprises the amino acid sequence set forth in SEQ ID NO: 14; and an LCDR3 that comprises the amino acid sequence set forth in SEQ ID NO: 16; and the heavy chain variable regions comprise:

an HCDR1 that comprises the amino acid sequence set forth in SEQ ID NO: 4;

an HCDR2 that comprises the amino acid sequence set forth in SEQ ID NO: 6; and an HCDR3 that comprises the amino acid sequence set forth in SEQ ID NO: 8.

4. The isolated monospecific antibody of claim 1, wherein the light chain variable regions comprise:

an LCDR1 that comprises the amino acid sequence set forth in SEQ ID NO: 12;

an LCDR2 that comprises the amino acid sequence set forth in SEQ ID NO: 14; and an LCDR3 that comprises the amino acid sequence set forth in SEQ ID NO: 16; and the heavy chain variable regions comprise:

an HCDR1 that comprises the amino acid sequence set forth in SEQ ID NO: 44;

an HCDR2 that comprises the amino acid sequence set forth in SEQ ID NO: 46; and an HCDR3 that comprises the amino acid sequence set forth in SEQ ID NO: 48.

5. The isolated monospecific antibody of claim 1, wherein the light chain variable regions comprise:

an LCDR1 that comprises the amino acid sequence set forth in SEQ ID NO: 12;

an LCDR2 that comprises the amino acid sequence set forth in SEQ ID NO: 14; and an LCDR3 that comprises the amino acid sequence set forth in SEQ ID NO: 16; and the heavy chain variable regions comprise:

an HCDR1 that comprises the amino acid sequence set forth in SEQ ID NO: 60;

an HCDR2 that comprises the amino acid sequence set forth in SEQ ID NO: 62; and an HCDR3 that comprises the amino acid sequence set forth in SEQ ID NO: 64.

6. The isolated monospecific antibody of claim 1, wherein the heavy chain variable regions comprise the amino acid sequence set forth in SEQ ID NO: 2 and the light chain variable regions comprise the amino acid sequence set forth in SEQ ID NO: 10.

7. The isolated monospecific antibody of claim 1, wherein the heavy chain variable regions comprise the amino acid sequence set forth in SEQ ID NO: 42 and the light chain variable regions comprise the amino acid sequence set forth in SEQ ID NO: 10.

8. The isolated monospecific antibody of claim 1, wherein the heavy chain variable regions comprise the amino acid sequence set forth in SEQ ID NO: 58 and the light chain variable regions comprise the amino acid sequence set forth in SEQ ID NO: 10.

9. The isolated monospecific antibody of claim 6 wherein the light chain variable regions are linked to kappa light chain constant domains.

10. The isolated monospecific antibody of claim 7 wherein the light chain variable regions are linked to kappa light chain constant domains.

11. The isolated monospecific antibody of claim 8 wherein the light chain variable regions are linked to kappa light chain constant domains.

12. A pharmaceutical composition comprising the isolated monospecific antibody of claim 6 and a pharmaceutically acceptable carrier or diluent.

13. A pharmaceutical composition comprising the isolated monospecific antibody of claim 7 and a pharmaceutically acceptable carrier or diluent.

14. A pharmaceutical composition comprising the isolated monospecific antibody of claim 8 and a pharmaceutically acceptable carrier or diluent.

15. An autoinjector that comprises the pharmaceutical composition of claim 12.

16. An autoinjector that comprises the pharmaceutical composition of claim 13.

17. An autoinjector that comprises the pharmaceutical composition of claim 14.

18. A pen delivery device that comprises the pharmaceutical composition of claim 12.

19. A pen delivery device that comprises the pharmaceutical composition of claim 13.

20. A pen delivery device that comprises the pharmaceutical composition of claim 14.

* * * * *